(12) United States Patent
Szkudlinski et al.

(10) Patent No.: US 8,377,879 B2
(45) Date of Patent: Feb. 19, 2013

(54) FOLLICLE STIMULATING HORMONE SUPERAGONISTS

(75) Inventors: Mariusz W. Szkudlinski, Rockville, MD (US); Bruce D. Weintraub, Rockville, MD (US)

(73) Assignee: Trophogen, Inc., Rockville, MD (US)

( * ) Notice: Subject to any disclaimer, the term of this patent is extended or adjusted under 35 U.S.C. 154(b) by 0 days.

(21) Appl. No.: 13/187,956

(22) Filed: Jul. 21, 2011

(65) Prior Publication Data

US 2012/0035109 A1   Feb. 9, 2012

Related U.S. Application Data

(63) Continuation of application No. 10/593,466, filed as application No. PCT/US2005/089600 on Mar. 18, 2005, now abandoned.

(60) Provisional application No. 60/554,419, filed on Mar. 19, 2004.

(51) Int. Cl.
*A61K 38/24* (2006.01)
*C07K 14/59* (2006.01)

(52) U.S. Cl. .......................... 514/9.9; 530/350; 530/398

(58) Field of Classification Search .................. None
See application file for complete search history.

(56) References Cited

U.S. PATENT DOCUMENTS

2002/0127652 A1*   9/2002   Schambye et al. ........... 435/69.4

OTHER PUBLICATIONS

Dias and Van Roey, Archives of Medical Research, 2001, 32: 510-519.*
Alignment between the bovine and human gonadotropin alpha subunit is provided (downloaded on Jan. 25, 2012 from the website: blast.ncbi.nlm.nih.gov/Blast.cgi; 2 pages total.*

* cited by examiner

*Primary Examiner* — Bridget E Bunner
*Assistant Examiner* — Christina Borgeest
(74) *Attorney, Agent, or Firm* — Morgan, Lewis & Bockius LLP

(57) ABSTRACT

This invention provides superactive analogs of FSH demonstrating enhanced bioactivity both in vitro and in vivo as compared to wild type FSH. In particular, the analogs of the invention demonstrate at least a ten fold increase in potency or at least a ten percent increase in maximal efficacy as compared to wild type protein. The analogs are particularly useful in treating subjects showing low FSH receptor expression or poor FSH receptor responsiveness, and for the treatment of any condition associated with glycoprotein hormone activity.

7 Claims, 37 Drawing Sheets

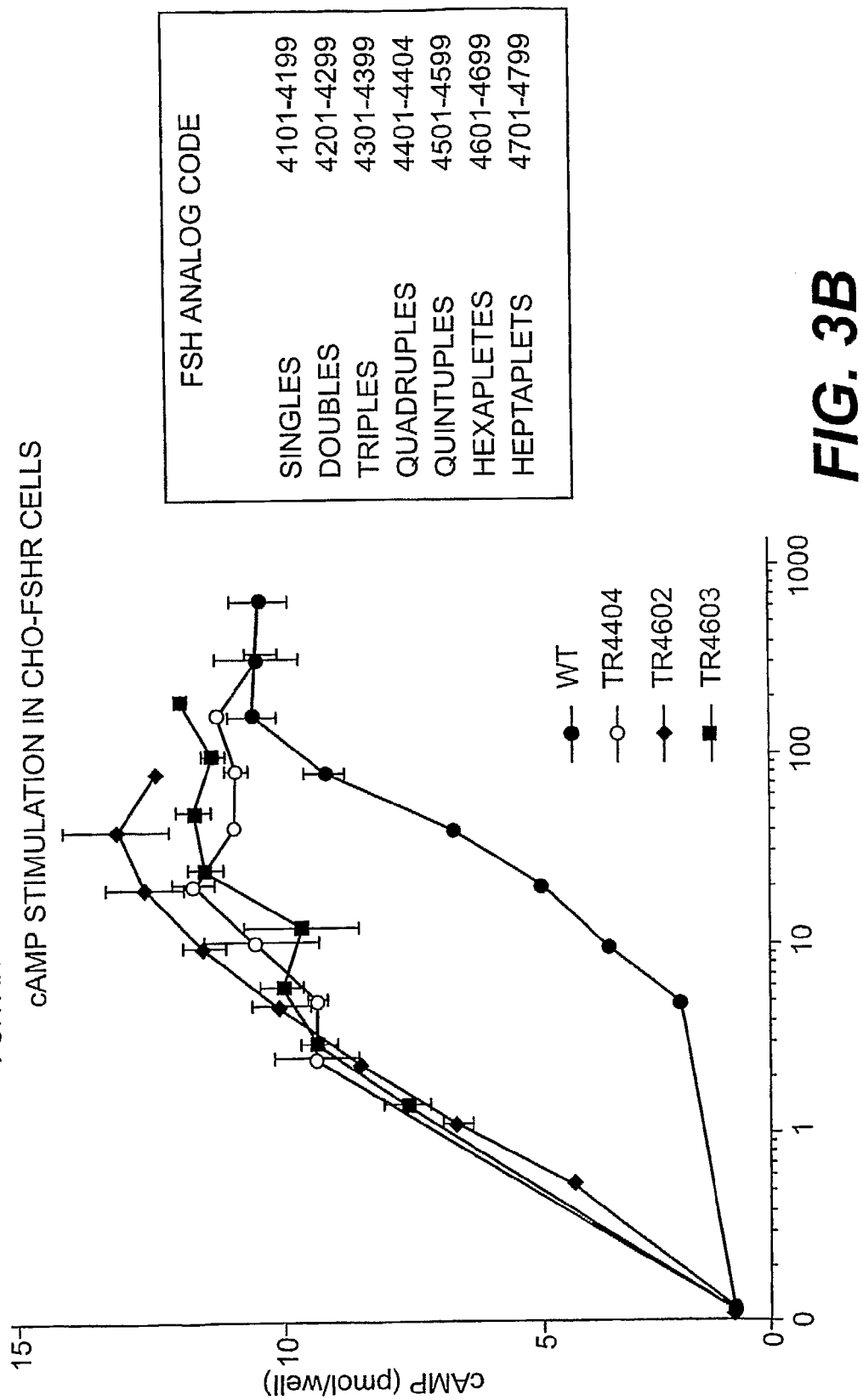

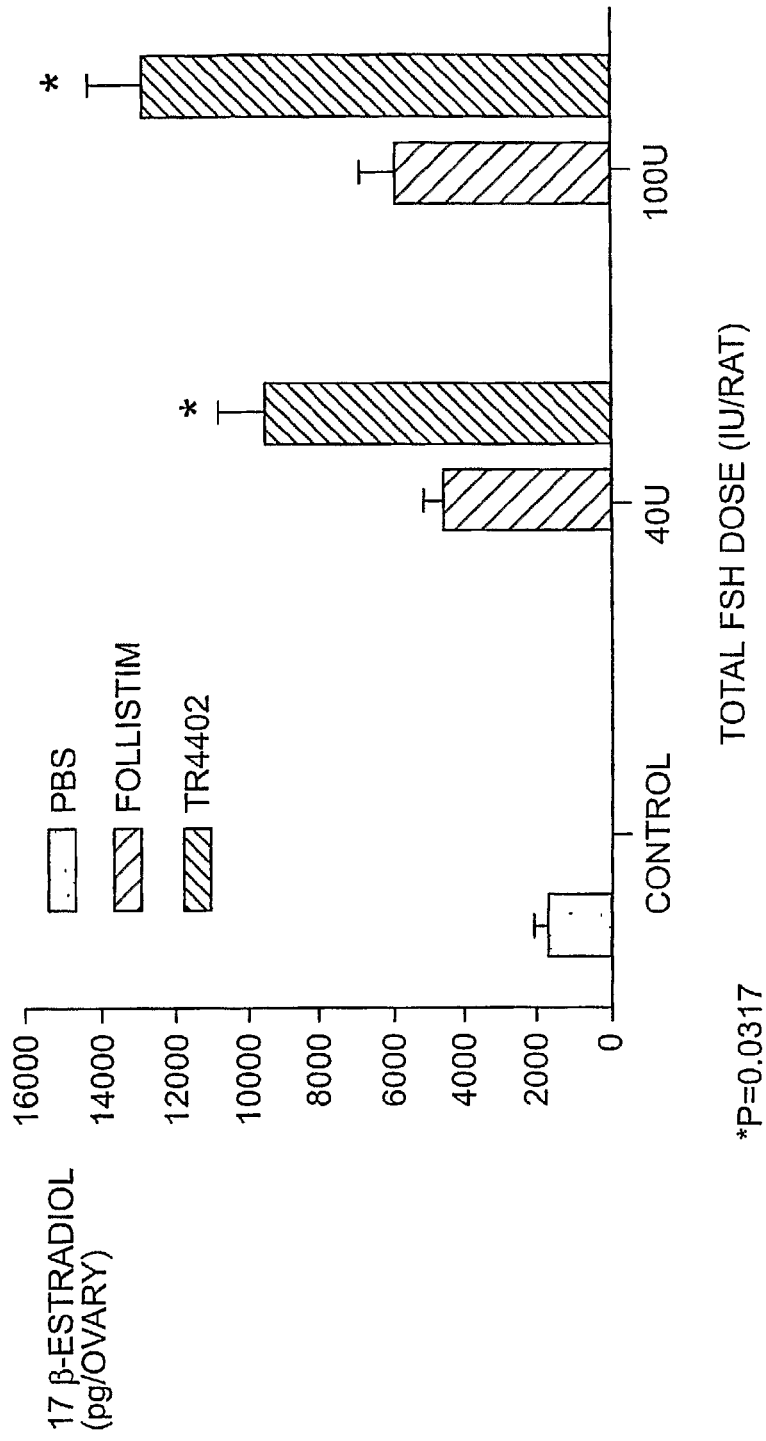

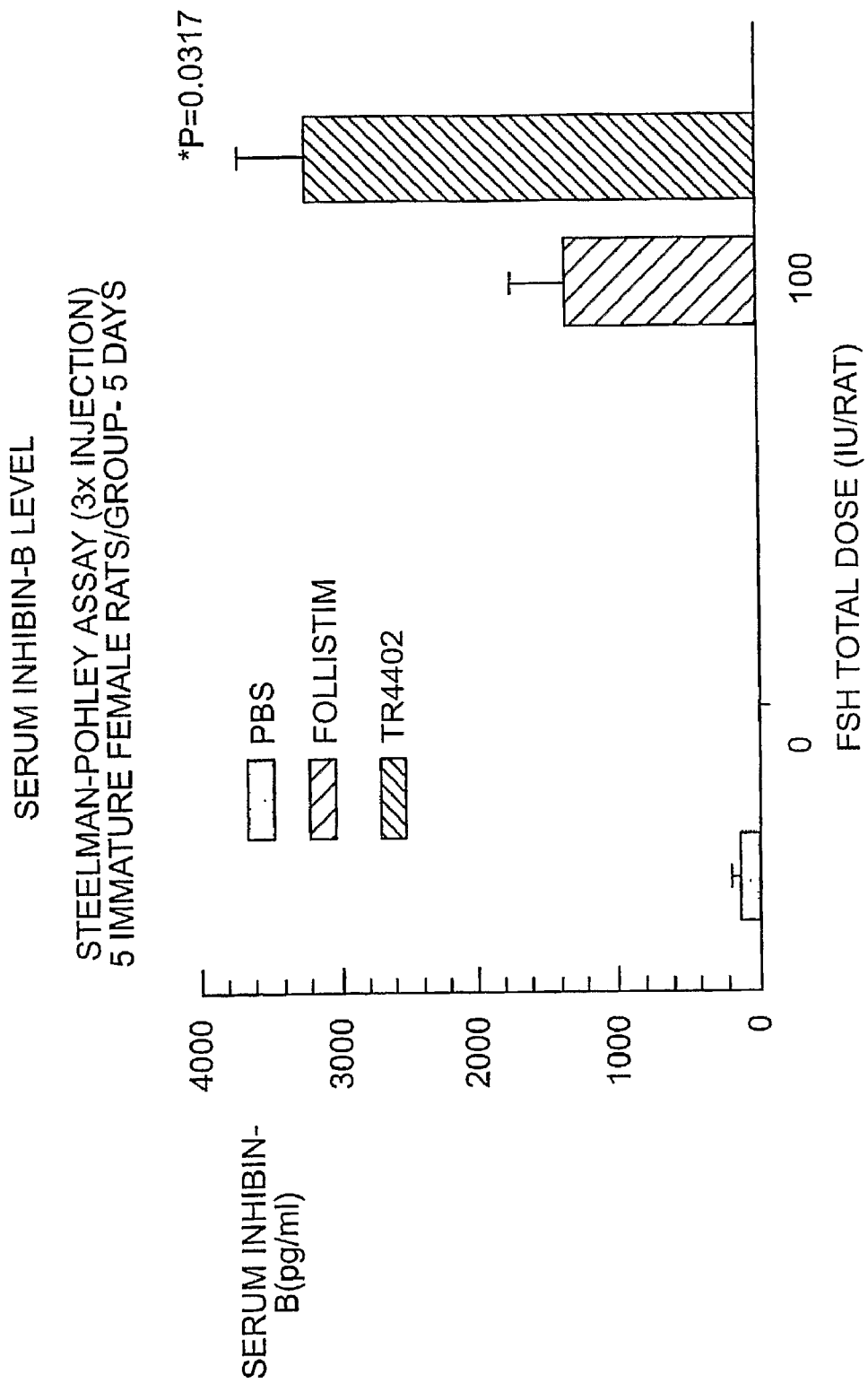

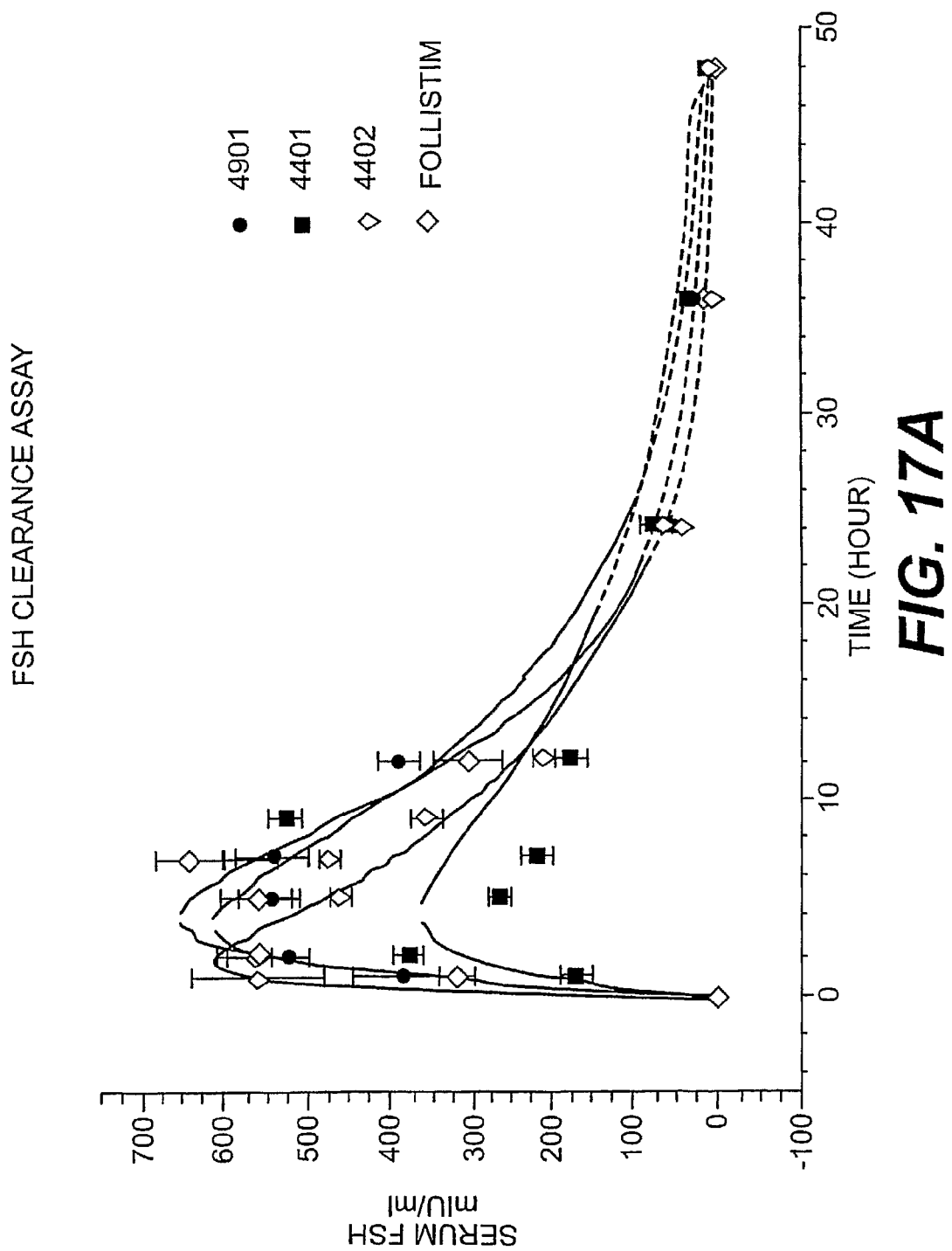

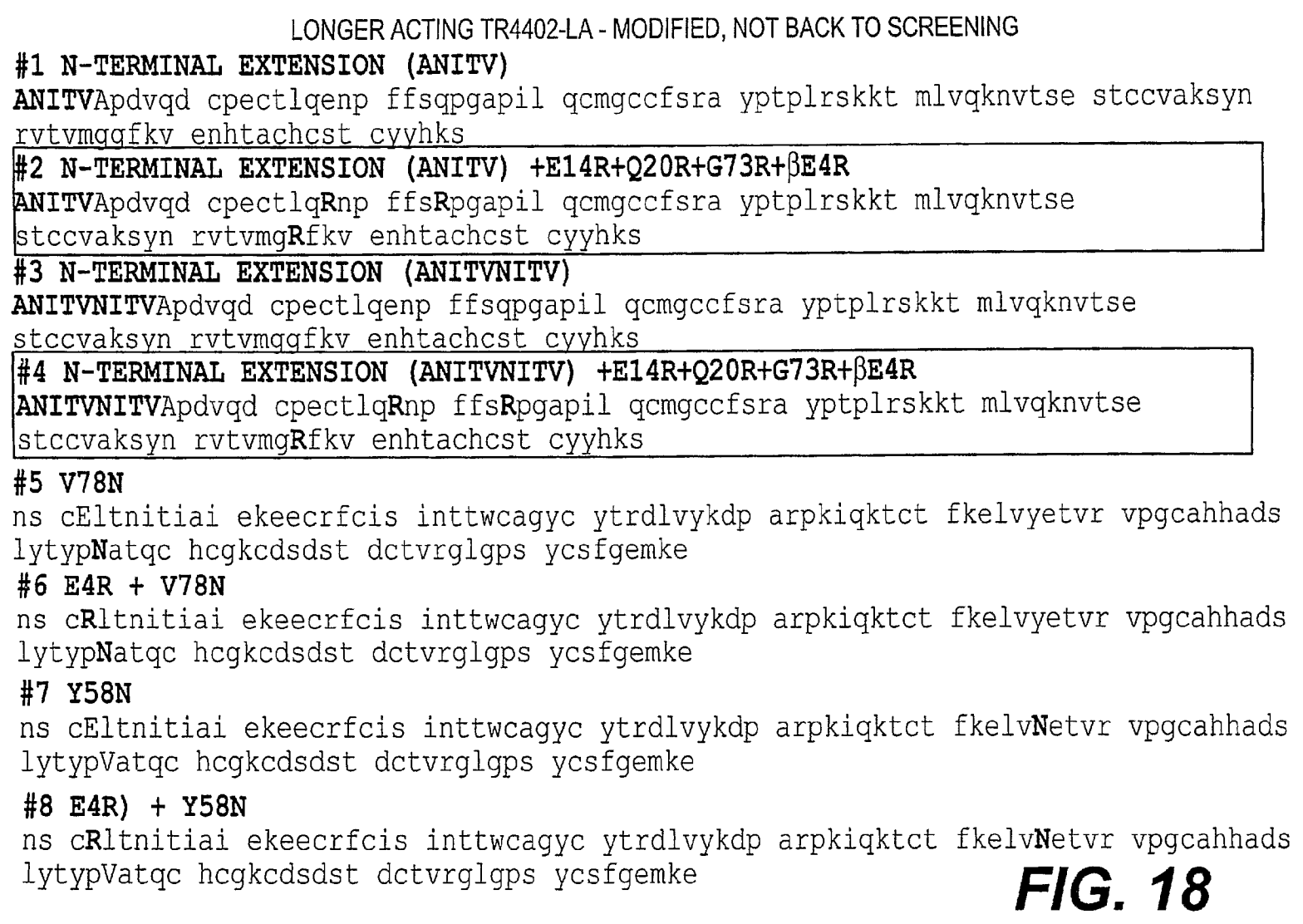

LONGER ACTING TR4402-LA - MODIFIED, NOT BACK TO SCREENING

1 N-TERMINAL EXTENSION (ANITV)
ANITVApdvqd cpectlqenp ffsqpgapil qcmgccfsra yptpl

FOLLICLE STIMULATING HORMONE SUPERAGONISTS

RELATED APPLICATIONS

The present application is a Continuation of U.S. patent application Ser. No. 10/593,466, filed on Sep. 19, 2006, which is a U.S. National Phase Application of International Application PCT/US2005/008960, filed Mar. 18, 2005, which claims the benefit of U.S. Provisional Application No. 60/554,419, filed Mar. 19, 2004, all of which are herein incorporated by reference in their entirety for all purposes.

FIELD OF INVENTION

This invention relates generally to modified follicle stimulating hormones (FSH) having superagonist activity, and the use thereof in the treatment of conditions associated with glycoprotein hormone activity. More specifically, this invention relates to modified FSH molecules containing two or more amino acid substitutions as compared to wild type FSH, wherein such modified FSH molecules exhibit enhanced pharmacological properties as compared to wild type FSH.

BACKGROUND OF INVENTION

Description of the Text File Submitted Electronically

The contents of the text file submitted electronically herewith are incorporated herein by reference in their entirety: A computer readable format copy of the Sequence Listing (filename: TROP_001_02US_SeqList.ST25.txt, date recorded: Oct. 11, 2011, file size 38 kilobytes).

Follitropin (follicle-stimulating hormone, FSH) and the gonadotropins chorionic gonadotropin, (CG), lutropin (luteinizing hormone, LH), and thyrotropin (thyroid-stimulating hormone, TSH) comprise the family of glycoprotein hormones. Each hormone is a heterodimer of two non-covalently linked subunits: alpha and beta. Within the same species, the amino acid sequence of the alpha-subunit is identical in all the hormones, whereas the sequence of the beta-subunit is hormone specific (Pierce, J. G. and Parsons, T. F. "Glycoprotein hormones: structure and function." Ann. Rev. Biochem. 50:465-495 (1981)). The fact that the sequences of the subunits are highly conserved from fish to mammals implies that these hormones have evolved from a common ancestral protein (Fontaine Y-A. and Burzawa-Gerard, E. "Esquisse de l' evolution des hormones gonadotopes et thyreotropes des vertebres." Gen. Comp. Endocrinol. 32:341-347 (1977)).

Recombinant follitropin has been used in certain therapies, such as in the treatment of patients suffering from infertility (Lathi and Milki, "Recombinant gonadotropins," Curr Womens Health Rep. 1(2):157-63 (2001)). The hormone has been used in women to induce ovulation, and also in men to induce spermatogenesis (Bouloux et al., "Induction of spermatogenesis by recombinant follicle-stimulating hormone (puregon) in hypogonadotropic azoospermic men who failed to respond to human chorionic gonadotropin alone," J. Androl. 24(4): 604-11 (2003)), improve disturbed sperm structures (Haidl et al., "Drug treatment of male fertility disorders," Asian J. Androl. 2(2):81-5 (2000)), and treat conditions associated with decreased levels of testosterone (see U.S. Pat. Nos. 5,574,011 and 6,562,790, each incorporated by reference). The response of women to exogenous FSH therapy, has been shown to be variable, with some demonstrating a poor response to a standard therapy protocol (requiring adjustment of the FSH doses), and others demonstrating ovarian hyperstimulation syndrome (Perez et al., "Ovarian response to follicle-stimulating hormone (FSH) stimulation depends on the FSH receptor genotype," J Clin Endocrinol Metab. 85(9): 3365-9 (2000)). What is needed are modified derivatives of FSH having increased activity, to facilitate treatment of poor responders while permitting lower dose therapy regimens of patients prone to ovarian hyperstimulation.

SUMMARY OF INVENTION

This invention encompasses modified FSH proteins and nucleic acids encoding the same, wherein the in vivo and in vitro bioactivities of the modified proteins are substantially increased as compared to wild type FSH. In particular, the modified analogs of the invention demonstrate surprisingly enhanced pharmacological properties, including potency and Vmax (efficacy), as compared to wild type FSH. Further, the modified analogs of the invention provide dramatic increases in the quantity and quality of oocytes, blastocysts and embryos of treated animals. The analogs of the invention thus provide a long awaited solution for a wide spectrum of patients suffering from infertility, including women demonstrating a poor response following in vitro fertilization (IVF), women who have been disqualified from IVF, women demonstrating low numbers of FSH receptors and women with FSH receptor mutations leading to infertility.

The modified FSH molecules of the invention contain at least a modified α-subunit containing a combination of at least two mutations in peripheral loops of FSH, which lead to a modified FSH having increased potency over wild type FSH or modified proteins comprising the specified mutations alone. Typically, the modified FSH proteins of the invention demonstrate at least about a ten fold increase in potency over wild type FSH, with preferred α-subunit mutations comprising at least two basic amino acids at positions corresponding to positions 13, 14, 16, 17, 20, 21, 22, 66, 68, 73, 74 and 81 of SEQ ID No. 1.

The modified FSH proteins of the invention may further comprise a modified β-subunit, particularly a modified β-subunit comprising at least one basic amino acid at a position corresponding to any one of positions 2, 4, 14, 63, 64, 67 and 69 of SEQ ID No. 2. The modified FSH proteins of the invention may also demonstrate an increased or decreased plasma half-life as compared to wild type FSH or a decreased plasma half-life as compared to wild type FSH. An increase in plasma half-life may be facilitated by pegylation, by inclusion of a potential glycosylation site or by other means.

The invention also includes methods of assisting reproduction in a subject comprising administering an assisting amount of the modified FSH of the invention, for instance in an in vitro fertilization protocol or artificial insemination protocol or other protocol in which ovulation or spermatogenesis is induced. Also included are methods of diagnosing and treating conditions associated with glycoprotein hormone activity in women, including but not limited to ovulatory dysfunction, luteal phase defects, time-limited conception, low FSH receptor expression in growing follicles, low FSH receptor sensitivity, FSH receptor binding and/or coupling deficiencies, pituitary failure or injury, unexplained infertility and ovarian carcinoma. The modified FSH proteins of the invention are particularly useful for treating women prone to ovarian hyperstimulation, where analogs with the longest half-life may be applied early in the cycle and those with shorter half-life later in the cycle to prevent or reduce the possibility of ovarian hyperstimulation syndrome (OHHS). Also included are methods of diagnosing and treating conditions associated with glycoprotein hormone activity in men, including but not limited to male factor infertility, pituitary failure or injury, male pattern baldness, testicular carcinoma and any condition associated with deficient levels of testosterone production.

BRIEF DESCRIPTION OF THE DRAWINGS

FIGS. 3A and 3B are graphs showing a comparison of the effect of various combined mutations on FSH bioactivity in vitro, as measured using transient transfection of CHO-FSHR cells.

FIG. 4A shows cross-reactivity between FSH TR-4402 and rat luteinizing hormone receptor.

FIG. 15 is a graph showing the intra-ovarian estradiol content of rats treated with wild type FSH (Follistim) as compared to rats treated with the analog TR-4402.

FIG. 16 is a graph showing serum inhibin B levels in rats after stimulation with corresponding doses of wild type FSH (Follistim) and the analog TR-4402.

FIG. 18 shows N-terminal extensions which can be used to prolong half life of FSH analogs (SEQ. ID Nos. 3, 4, 5, 6, 7, 8, 9, 10, 11, and 12).

DETAILED DESCRIPTION OF THE INVENTION

Figure 1A:
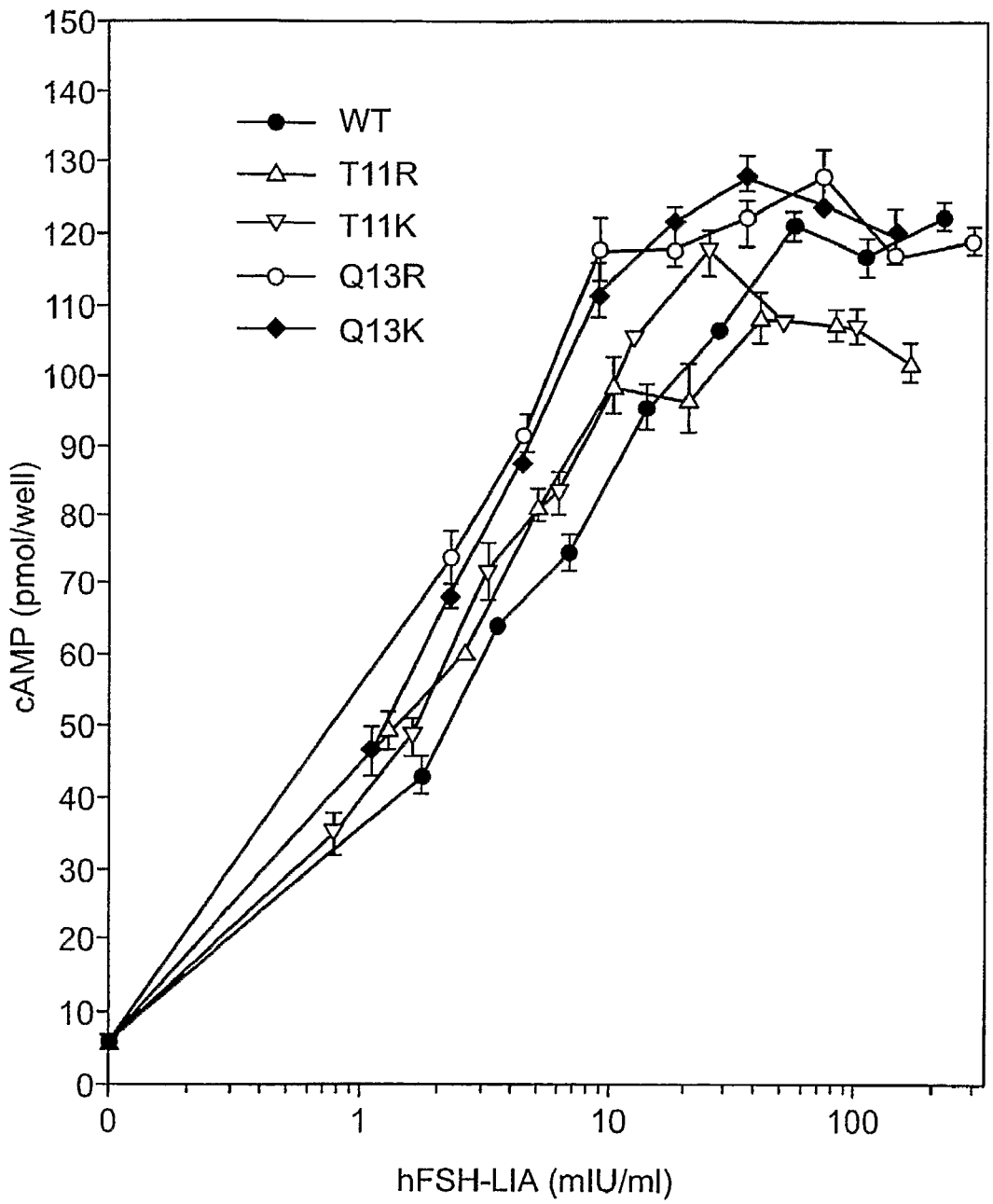
FIGS. 1A-E are graphs showing a comparison of the effect of various single mutations on FSH bioactivity in vitro compared to wild type (WT), as measured using transient transfection of CHO-FSHR cells.
Figure 1B:
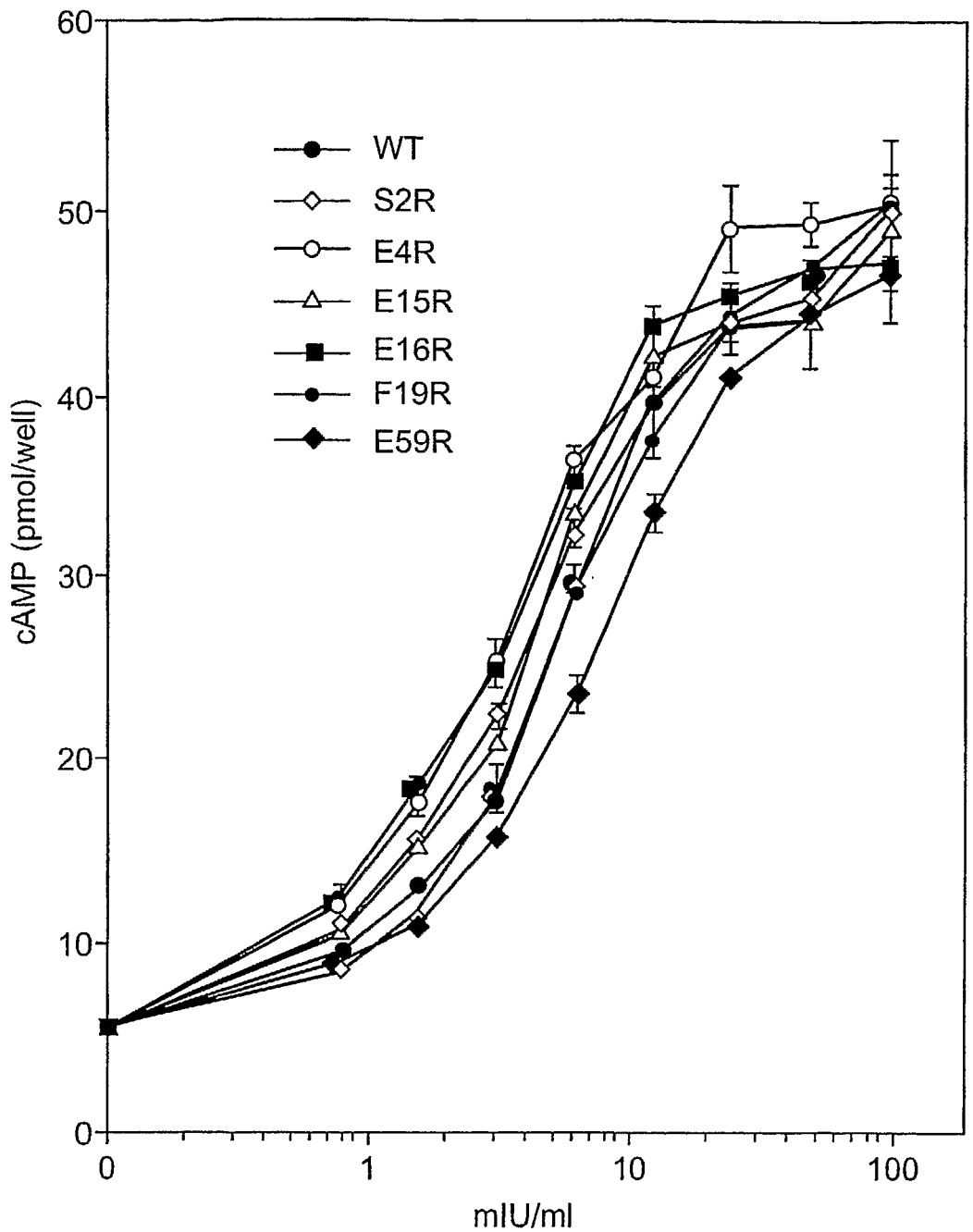
Figure 1C:
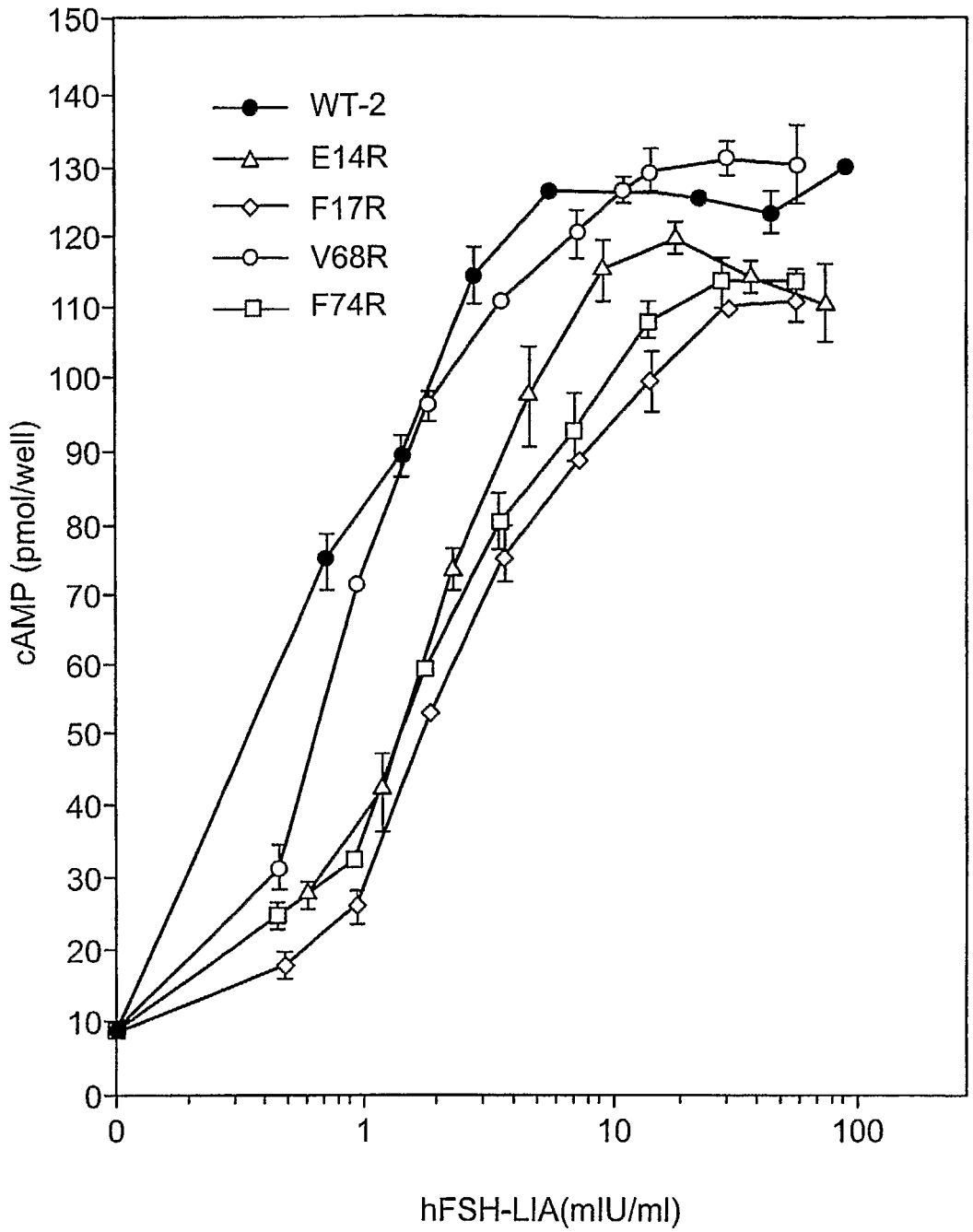
Figure 1D:
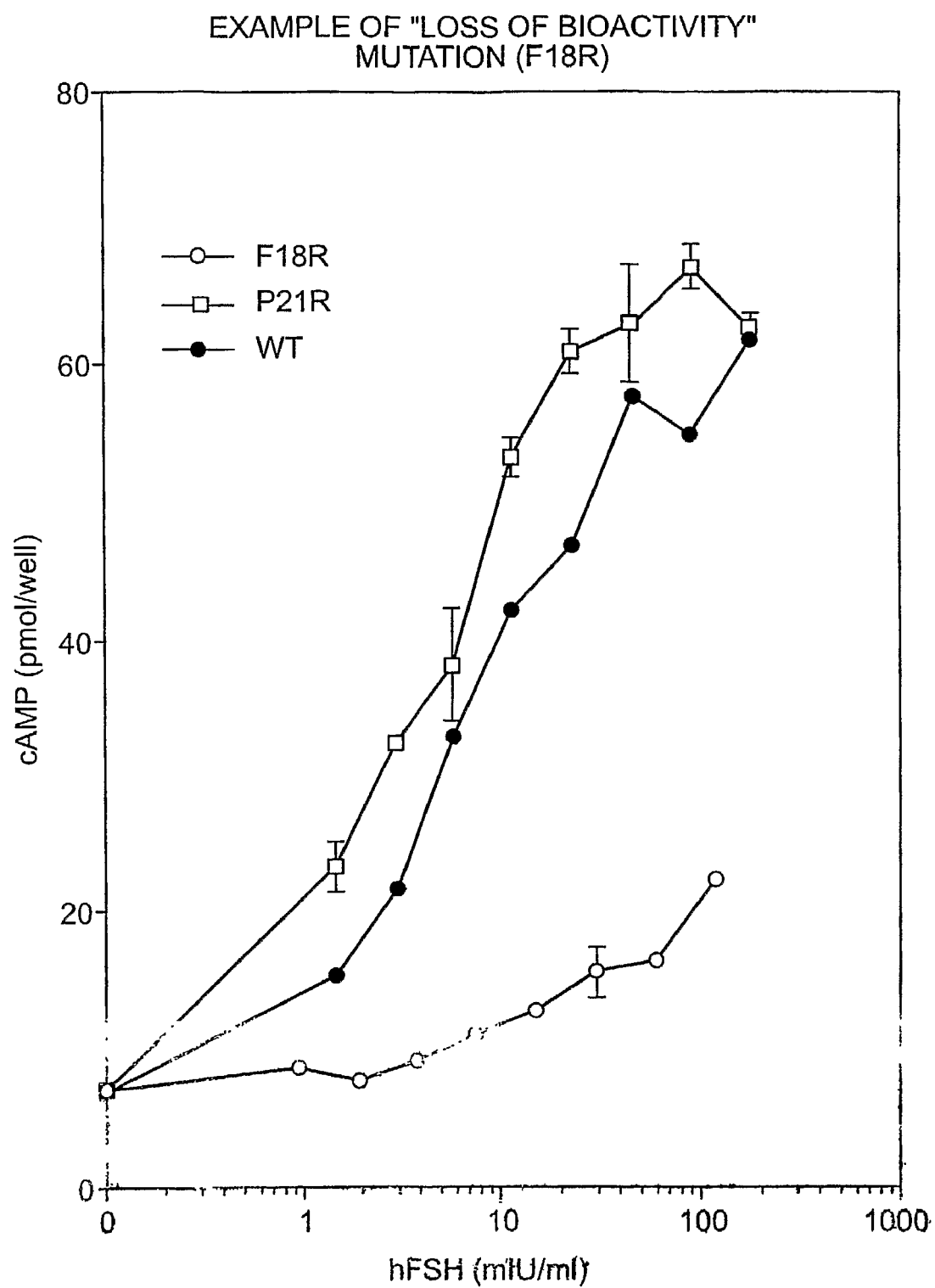
Figure 1E:
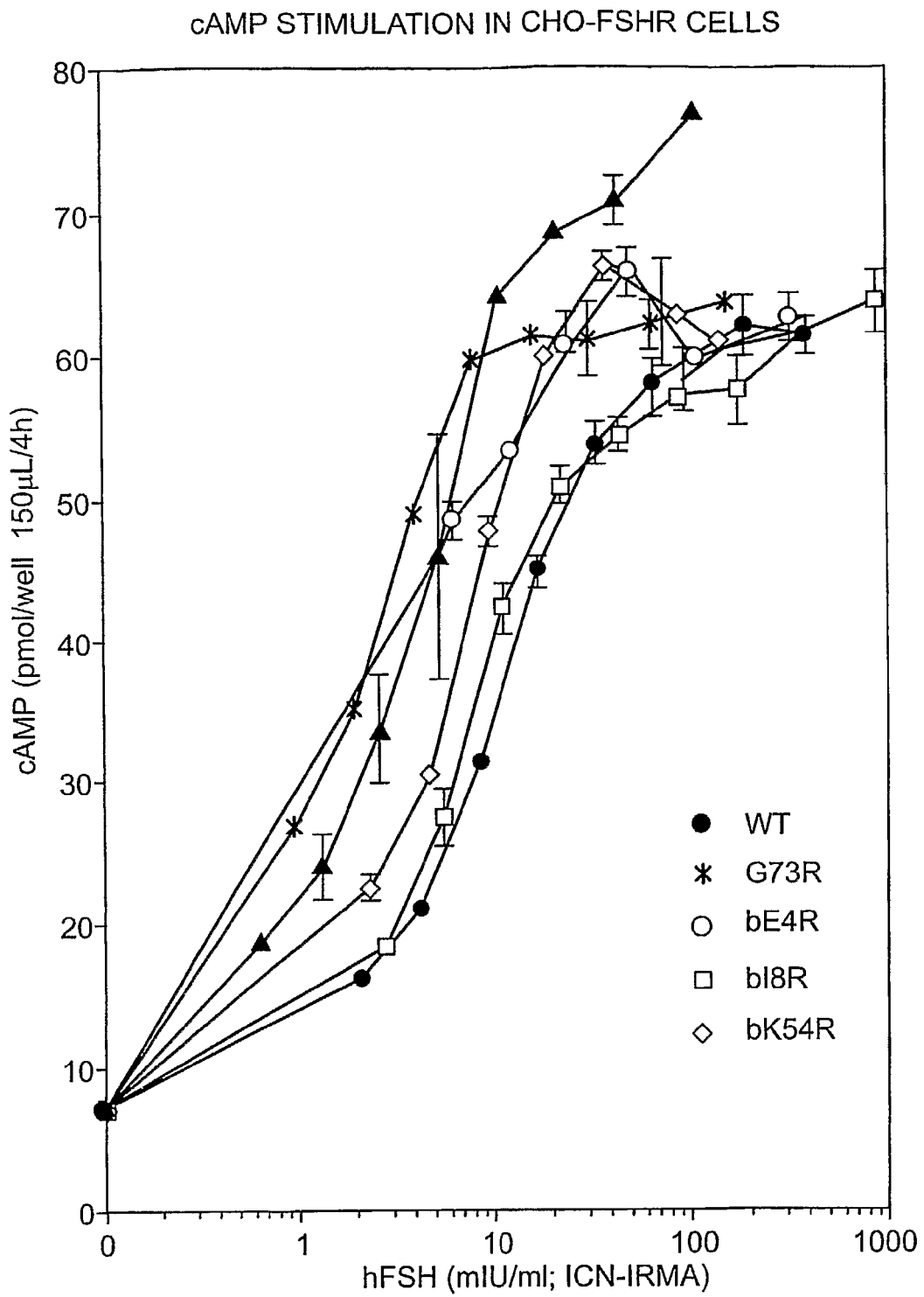

The present invention provides modified "superactive" FSH molecules showing surprisingly enhanced potency as compared to wild type FSH. Being "modified" means that, while the protein contains an amino acid sequence which differs from the wild-type FSH, the sequence has not been changed such that it is identical to the known FSH sequence of another species. "Superactivity" may be assessed according to a variety of parameters, including potency and efficacy. "Potency" is a parameter of bioactivity that is determined by measuring the half maximal response. Differences in "potency" are determined by comparing the value of the FSH response of the analog halfway between baseline and maximum (EC50) versus that of wild type FSH. FSH responses may be measured in vitro using purified proteins, or may be estimated following transient transfection of a nucleic acid encoding the modified protein. FSH responses may also be measured in vivo, i.e. in an animal responsive to said FSH analog. Such responses encompass any known cellular or biological and quantitative or qualitative response of FSH binding to its receptor, i.e. cAMP production, synthesis of proteins such as progesterone, fertilization rate, blastocyst formation rate, embryo development per fertilized oocyte, etc.

"Efficacy" (Vmax) or maximum response is another parameter of bioactivity. As discussed herein, parameters of bioactivity may vary depending on receptor number and receptor coupling in the assay cell line. In systems with lower receptor numbers or impaired coupling, differences are more discernable in terms of Vmax (efficacy). In systems where receptors are overexpressed, differences in potency are more visible.

In vivo quantitative and qualitative parameters such as quantity of oocytes, fertilization rate and blastocyst and embryo formation rates may be measured at the maximally effective dose for oocyte number. The maximally effective dose for oocyte number is the optimal amount of superactive FSH for both oocyte quality and quantity. The maximally effective dose for oocyte number is dependent on an animal's weight and rate of metabolism. For example, the maximally effective dose for a larger animal with a slower rate of metabolism is greater than the maximally effective dose for a smaller animal with a higher rate of metabolism. The maximally effective dose is determined empirically for each animal.

However, regardless of the system used, the modified superactive FSH proteins of the invention demonstrate at least about a 10 fold increase in potency more preferably at least about a 20 fold, 30 fold, 40 fold, 50 fold, 60 fold, 70 fold, 80 fold, 90 fold or even 100 fold increase in potency compared to wild type FSH, or about a 10% increase in maximal efficacy, more preferably at least a 20%, 30%, 40%, 50%, 60%, 70%, 80%, 90%, or even 100% increase in maximal efficacy compared to wild type FSH. The superactive analogs of the invention may also provide about a five to ten fold increase in potency or 5% to 10% increase in maximal efficacy as compared to wildtype FSH. Some of the modified proteins of the invention demonstrate at least about a thirty to fifty fold increase in potency or 30% to 50% increase in maximal efficacy as compared to wild type. Thus, the modified FSH proteins of the present invention are particularly useful for treating patients with low receptor number or deficiencies in receptor response, since the modified proteins of the invention maintain at least a 10 fold increase in potency or 10% increase in maximal efficacy even in systems with low receptor number or response.

The rate of absorption of a modified superactive FSH may result in increased or decreased duration of action. A modified FSH analog with an increased rate of absorption and decreased duration of action may be beneficial for hypersensitive patients at risk for hyperstimulation syndrome. The rate of absorption is measured by $K_a$. The rate of elimination is measured by $K_e$.

The modified FSH molecules of the invention include modified proteins of species selected from the group consisting of human, bovine, equine, porcine, ovine, murine, rat, rabbit, primate, fish, etc. Fish FSH (also known as GTH-1) may be used in aquaculture, i.e., in order to grow endangered or other fish species in captivity. Other species of modified FSH find use in agriculture breeding, and in the laboratory setting for testing the effects of different combined mutations on various male and female glycoprotein hormone-related conditions. The modified FSH molecules of other species have substitutions at positions corresponding to those in the modified human FSH molecules disclosed herein, which may be identified using any alignment program, including but not limited to DNASIS, ALIONment, SIM and GCG programs such as Gap, BestFit, FrameAlign and Compare.

Modified human FSH molecules of the present invention comprise at least a modified α-subunit, wherein the alpha subunit comprises at least two basic amino acids such as those at positions corresponding to positions 13, 14, 16, 17, 20, 21, 22, 66, 68, 73, 74 and 81 of wild type human FSH alpha (SEQ ID No. 1). The modified proteins may also contain a modified beta subunit, wherein the beta subunit comprises at least one basic amino acid at positions corresponding to positions 2, 4, 14, 63, 64, 67 and 69 of wild type human FSH beta (SEQ ID No. 2). The modified proteins of the invention may also contain further substitutions, particularly conservative substitutions that do not alter the enhanced properties of the protein. Typically, however, such modified proteins will contain less than five substitutions at positions other than those listed above, and may exhibit complete amino acid sequence identity with the corresponding wild-type FSH alpha and beta subunits in positions other than the positions listed above.

Basic amino acids comprise the amino acids lysine, arginine, and histidine, and any other basic amino acid which may be a modification to any of these three amino acids, synthetic basic amino acids not normally found in nature, or any other amino acid which is positively charged at a neutral pH. Preferred basic amino acids, among others, are selected from the group consisting of lysine and arginine.

Exemplary modified FSH molecules having two basic amino acid substitutions include but are not limited to proteins with substitutions at positions 14 and 66 of the α-subunit, particularly E14R and N66R, positions 14 and 73 of the α-subunit, particularly E14R and G73R positions 16 and 20 of the α-subunit, particularly P16R and Q20R, and positions 20 and 21 of the α-subunit, particularly Q20R and P21R.

The modified FSH proteins of the invention may also have an α-subunit comprising three basic amino acid substitutions at positions selected from the group consisting of positions 13, 14, 16, 17, 20, 21, 22, 66, 68, 73, 74 and 81. Such modified proteins include but are not limited to proteins with combined substitutions at positions 16, 20 and 21, particularly P16R, Q20R and P21R, positions 14, 20 and 73, particularly E14R, Q20R and G73R, positions 66, 73 and 81, particularly N66K, G73K and A81K, positions 14, 66 and 73, particularly E14R, N66R and G73R, and positions 14, 21 and 73, particularly E14R, P21R and G73R.

The modified FSH proteins of the invention may also have an α-subunit comprising four basic amino acid substitutions at positions selected from the group consisting of positions 13, 14, 16, 17, 20, 21, 22, 66, 68, 73, 74 and 81. Such modified proteins include but are not limited to proteins with combined substitutions at positions 13, 14, 16 and 20, particularly the combination of Q13R, E14R, P16R and Q20R, and the combination of Q13K, E14K, P16K and Q20K.

The modified FSH proteins of the invention may also have an α-subunit comprising five basic amino acid substitutions at positions selected from the group consisting of positions 13, 14, 16, 17, 20, 21, 22, 66, 68, 73, 74 and 81. Such modified proteins include but are not limited to proteins with combined substitutions at positions 14, 20, 21, 66 and 73, particularly E14R, Q20R, P21R, N66R and G73R, and positions 14, 16, 20, 66 and 73, particularly E14R, P16R, Q20R, N66R and G73R.

The modified FSH proteins of the invention may also have an α-subunit comprising six basic amino acid substitutions at positions selected from the group consisting of positions 13, 14, 16, 17, 20, 21, 22, 66, 68, 73, 74 and 81. Such modified proteins include but are not limited to proteins with combined substitutions at positions 13, 14, 16, 20, 66 and 73, particularly Q13K, E14K, P16K, Q20K, N66K and G73K, and positions 14, 16, 20, 21, 66 and 73, particularly E14R, P16R, Q20R, P21R, N66R and G73R.

A particularly effective modified β-subunit of the invention comprises a basic amino acid at a position corresponding to position 4 of SEQ ID No. 2, and more particularly, E4R. This substitution results in a unique increase in FSH potency and expression level. The inventors have found that this mutation results in 2-3 fold higher production of recombinant FSH when used in combination with the other substitutions disclosed herein.

Design of FSH Superagonists

Superagonists encompassed by the present invention may be designed by comparing the amino acid sequences of the alpha and beta FSH of interest to that of other species to identify basic residues in the proteins of FSH of other species.

Such methods are disclosed in U.S. Pat. No. 6,361,992, which is herein incorporated by reference in its entirety. Consideration may also be given to the relative biological activity of FSH from various species as to which species to chose for comparison and substitution. Further, homology modeling based on the structure of related glycoprotein hormones is useful to identify surface-exposed amino acid residues.

Accordingly, the present invention also provides a modified FSH protein having increased potency over a wild-type FSH from the same species, wherein the modified FSH comprises a basic amino acid substituted at a position corresponding to the same amino acid position in a FSH protein from another species having an increased potency over the wild-type FSH protein. The glycoprotein being modified to increase its potency can be from a non-human species. For example, one can compare porcine FSH to bovine FSH, design porcine FSH proteins with amino acid substitutions at positions where the porcine and the bovine sequences are different, construct porcine FSH proteins with the selected changes, and administer the modified porcine FSH to porcine animals. Alternatively, the FSH being modified can be bovine.

The present invention also provides a modified FSH having increased potency over the wild-type FSH from the same species, wherein the modified FSH comprises a basic amino acid substituted at a position corresponding to the same amino acid position in a different glycoprotein hormone from the same species having an increased potency over the wild-type glycoprotein hormone. For example, the beta subunits of human FSH and human chorionic gonadotropin can be compared and amino acid substitutions to the FSH beta subunit can be made based on any sequence divergence. Naturally, only those changes which generally increase the potency of the modified FSH are contemplated since the hormone receptor specificity will still need to be retained.

To modify additional amino acid positions, glycoprotein hormone sequences from human and non-humans can be aligned using standard computer software programs such as DNASIS (Hitachi Software Engineering Co. Ltd.) or any of the other alignment programs listed above, including but not limited to ALIONment, SIM and GCG programs such as Gap, BestFit, FrameAlign and Compare. The amino acid residues that differ between the human and the non-human glycoprotein hormone can then be substituted using one of the above-mentioned techniques, and the resultant glycoprotein hormone assayed for its potency using one of the herein-mentioned assays.

The present invention also encompasses fragments of the analogs described herein that have either superagonist or antagonist activity. For example, fragments of the modified alpha chains of the invention may be used either alone or in combination with either a fragment or full length beta chain to create superagonist compounds. Likewise, fragments of the modified beta chains of the invention may be used either alone or in combination with either a fragment or full length alpha chain to create superagonist compounds. In some cases, fragments of the modified FSH molecules of the invention may also be used as antagonists, for instance, to limit the duration of activity of an FSH therapeutic after it has been administered.

The present invention also encompasses single chain analogs and chimeric proteins incorporating the mutated regions of the analogs described herein. For instance, the present inventors have found that incorporation of superpotency substitutions within the alpha subunit of dual-activity gonadotropins results in a 3-5 fold increase of both luteotropic and follitropic activities indicating that the intrinsic activities of dual-activity gonadotropins can be further enhanced by the combined substitutions of the present invention. Construction of dual-activity gonadotropins is described in U.S. Pat. No. 4,237,224, which is herein incorporated by reference in its entirety.

Characterization of FSH Superagonists

The effect of the modification or modifications to the wild-type FSH described herein can be ascertained in any number of ways. For example, cyclic AMP (cAMP) production in cells transfected with a nucleic acid encoding the modified glycoprotein can be measured and compared to the cAMP production of similar cells transfected with a nucleic acid encoding the wild-type glycoprotein hormone. Alternatively, progesterone production in cells transfected with the modified glycoprotein can be measured and compared to the progesterone production of similar cells transfected with the wild-type glycoprotein hormone. Alternatively, the activity of a modified glycoprotein hormone can be determined from receptor binding assays, from thymidine uptake assays, or from T4 secretion assays. Specific examples of such assays for determining the activity of modified glycoprotein hormones are set forth in the Example section contained herein. One skilled in the art can readily determine any appropriate assay to employ to determine the activity of either a wild-type or a modified glycoprotein hormone.

In one embodiment of the present invention, the modified glycoprotein hormone has a potency which is increased over the potency of the wild type glycoprotein hormone by at least about 10 fold. This increased potency can be assessed by any of the techniques mentioned above and described in the Example contained herein, or in any other appropriate assay as readily determined by one skilled in the art. The increased potency does not have to be consistent from assay to assay, or from cell line to cell line, as these of course, will vary. The modified FSH molecules of the invention may demonstrate an increase in potency of at least about 20 fold, 30 fold, 40 fold, 50 fold, 60 fold, 70 fold, 80 fold, 90 fold or even 100 fold over wild type using cell lines expressing responsive FSH receptors at varying levels.

In another embodiment of the present invention, the modified glycoprotein hormone has a maximal efficacy which is increased over the maximal efficacy of the wild type glycoprotein hormone by at least about 10%. This increased maximal efficacy can be assessed by any of the techniques mentioned above and described in the Example contained herein, or in any other appropriate assay as readily determined by one skilled in the art. The increased maximal efficacy does not have to be consistent from assay to assay, or from cell line to cell line, as these of course, will vary. The modified FSH molecules of the invention may demonstrate an increase in maximal efficacy of at least about 10% fold, at least about 20%, 30%, 40%, 50%, 60%, 70%, 80%, 90%, or 100%, over wild type using cell lines expressing responsive FSH receptors at varying levels.

Other assays suitable for characterizing the analogs described herein are described in PCT/US99/05908, which is herein incorporated by reference in its entirety. For instance, various immunoassays may be used including but not limited to competitive and non-competitive assay systems using techniques such as radioimmunoassays, ELISA, sandwich immunoassays, immunoradiometric assays, gel diffusion precipitin reactions, immunodiffusion assays, in situ immunoassays, western blots, precipitation reactions, agglutination assays, complement fixation assays, immunofluorescence assays, protein A assays, and immunoelectrophoresis assays, etc.

Improvements in the quality and quantity of oocytes can be assessed by in vitro and in vivo assays. It is common for improvements in oocyte quantity and quality to be determined using different end points of the in vitro fertilization process such as oocyte formation, oocyte fertilization, and blastocyst formation. In vitro fertilization experiments may follow a "superovulation protocol" in which subjects are treated with a superactive FSH analog according to the present invention, which leads to the release and maturation of multiple oocytes. In in vitro fertilization experiments, FSH (superactive FSH and recombinant wild type FSH) may be administered with hCG to trigger ovulation. A control animal may be used which receives only hCG or pregnant mare serum gonadotropin (PMSG).

The quality of oocytes can be improved by increasing the fertilization rate of oocytes in an animal. The fertilization rate of a superactive follicle stimulating hormone can be determined in vivo or in vitro by comparing the fertilization rate achieved with a superactive FSH to the fertilization rate achieved with the same amount of recombinant wild type FSH. A control animal may also be used that receives hCG.

The rate of fertilization can be measured by the percent of two-cell embryos which develop per total number of oocytes. If fertilization takes place in vitro, two cell embryos can be counted in fertilization dishes. In mice, two cell embryos develop approximately twenty-four hours after fertilization.

The fertilization rate varies based on the amount of superactive FSH administered. An animal may receive multiple does of superactiveFSH. The rate of fertilization increases by at least about 10 percent as a result of administration of superactive FSH at the maximally effective dose for oocyte number. The rate of fertilization may increase by at least about 20 percent, preferably at least 30 percent, 40%, 50%, 60%, 70%, 80%, 90%, or 100% as a result of administration of superactive FSH at the maximally effective dose for oocyte number.

Superactive follicle stimulating hormone can improve the quality of oocytes by improving the blastocyst formation rate per fertilized oocyte. The rate of blastocyst formation can be measured by determining the percentage of two-cell embryos which form blastocysts. The rate of blastocyst formation increases whether the blastocyst forms in vivo or in vitro. The blastocyst formation rate is dependent on the amount of superactive follicle stimulating hormone administered. The rate of blastocyst formation increases at least about 10 percent as a result of administration of a superactive follicle stimulating hormone at the maximally effective dose for oocyte number. The rate of blastocyst formation may increase at least about 20 percent, preferably at least 30%, 40%, 50%, 60%, 70%, 80%, 90%, or 100% as a result of administration of superactive FSH at the maximally effective dose for oocyte number.

Superactive follicle stimulating hormone can improve the quality of oocytes by increasing the total number of embryos per fertilized oocyte. The increase in total number of embryos per fertilized oocyte increases whether fertilization occurs in vivo or in vitro. The increase in total number of embryos per fertilized oocyte is dependent on the amount of superactive follicle stimulating hormone administered. The total number of embryos per fertilized oocyte increases at least about 10 percent as a result of administration of a superactive follicle stimulating hormone at the maximally effective dose for oocyte number. The total number of embryos per fertilized oocyte may increase by at least about 20 percent, preferably at least 30%, 40%, 50%, 60%, 70%, 80%, 90%, or 100% as a result of administration of superactive FSH at the maximally effective dose for oocyte number.

Superactive FSH can be used to improve the quality and quantity of oocytes from animals, including but not limited to, human, mouse, rat, primate, rabbit, pig, horse, sheep, and dog. Preferably, a superactive FSH is administered to a human FSH.

FSH Analogs with Increased Serum Half-Life

The modified FSH proteins of the invention may also be further modified such that the plasma half-life is increased as compared to wild type FSH. For instance, the modified FSH proteins of the invention may further comprise at least one sequence with a potential glycosylation site including sequences comprising N-glycosylation and/or O-glycosylation sites on either the alpha or beta chain. Sequences providing potential glycosylation recognition sites may be either an N-terminal or C-terminal extension on either the alpha or beta chain. Exemplary modified proteins contain an N-terminal extension on the a chain that is selected from the group consisting of ANITV (SEQ ID No. 3) and ANITVNITV (SEQ ID No. 4). Other exemplary modified proteins contain a further substitution in said β chain, wherein said substitution is selected from the group consisting of Y58N and V78N.

Increased half-life may also be provided by pegylation or conjugation of other appropriate chemical groups or by constructing fusion proteins having increased half life or any other method. Such methods are known in the art, for instance as described in U.S. Pat. Nos. 5,612,034, 6,225,449, and 6,555,660, each of which is incorporated by reference in its entirety. Half-life may also be increased by increasing the number of negatively charged residues within the molecule, for instance, the number of glutamate and/or aspartate residues. Such alteration may be accomplished by site directed mutagenesis, with preferred alterations selected from the group consisting of alpha subunit substitutions A85E and A85D, among others. Such alteration may also be achieved via an insertion of an amino acid sequence containing one or more negatively charged residues into said modified FSH, including insertions selected from the group consisting of GEFT (SEQ ID No. 5) and GEFTT (SEQ ID No. 6), among others. In one embodiment, the insertion is in the alpha subunit, and is selected from the group consisting of APD-GEFT-VQDC (SEQ ID No. 7) and APD-GEFTT-QDC (SEQ ID No. 8), among others.

The half-life of a protein is a measurement of protein stability and indicates the time necessary for a one-half reduction in the concentration of the protein. The serum half-life of the modified FSH molecules described herein may be determined by any method suitable for measuring FSH levels in samples from a subject over time, for example but not limited to, immunoassays using anti-FSH antibodies to measure FSH levels in serum samples taken over a period of time after administration of the modified FSH, or by detection of labeled FSH molecules, i.e., radiolabeled molecules, in samples taken from a subject after administration of the labeled FSH.

Expression and/or Synthesis of the FSH Superagonists

The present invention also includes nucleic acids encoding the modified FSH a and β subunits of the invention, as well as vectors and host cells for expressing the nucleic acids. Appropriate promoters for the expression of nucleic acids in different host cells are well known in the art, and are readily interchanged depending on the vector-host system used for expression. Exemplary vectors and host cells are described in U.S. Pat. No. 6,361,992, which is herein incorporated by reference in its entirety.

For instance, once a nucleic acid encoding a particular glycoprotein hormone of interest, or a region of that nucleic acid, is constructed, modified, or isolated, that nucleic acid can then be cloned into an appropriate vector, which can direct the in vivo or in vitro synthesis of that wild-type and/or modified glycoprotein hormone. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al., Molecular Cloning: A Laboratory Manual, 2nd ed. (1989)).

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella*, *Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., ".varies.-Factor-Directed Synthesis and Secretion of Mature Foreign Proteins in *Saccharomyces cerevisiae*." Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The FSH coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or beta.-galactosidase, which may be used to facilitate purification of the fusion protein by affinity chromatography. The insertion of protease cleavage sites to separate the components of the fusion protein is applicable to constructs used for expression in yeast. Efficient post-translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Exemplary expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted nucleic acids in mammalian cells (such as COS-7).

Expression of the gene or hybrid gene can be by either in vivo or in vitro. In vivo synthesis comprises transforming prokaryotic or eukaryotic cells that can serve as host cells for the vector. Alternatively, expression of the gene can occur in an in vitro expression system. For example, in vitro transcription systems are commercially available which are routinely used to synthesize relatively large amounts of mRNA. In such in vitro transcription systems, the nucleic acid encoding the glycoprotein hormone would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired glycoprotein hormone. (Stratagene Cloning Systems, La Jolla, Calif.).

Another method of producing a glycoprotein hormone is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a hybrid glycoprotein hormone can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a hybrid peptide. (Grant, G. A., "Synthetic Peptides: A User Guide," W. H. Freeman and Co., N.Y. (1992) and Bodansky, M. and Trost, B., Ed., "Principles of Peptide Synthesis," Springer-Verlag Inc., N.Y. (1993)). Alternatively, the peptide or polypeptide can by independently synthesized in vivo as described above. Once isolated, these independent peptides or polypeptides may be linked to form a glycoprotein hormone via similar peptide condensation reactions. For example, enzymatic or chemical ligation of cloned or synthetic peptide segments can allow relatively short peptide fragments to be joined to produce larger peptide fragments, polypeptides or whole protein domains (Abrahmsen, L., et al., Biochemistry, 30:4151 (1991); Dawson, et al., "Synthesis of Proteins by Native Chemical Ligation," Science, 266:776-779 (1994)).

The invention also provides fragments of modified glycoprotein hormones which have either superagonist or antagonist activity. The polypeptide fragments of the present invention can be recombinant proteins obtained by cloning nucleic acids encoding the polypeptide in an expression system capable of producing the polypeptide fragments thereof. For example, one can determine the active domain of a modified FSH protein which, together with the beta subunit, can interact with a glycoprotein hormone receptor and cause a biological effect associated with the glycoprotein hormone. In one example, amino acids found to not contribute to either the activity or the binding specificity or affinity of the glycoprotein hormone can be deleted without a loss in the respective activity.

For example, amino or carboxy-terminal amino acids can be sequentially removed from either the native or the modified glycoprotein hormone and the respective activity tested in one of many available assays described above. In another example, the modified proteins of the invention may have a portion of either amino terminal or carboxy terminal amino acids, or even an internal region of the hormone, replaced with a polypeptide fragment or other moiety, such as biotin, which can facilitate in the purification of the modified glycoprotein hormone. For example, a modified glycoprotein can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified glycoprotein can then be separated from the maltose binding region by cleaving the hybrid polypeptide with the specific protease factor Xa. (See, for example, New England Biolabs Product Catalog, 1996, pg. 164)

Active fragments of the FSH molecules of the invention can also be synthesized directly or obtained by chemical or mechanical disruption of larger glycoprotein hormone. An active fragment is defined as an amino acid sequence of at least about 5 consecutive amino acids derived from the naturally occurring amino acid sequence, which has the relevant activity, e.g., binding or regulatory activity. The fragments, whether attached to other sequences or not, can also include insertions, deletions, substitutions, or other selected modifications of particular regions or specific amino acids residues, provided the activity of the peptide is not significantly altered or impaired compared to the modified glycoprotein hormone. These modifications can provide for some additional property, such as to remove/add amino acids capable of disulfide bonding, to increase its bio-longevity, etc. In any case, the peptide must possess a bioactive property, such as binding activity, regulation of binding at the binding domain, etc. Functional or active regions of the glycoprotein hormone may be identified by mutagenesis of a specific region of the hormone, followed by expression and testing of the expressed polypeptide. Such methods are readily apparent to a skilled practitioner in the art and can include site-specific mutagenesis of the nucleic acid encoding the receptor. (Zoller, M. J. et al.).

The present invention also encompasses fusion proteins and chimeric proteins comprising the mutations described herein, including for instance, fusions to the CTEP domain of LH or CG proteins. Such a fusion protein may be made by ligating the appropriate nucleic acid sequences encoding the desired amino acid sequences to each other by methods known in the art, in the proper coding frame, and expressing the fusion protein by any of the means described above. Alternatively, such a fusion protein may be made by protein synthesis techniques, for example, using a peptide synthesizer. The single chain analogs and chimeric proteins of the invention may incorporate a peptide linker between the alpha and beta subunits, or between different portions of the chimeric protein.

Methods of Treatment

The modified FSH superagonists of the present invention may be used to treat any condition associated with glycoprotein hormone activity. Conditions "associated with glycoprotein hormone activity" are ones that are either completely or partially caused by altered glycoprotein hormone responsiveness, or ones that benefit from the administration of glycoprotein hormone. For instance, such conditions include, but are not limited to ovulatory dysfunction, luteal phase defects, unexplained infertility, male factor infertility, time-limited conception, low FSH receptor expression, low FSH receptor sensitivity, FSH receptor binding deficiencies, FSH receptor coupling deficiencies, low testosterone production, male pattern baldness, and pituitary failure or injury.

In particular, the quantity and quality of oocytes can be improved by administering a superactive FSH analog as described herein to an animal. For example, as reported herein, Applicants have surprisingly found that by administering a superactive FSH containing a modified alpha-subunit with basic amino acids at position 13, 14, 16 and 20, a dramatic increase in the quantity and quality of oocytes is obtained. The effects of a superactive FSH on oocyte quantity and quality may be further enhanced by increasing the FSH serum half-life of the superactive FSH. The FSH serum half-life can be increased by further modifying the superactive FSH. Further modifications, including but not limited to those previously described, can be used to increase FSH serum half-life. For instance, an ANITV (SEQ ID No. 3) extension may be used to prolong FSH serum half-life.

According to U.S. Pat. No. 5,574,011, herein incorporated by reference in its entirety, FSH stimulates the gonads to produce steroids, such as testosterone. Accordingly, the FSH analogs of the invention could be used to treat any condition associated with low steroid production, and particularly low testosterone production. According to U.S. Pat. No. 6,562,790, herein incorporated by reference, coronary artery blockage is treatable with testosterone. Therefore, the analogs of the present invention may be used to elevate testosterone levels in patients exhibiting coronary artery disease.

The analogs of the present invention may also be used in therapeutic regimens of assisted reproduction in either a male or female subject comprising administering an assisting amount of the modified FSH to the subject. In such methods, the analogs may be administered alone or in combination with other therapeutics, for instance, including but not limited to Clomiphene citrate, GnRH (gonotropin releasing hormone) and LH (Luteinizing hormone). For example, in a subject with isolated gonadotropin deficiency (IGD), administration of modified FSH and LH may be administered to the subject to restore normal gonadal function. It is widely known in the art that glycoprotein hormones such as FSH and LH are integral in female reproductive physiology, and these glycoprotein hormones may be administered to a subject to overcome a number of reproductive disorders and thereby assist reproduction.

The analogs of the invention are particularly useful for treating women prone to ovarian hyperstimulation, for instance by using analogs having different serum half-lives in a combined regimen. Such methods may include (a) administering an assisting amount of a first modified FSH according to the invention wherein the plasma half-life of said first modified FSH is increased as compared to wild type FSH, and (b) subsequently administering an assisting amount of a second modified FSH according to the invention wherein the plasma half-life of said second modified FSH is decreased as compared to said first modified FSH. For instance, analogs demonstrating decreased half-life as compared to wild-type FSH, i.e. TR-4401, may be useful for treating women prone to ovarian hyperstimulation.

A skilled practitioner in the art can readily determine the effective amount of the glycoprotein hormone to administer and will depend on factors such as weight, size, the severity of the specific condition, and the type of subject itself. The therapeutically effective amount can readily be determined by routine optimization procedures. The present invention provides glycoprotein hormones with increased potency relative to the wild-type glycoprotein hormone. These modified glycoprotein hormones will allow a skilled practitioner to administer a lower dose of a modified glycoprotein hormone relative to the wild-type glycoprotein hormones to achieve a similar therapeutic effect, or alternatively, administer a dose of the modified glycoprotein hormone similar to the dose of the wild-type glycoprotein hormone to achieve an increased therapeutic effect.

Depending on whether the glycoprotein hormone is administered orally, parenterally, or otherwise, the administration of the prostaglandin can be in the form of solid, semi-solid, or liquid dosage forms, such as, for example, tablets, pills, capsules, powders, liquids, creams, and suspensions, or the like, preferably in unit dosage form suitable for delivery of a precise dosage. The glycoprotein hormone may include an effective amount of the selected glycoprotein hormone in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected glycoprotein hormone without causing unacceptable biological effects or interacting in an unacceptable manner with the glycoprotein hormone.

Actual methods of preparing such dosage forms are known, or will be apparent, to those skilled in this art; for example, see Remington's Pharmaceutical Sciences, latest edition (Mack Publishing Co., Easton, Pa.).

Genetic therapy is another approach for treating hormone disorders with the modified glycoprotein hormones of the present invention. In this approach, a gene encoding the modified glycoprotein hormone can be introduced into a cell, such as a germ line cell or a somatic cell, so that the gene is expressed in the cell and subsequent generations of those cells are capable of expressing the introduced gene. For example, a nucleic acid encoding a modified FSH protein of the invention can be inserted into an ovarian cell, or its precursor, to enhance ovulation. Suitable vectors to deliver the coding sequence are well known in the art. For example, the vector could be viral, such as adenoviral, adenoassociated virus, retrovirus, or non-viral, such as cationic liposomes.

The analogs of the present invention have an enhanced activity over wild type protein and are therefore particularly suitable for delivering agents to cells expressing glycoprotein hormone receptors. Accordingly, the present invention further provides a method of delivering an agent to a cell expressing a glycoprotein receptor in a subject in need thereof using the modified glycoprotein hormones of the invention. The method of delivering an agent to a cell (i.e. targeted delivery) can employ any suitable agent, depending on the nature of the subject's illness or suspected illness. The agent can be a cytoprotective compound, antibody, drug, sensitizer, biological response modifier, radionuclide, toxin or combination thereof.

In certain embodiments, the methods of targeted delivery are for the treatment of a subject with a disorder or suspected disorder associated with abnormal glycoprotein receptor expression. In certain embodiments, the methods of targeted delivery are for the diagnosis or detection of a disorder associated with abnormal glycoprotein receptor expression. In certain embodiments, the methods of targeted delivery can be used in conjunction with other therapies, diagnostic procedures or clinical modalities, including radiation and/or surgery.

In one embodiment, the methods provide for targeted delivery of an agent, wherein the agent is a cytoprotective compound. Cytoprotective compounds are those compounds which act to protect or decrease the incidence or severity of injury to a cell. Commercially available cytoprotective compounds include mesna (MESNEX®, Bristol-Myers Squibb), amifostine (ETHYOL®, Alza), dexrazoxane (ZINECARD®, Pharmacia & Upjohn) and leucovorin (multiple manufacturers).

In one embodiment, the agent can be any drug used to treat various forms of cancer, such as, for example, natural or synthetic estrogens, estrogen receptor modulators, progestins, androgens, gonadotropin-releasing hormones, androgen inhibitors, bisphosphonates, glucocorticoids, thyroid hormones, antithyroid agents, iodine agents, bromocriptine, alkylating agents, antimetabolites, antimitotic agents, epipodophyllotoxins, antineoplastic antibiotics, antineoplastic hormones, platinum coordination complex agents, anthracenediones, substituted ureas, methylhydrazine derivatives, DNA topoisomerase inhibitors, retinoids, porfimer, mitotane or combinations thereof.

In one embodiment, the agent can be any drug used to treat cancers of the male or female reproductive systems (e.g. endometrial cancer, uterine cancer, cervical cancer, breast cancer, testicular cancer). In a preferred embodiment, the agent can be clomiphene, finasteride, propylthiouracil, methimazole, bleomycin, vincristine, vinblastine, cisplatin, mitomycin, ifosfamide, cyclophosphamide, doxorubicin, paclitaxel, fluorouracil, carboplatin, epirubicin, altretamine, vinorelbine, mitoxantrone, prednisone or combinations thereof.

Drugs known to enhance the cytotoxic effect of certain anti-cancer drugs and radiopharmaceuticals can also be used. Such drugs are commonly referred to as sensitizers. Examples of sensitizers which enhance the activity of various therapeutic drugs (e.g., anti-cancer drugs) are buthionine sulfoximine and calcium channel blockers such as verapamil, and diltiazem. (See, U.S. Pat. No. 4,628,047 and Important Advances in Oncology 1986, DeVita, et al., Eds., J. B. Lippincott Co., Philadelphia, pages 146-157 (1986), incorporated herein by reference in their entireties.) Other sensitizers known in the art are metronidazole, misonidazole, certain 2-sulfamyl-6-nitrobenzoic acid derivatives, 2,6-disubstituted derivatives of 3-nitropyrazine, and certain isoindoledione compounds. (See, U.S. Pat. Nos. 4,647,588; 4,654,369; 4,609,659 and 4,494,547, incorporated herein by reference in their entireties.)

In certain embodiments, the agent can be a biological response modifier. Any biological response modifier can be used in the scope of the invention. Examples of biological response modifiers useful in the methods of the invention include, but are not limited to interferon-α, interferon-β, interferon-γ, tumor necrosis factor, lymphotoxin, interleukin-1, interleukin-2, interleukin-3, interleukin-4, interleukin-5, interleukin-6 or combinations thereof.

In certain embodiments, the agent can be an antibody. The antibody can be a monoclonal or polyclonal antibody. In certain embodiments, the antibodies can be humanized antibodies, chimeric antibodies, or functional antibody fragments including, for example, Fab1, Fab2, etc.

Examples of toxins which can be employed in the methods of the invention are ricin, abrin, diphtheria toxin, *Pseudomonas* exotoxin A, ribosomal inactivating proteins, and mycotoxins; e.g., trichothecenes. Trichothecenes are a species of mycotoxins produced by soil fungi of the class fungi imperfecti or isolated from Baccharus megapotamica (Bamburg, Proc. Molec. Subcell Bio. 1983, 8:41-110, Jarvis and Mazzola, Acc. Chem. Res. 1982, 15:338-395, incorporated herein by reference in their entireties.) Therapeutically effective modified toxins or fragments thereof, such as those produced through genetic engineering or protein engineering techniques, can be used.

Any means of coupling or linking an agent to a modified glycoprotein hormone can be employed. For example a number of different cleavable linkers have been described previously. See, U.S. Pat. Nos. 4,618,492; 4,542,225; and 4,625,014, incorporated herein by reference in their entireties. The mechanisms for release of an agent from these linker groups include by irradiation of a photolabile bond, and acid-catalyzed hydrolysis. U.S. Pat. No. 5,563,250, incorporated herein by reference in its entirety, discloses immunoconjugates comprising linkers of specified chemical structure, wherein the linkage is cleaved in vivo, releasing the compound (radiopharmaceutical, drug, toxin, etc.) in its native form. The linker is susceptible to cleavage at mildly acidic pH, and is believed to be cleaved during transport into the cytoplasm of a target cell, thereby releasing the biologically active compound inside a target cell. U.S. Pat. No. 4,671,958, incorporated herein by reference in its entirety, includes a description of immunoconjugates comprising linkers which are cleaved at the target site in vivo by the proteolytic enzymes of the patient's complement system.

Other means of coupling or linking have been described. For example, linker molecules are commercially available, such as those available from Pierce Chemical Company, Rockford, Ill. (See the Pierce 1986-87 General Catalog, pages 313-354, incorporated herein by reference in its entirety.) Means for coupling to an antibody, (See, for example, U.S. Pat. Nos. 4,671,958 and 4,659,839, incorporated herein by reference in their entireties) and means of linking or coupling radionuclide metal chelates, toxins and drugs to proteins are known. See, for example, European Patent Application Publication No. 188,256; U.S. Pat. Nos. 4,671,958; 4,659,839, 4,414,148; 4,699,784; 4,680,338; 4,569,789; and 4,590,071; Borlinghaus et al. Canc. Res. 47:4071-4075, Aug. 1, 1987, Foran, Best Pract. Res. Clin. Haematol. 2002, 15(3): 449-65 and Fotiou, et al., Eur. J. Gynaecol. Oncol. 1988, 9(4): 304-7 incorporated herein by reference in their entireties. In view of the large number of methods that have been reported for coupling a variety of radiodiagnostic compounds, radiopharmaceuticals, drugs, toxins, and other agents to proteins, one skilled in the art will be able to determine a suitable method for attaching a given agent to a modified glycoprotein.

Methods of Imaging

The analogs of the present invention have an enhanced activity over wild type protein and are therefore particularly suitable for imaging cells expressing glycoprotein hormone receptors. Accordingly, in one embodiment, the invention further provides methods of imaging cells comprising a glycoprotein hormone receptor using the modified glycoprotein hormones of the present invention. The method of imaging and detecting the hormone can be any method known to those of skill in the art. Commonly used imaging methods include, for example, magnetic resonance imaging (MRI), X-ray, computed tomography (CT), positron emission tomography (PET), mammography and ultrasound.

Methods of imaging subjects using basic radiologic techniques have been described, for example, "Textbook of Radiology and Imaging," Sutton and Livingstone, 7th Edition, (2 Volume set), Churchill Livingstone (Elsevier Sciences), London, 2002, "A Concise Textbook of Radiology," Armstrong and Wastie (eds.) Arnold Publishing (The Thomson Corporation), Scarborough, Ontario, Canada, 2001, "Walter & Miller's Textbook of Radiotherapy," Bomford and Knuckler, 6th Edition, Churchill Livingstone (Elsevier Sciences), London, 2001, incorporated herein by reference in their entireties. See also, Bottomley, Comput. Radiol. 1984, 8(2): 57-77, Dixon, Radiology 1984, 153(1):189-94, Daley and Cohen, Cancer Res. 1989, 49(4):770-9, Ellis, et al., Clin. Radiol. 2001, 56(9):691-9, Paushter, et al., Med. Clin. North Am. 1984, 68(6):1393-421, Blecher, Aust. Fam. Physician 1983 12(6):449-50, 452, Bragg, Cancer 1977, 40(1 Suppl):500-8, Moseley, Br. Med. J. (Clin. Res. Ed.) 1982, 284(6323):1141-4, Lentle and Aldrich, Lancet 1997, 350(9073):280-5, Weber, et al., Strahlenther Onkol. 1999, 75(8):356-73, Hanbidge, Can. J. Gastroenterol. 2002, 16(2):101-5, Miles, Eur. Radiol. 2003, Suppl 5:M134-8, Prigent-Le Jeune, et al., Eur. J. Nucl. Med. Mol. Imaging. 2004, February 19 [Epub ahead of print], DeSimone, et al., Gynecol. Oncol. 2003, 89(3):543-8 and Goldenberg, et al., J. Clin. Oncol. 1987, 5(11):1827-35, incorporated herein by reference in their entireties.

Any suitable means of imaging or detecting can be employed, depending, inter alia, on the nature of the subject's disorder or suspected disorder, the tissue to be imaged and whether functional (physiologic) or structural (anatomic) images are desired. In some embodiments, among others, the methods of imaging provide that detecting an amount of a labeled modified glycoprotein hormone in a subject or detecting increased levels of a modified glycoprotein hormone in a subject indicates the presence of an autoimmune disorder or a cancerous disorder selected from the group consisting of ovarian cancer, uterine cancer, cervical cancer, endometrial cancer, breast cancer, testicular cancer or pituitary tumor.

Imaging methods can be broadly categorized as those that provide information regarding the structure or anatomy of a subject or those that provide function or physiology of a subject. Structural imaging provides the shape of a bone or tissue component to determine if there are abnormal formations or destruction of certain elements. Tumors or the presence of cancerous cells can appear as structural changes. A newer type of structural imaging provides the chemical composition of different parts of a tissue in order to determine if there is ongoing injury or abnormal biochemical processes (e.g. presence or growth of cancerous cells). See, for example, Bonilha, et al., Med. Sci. Monit. 2004, 10(3):RA40-6, epub 2004 Mar. 1, Ballmaier, et al., Psychiatry Res. 2004, 15; 130(1):43-55, Ballmaier, et al., Biol. Psychiatry, 2004, 55(4): 382-9, Cha, Magn. Reson. Imaging Clin. N. Am. 2003, 11(3): 403-13 and Kopelman, et al., Hippocampus, 2003; 13(8): 879-91, incorporated herein by reference in their entireties.

Functional imaging is a relatively new technique which seeks to ascertain whether particular tissues or organs are performing particular functional tasks. This technique can capitalize on a number of physiologic processes, including, for example, blood flow and activity-associated with changes in blood flow (i.e. neoplastic presence or growth) and monitoring responses to chemotherapy. See, for example, Takeuchi, et al., J. Med. Invest. 2004, 51(1-2):59-62, Otsuka, et al., J. Med. Invest. 2004, 51(1-2):14-9, Martincich, et al., Breast Cancer Res. Treat. 2004, 83(1):67-76, Cohen and Goadsby, Curr. Neurol. Neurosci. Rep. 2004, 4(2):105-10 and Lewis, et al., Eur. J. Neurosci. 2004, 19(3):755-60, incorporated herein by reference in their entireties.

In general, radiological methods such as, for example, magnetic resonance imaging (MRI), X-ray, computed tomography (CT), mammography and ultrasound provide structural or anatomic information regarding a subject. Radiological methods such as, for example, nuclear medicine, radionuclide imaging and positron emission tomography (PET) provide functional or physiologic information regarding a subject. Both structural and functional imaging are within the scope of the present invention.

In one embodiment of the invention, the imaging methods provide that the modified glycoprotein hormone is labeled (i.e. a contrast agent is used). Any label or contrast agent can be used. See, Minato, et al. J. Comput. Assist. Tomogr. 2004, 28(1):46-51, Antoch, et al., JAMA 2003, 290(24):3199-206, Brinker, Rev. Cardiovasc. Med. 2003; 4 Suppl 5:S19-27, el-Diasty, et al., J. Urol. 2004, 171(1):31-4, Williams, et al., Int. J. Oral Maxillofac. Surg. 2003, 32(6):651-2, Follen, et al., Cancer 2003, 98(9 Suppl):2028-38, Behrenbruch, et al., Med. Image Anal. 2003, 7(3):311-40, Knopp, et al., Mol. Cancer. Ther. 2003, 2(4):419-26, incorporated herein by reference in their entireties. The label can be any label known to those of skill in the art. In one embodiment, the label can be a radiopaque label, radioactive label, fluorescence label or paramagnetic label.

Radionuclides generally emit either beta ($\beta$) or gamma ($\gamma$) radiation. I131 emits about 90% $\beta$-radiation and about 10% $\gamma$-particles has a physical half life of about 8 days. Tc99m emits $\gamma$-radiation and has a half life of about 6 hours. Following administration of, for example, a Tc99m-labeled protein, the biodistribution of the radionuclide can be detected by scanning the patient with a gamma camera using known procedures. Accumulations of Tc99m at the target site(s) is thus easily imaged. See, Toohey, Radiographics. 2000; 20:533-546, Kostakoglu, et al., RadioGraphics 2003, 23:315-340, Saremi, et al., RadioGraphics 2002, 22:477-490, Intenzo, et al., RadioGraphics 2001, 21:957-964, Ranger, RadioGraphics 1999, 19:481-502, Simpkin, RadioGraphics 1999, 19:155-167, Janoki and Kerekes, Acta Physiol. Hung. 1992, 79(2):183-96, Hoefnagel, Anticancer Drugs 1991, 2(2):107-32, Hoefnagel, Eur. J. Nucl. Med. 1991, 18(6):408-31, Gatley, et al., Acta Radiol. Suppl. 1990, 374:7-11, Ott, Br. J. Radiol. 1989, 62(737):421-32, Andersen, Cerebrovasc. Brain Metab. Rev. 1989, 1(4):288-318 and Miraldi, Int. J. Radiat. Oncol. Biol. Phys. 1986, 12(7):1033-9, incorporated herein by reference in their entireties.

In addition to I131 or Tc99m, any radioisotope known to those of skill in the art can be employed in the methods of the invention. Other radionuclides and chelates can include, for example, Co57, Co58, Cr51, F18 FDG, Ga67, In111 chloride, In111 pentetate (DTPA), In111oxyquinoline (oxine), In111 Capromab pendetide, In111 Imciroma pentetate, In111, pentetreotide, In111 satumomab pendetide, I123, I125 iothalamate, I125 human serum albumin (RISA), I131 iodohippurate, I131 iodomethylnorcholesterol (NP-59), I131 metaiodobenzylguanidine (MIBG), Kr81m gas, P32 chromic phosphate, P32 sodium phosphate, Ru82, Sm 153 lexidronam (Sm-153 EDTMP), Sr89, Tl 201 and Xe133.

Diagnostic Assays

The present invention further provides for the detection of analytes that interfere with the binding of the modified glycoprotein hormones of the invention to a glycoprotein hormone receptor. In one embodiment, the methods provide for the detection of an analyte that interferes with the binding of a modified glycoprotein hormone receptor in a biological sample, said method comprising (I) contacting the sample with a modified glycoprotein hormone according to the present invention and (ii) detecting a signal wherein the presence or amount of the signal detected indicates the presence or absence of an analyte that interferes with the binding of a modified glycoprotein hormone to a glycoprotein receptor.

In one embodiment, the method for the detection of an analyte is a competitive binding assay. A competitive binding assay is an assay based on the competition between a labeled and an unlabelled ligand in the reaction with a receptor binding agent (e.g. antibody, receptor, transport protein). IUPAC Compendium of Chemical Terminology, 1997, 2nd edition, "Competitive Protein Binding Assays" Odell and Daughaday, W. H. Lippincott, 1972 and "Principles of Competitive Protein-binding Assays" Odell and Franchimont, P. John Wiley & Sons Inc., 1983, incorporated herein by reference in their entireties. See also, U.S. Pat. No. 6,537,1760, incorporated herein by reference in its entirety.

In certain embodiments, the signal is the presence or amount of the modified glycoprotein hormone bound with the glycoprotein receptor in the sample. In certain embodiments, the method employs the detection of a secondary signal, such as, for example, the detection of the presence or amount of cAMP or a steroid (e.g. progesterone). In certain embodiments, the methods employ the use of whole cells in the biological sample. In certain embodiments, the methods employ only parts of cells, for example, cell membranes.

In certain embodiments, the assay can be performed in solution. In certain embodiments, one or more components of the assay can be immobilized on a solid phase. Plastic surfaces, microparticles, magnetic particles, filters, polymer gel materials and other solid-phase substrates can be used as solid phases. See, for example, U.S. Pat. Nos. 6,664,114; 6,589, 798; 6,479,296 and 6,294,342, incorporated herein by reference in their entireties. It is possible to automate the methods of assay provided in the invention.

Methods of Designing Glycoprotein Receptor Agonists and Antagonists Using FSH Superagonists The present invention also provides methods of designing new receptor agonists and antagonists based on the interaction of the FSH proteins of the invention and a cognate receptor. Such methods involve predicting interactions of charge motifs in the FSH proteins of the invention with complementary amino acid residues within a cognate receptor. For instance, such a method may involve comparing the differences in interaction in terms of binding and bioactivity of FSH to receptors from evolutionary distant species, e.g., human LH versus rat LH receptor, localizing charged amino acids within extracellular domains and/or extracellular loops that are present in only one of the two receptor sequences, performing alanine scanning and charge reversal mutagenesis to further validate given prediction, building a model of hormone-receptor complex incorporating validated interactions, and designing new hormone analogs and receptor antagonists using the model. New hormone analogs include those that are predicted to bind to the receptor using the model. New antagonists include those that are designed from the domains and/or loop of the receptor protein that are predicted to bind to the FSH analog using the model.

For example, one of the analogs of the invention (TR-4402, comprising the substitutions alpha(E14R+Q20R+G73R)+betaE4R), has been found to interact with the rat LH receptor (SEQ ID No. 23, NCBI Accession No. NP_037110) at high concentrations, but not the human LH receptor (SEQ ID No. 24, NCBI Accession No. NP_000224, data not shown). Based on the difference in specificity of TR-4402 at these receptors, Arg14, Arg20 and Arg73 should interact with negatively charged residues Asp and Glu in the rat LH receptor. The negatively charged residues present in the rat receptor but absent in the human receptor are Asp 312 and Glu 314 (based on the human LH receptor amino acid sequence with signal peptide) (Ser and Lys, respectively, in the human LH receptor). The corresponding residues in the human FSH receptor (SEQ ID No. 22, NCBI Accession No. AAA52477) are Glu316, Asp317 and Glu319. This cluster of acidic amino acids, therefore, is predicted to interact with Arg14, Arg20 and Arg73 of the alpha subunit of TR-4402. This information should allow for better modeling of glycoprotein hormone interactions, and will contribute to the design of new glycoprotein analogs, including peptide/protein antagonists containing the sequence corresponding to 298-338 of the human FSH receptor and including Glu300 and Asp302.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Production and Characterization of FSH Superagonists

Site Directed Mutagenesis. Site directed mutagenesis of human alpha (SEQ ID No. 1) and FSH beta (SEQ ID No. 2) subunit cDNA was performed using QuickChange Mutagenesis Kit from Stratagene. Analogs were designed according to the methods described in U.S. Pat. No. 6,361,992, herein incorporated by reference in its entirety.

After subcloning into the expression vectors, the entire PCR products of all constructs were sequenced to verify the mutations and to rule out any undesired polymerase errors.

Transient Expression. Analogs were expressed transiently in Chinese hamster ovary (CHO-K1) cells. Cells were transiently co-transfected in 60 or 100 min culture dishes with wild-type or mutant subunit cDNAs (alpha and FSH beta), using a transient transfection protocol based on a liposome formulation (LipofectAMINE reagent, Gibco BRL). After recovery for 12 hours in regular growth medium, transfected cells were cultured in CHO-serum free medium (CHO-SFM, Gibco BRL) for 72 hours. Subsequently, the conditioned media including control medium from mock transfections using the expression plasmids without gene inserts, were harvested, concentrated with Centriprep 10 concentrators (Amicon, Beverly, Mass.) and stored at −70° C. Analogs were quantitated with a panel of different monoclonal and polyclonal antibodies recognizing different FSH epitopes.

FSH Bioactivity Assay. The follitropic activity of the analogs was assessed by their ability to induce cAMP production in CHO cells expressing hFSH receptors. CHO cells stably expressing the hFSH receptor were grown to confluence in 96-well tissue culture plates. Subsequently, cells were incubated either in salt-free conditions (2 h) or with physiological media (1 h) at 37° C., 5% CO2 with serial dilutions of wild-type and mutant FSH as well as control medium from mock transfections. The amount of cAMP produced was determined by radioimmunoassay.

Figure 2:
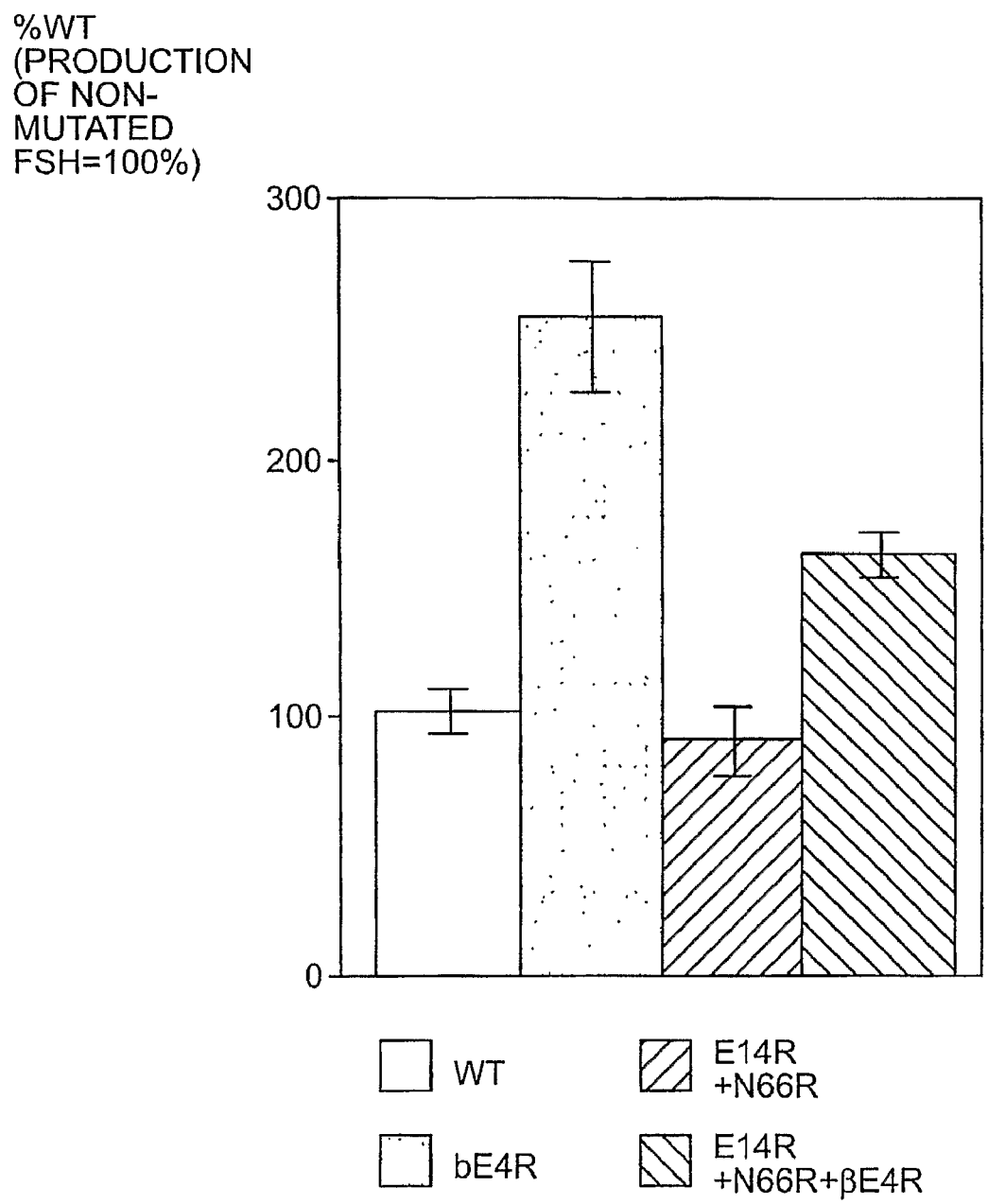
FIG. 2 is a graph showing the effect of the beta E4R mutation on hFSH production in transfected CHO-FSHR cells.
Figure 3A:
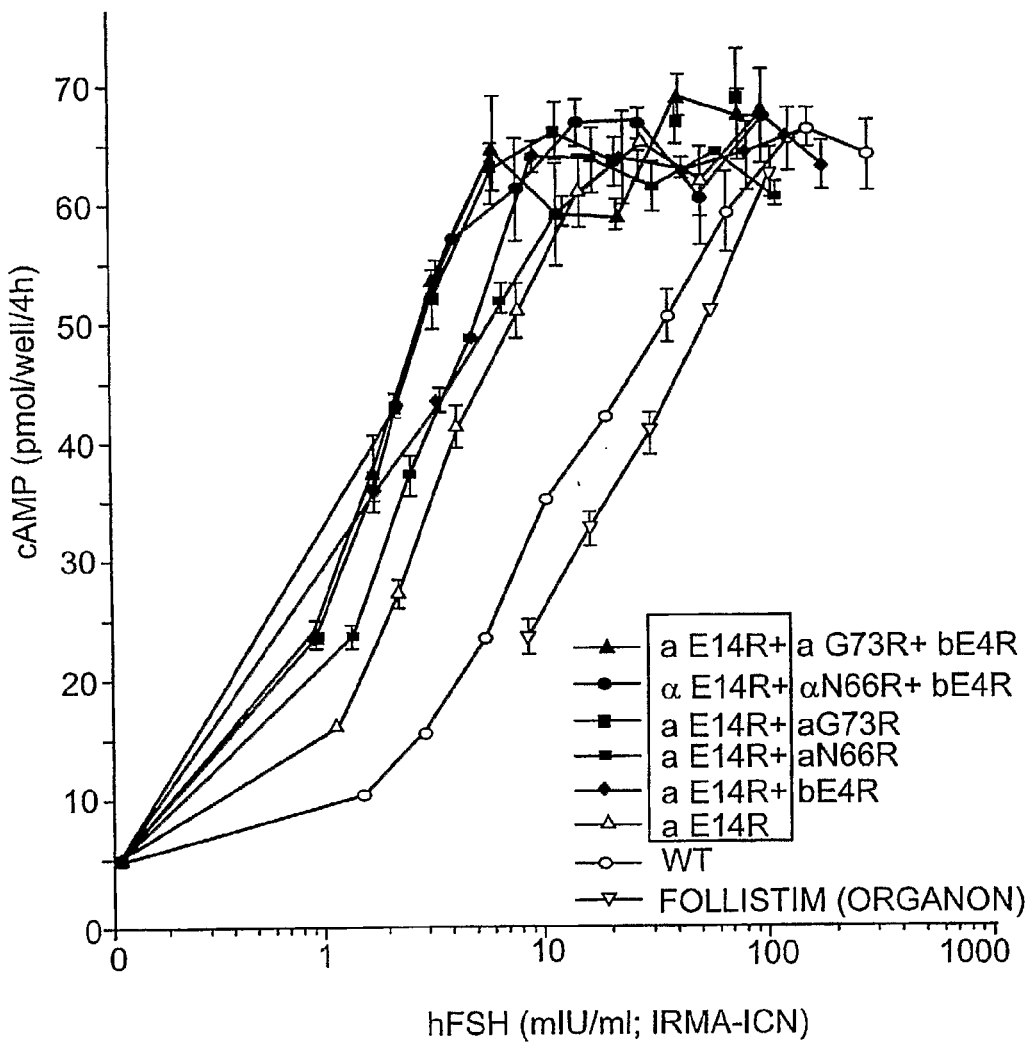
Figure 4A:
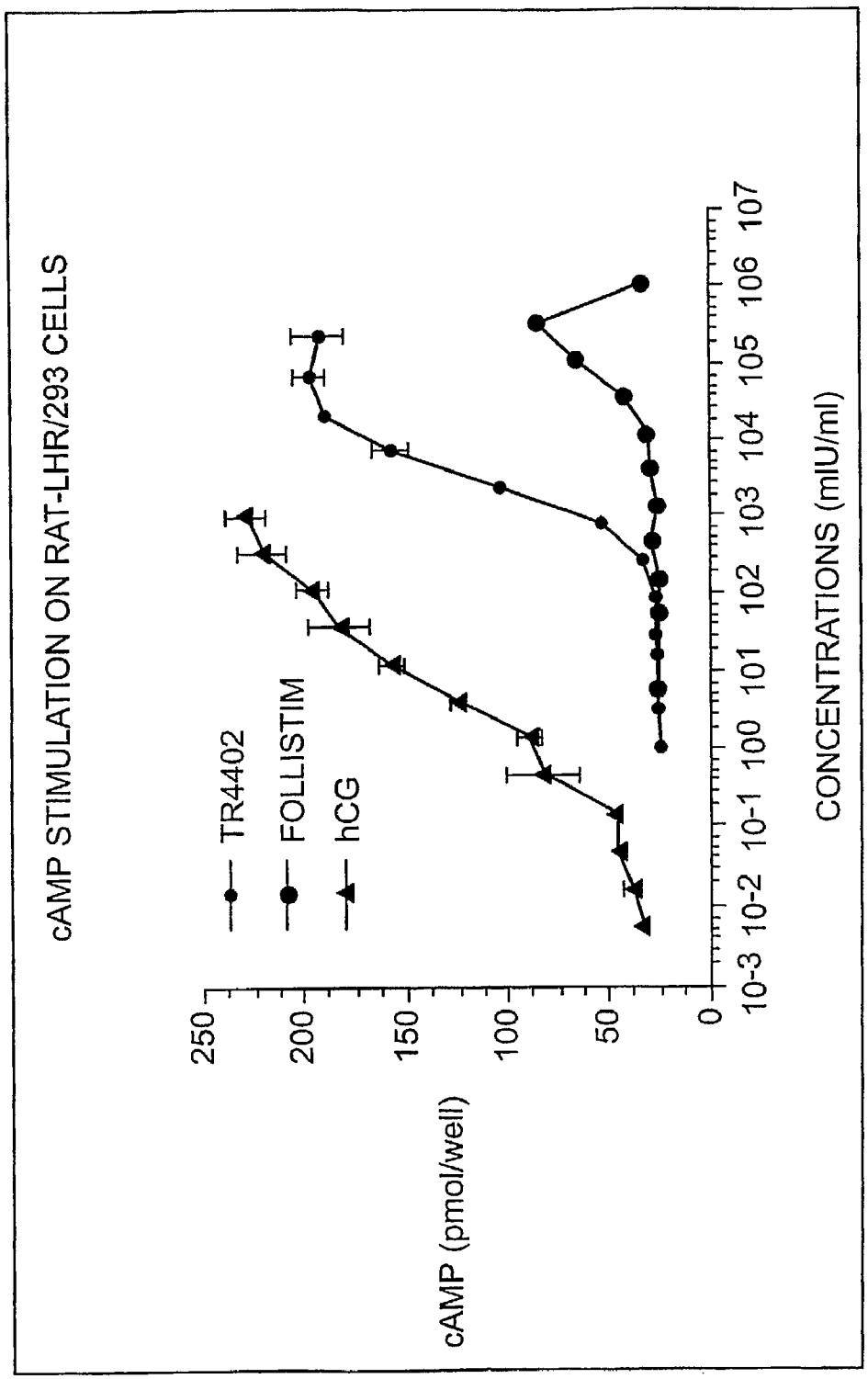
FIGS. 4A and B are graphs showing a comparison of cross-reactivity of rat and human LHR to analog FSH and wild type FSH.
Figure 4B:
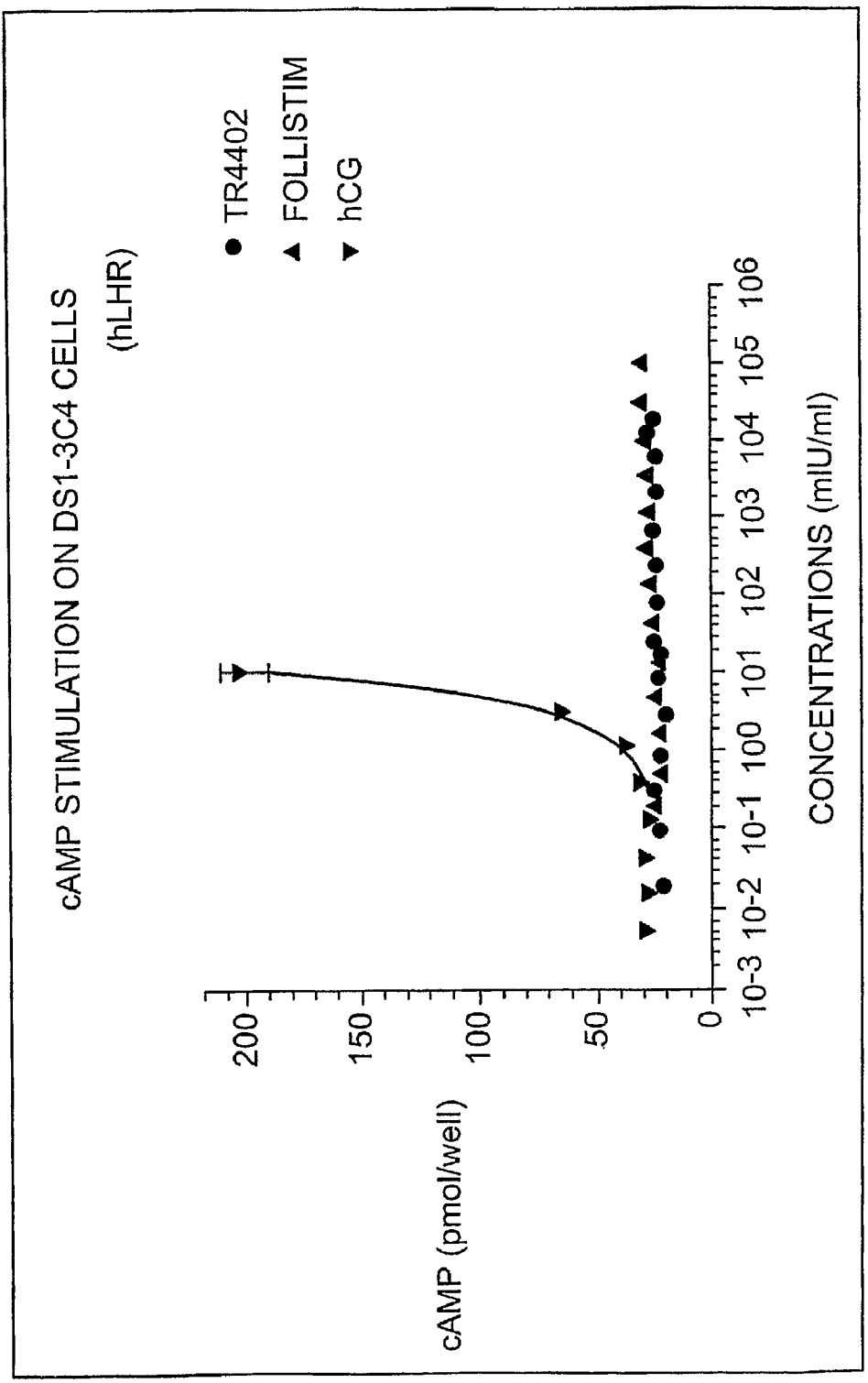
FIG. 4B shows that there is no cross-reactivity between FSH TR-4402 and human luteinizing hormone.
Figure 5:
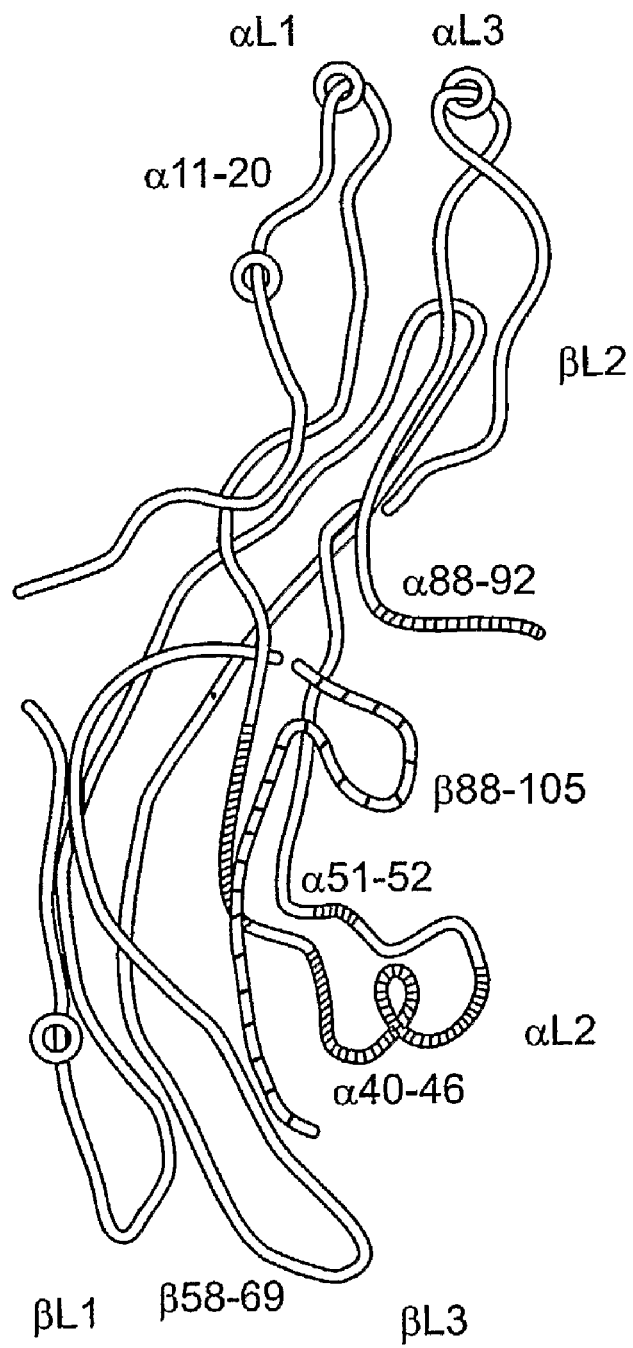
FIG. 5 is a diagram of the structure of FSH showing the loops in the alpha and beta subunits.
Figure 6A:
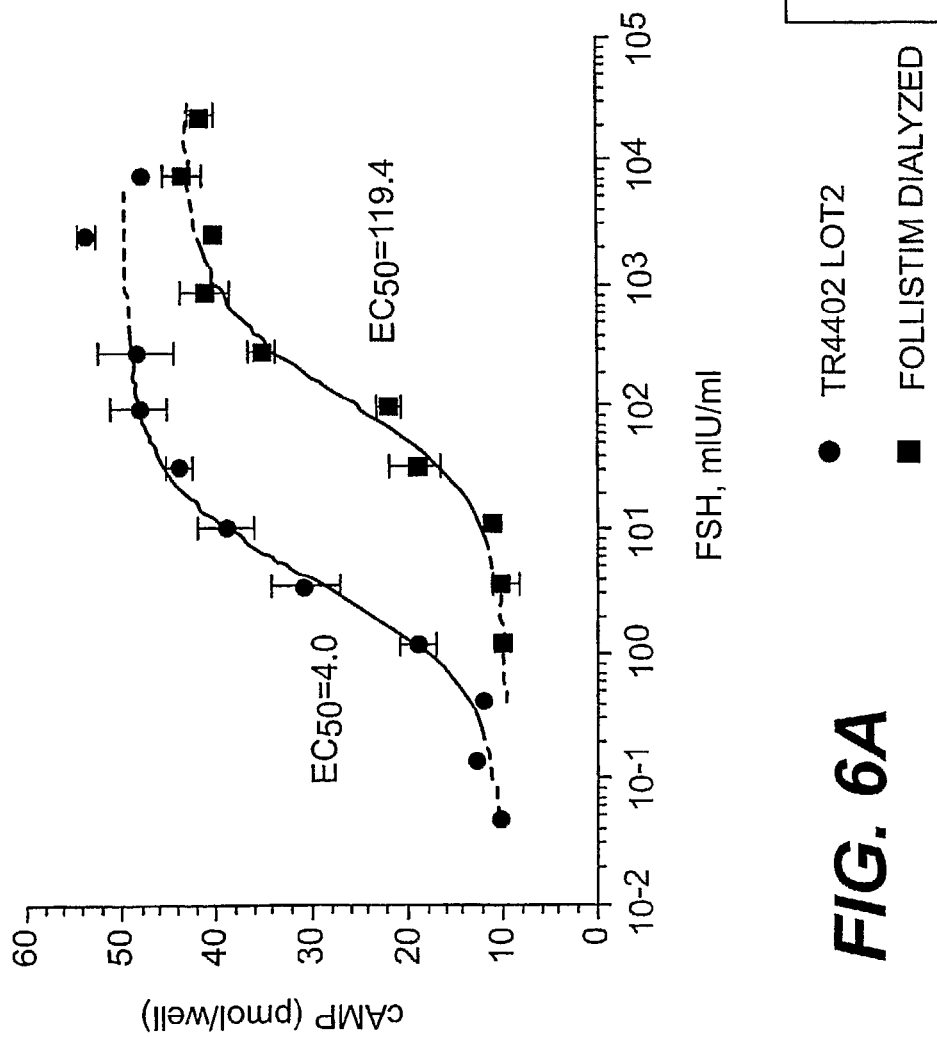
FIGS. 6A and B are graphs showing cAMP production in CHO cells in response to purified analog TR-4402 versus wild type FSH and purified analog TR-4401 versus wild type FSH, respectively.
Figure 6B:
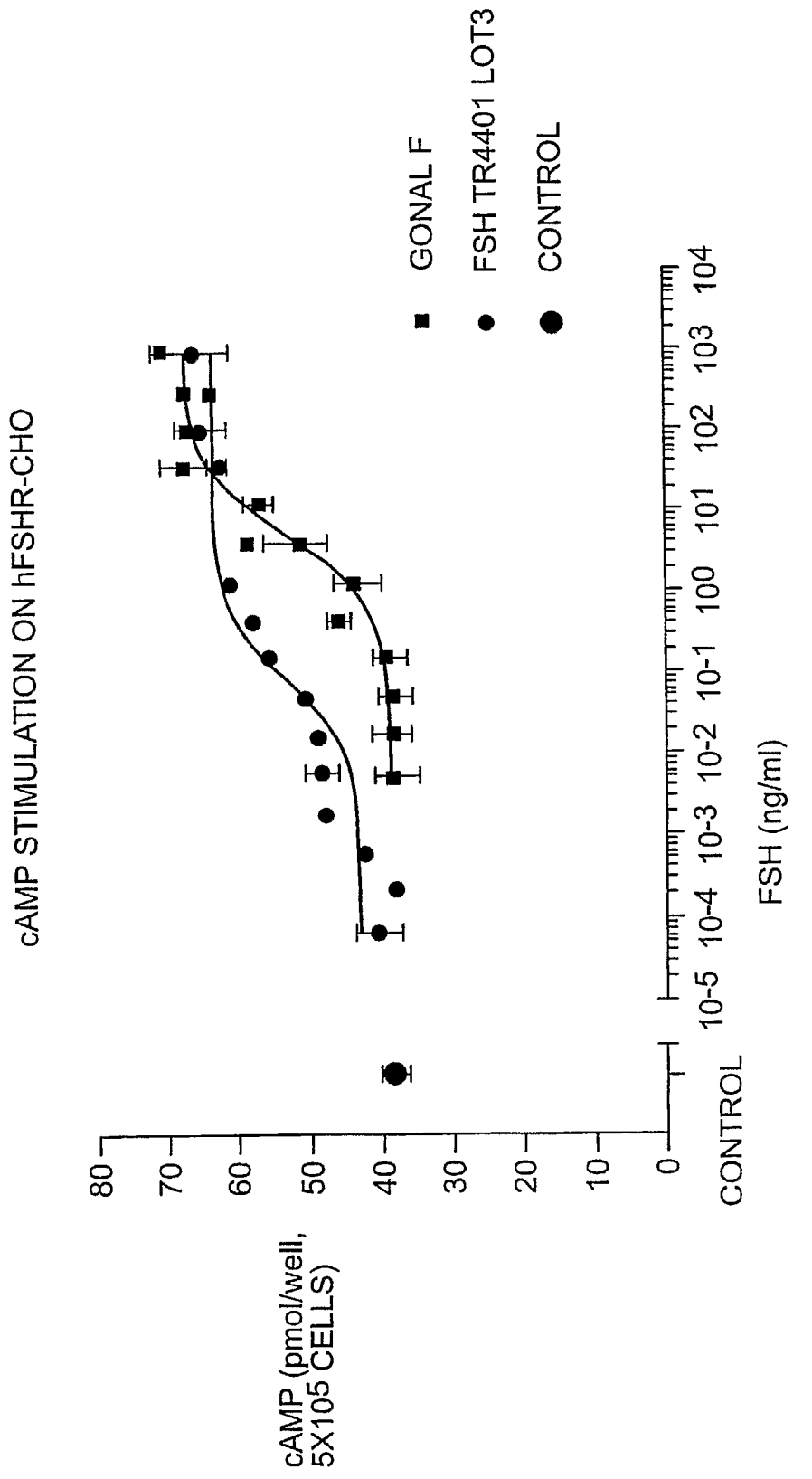
Figure 7:
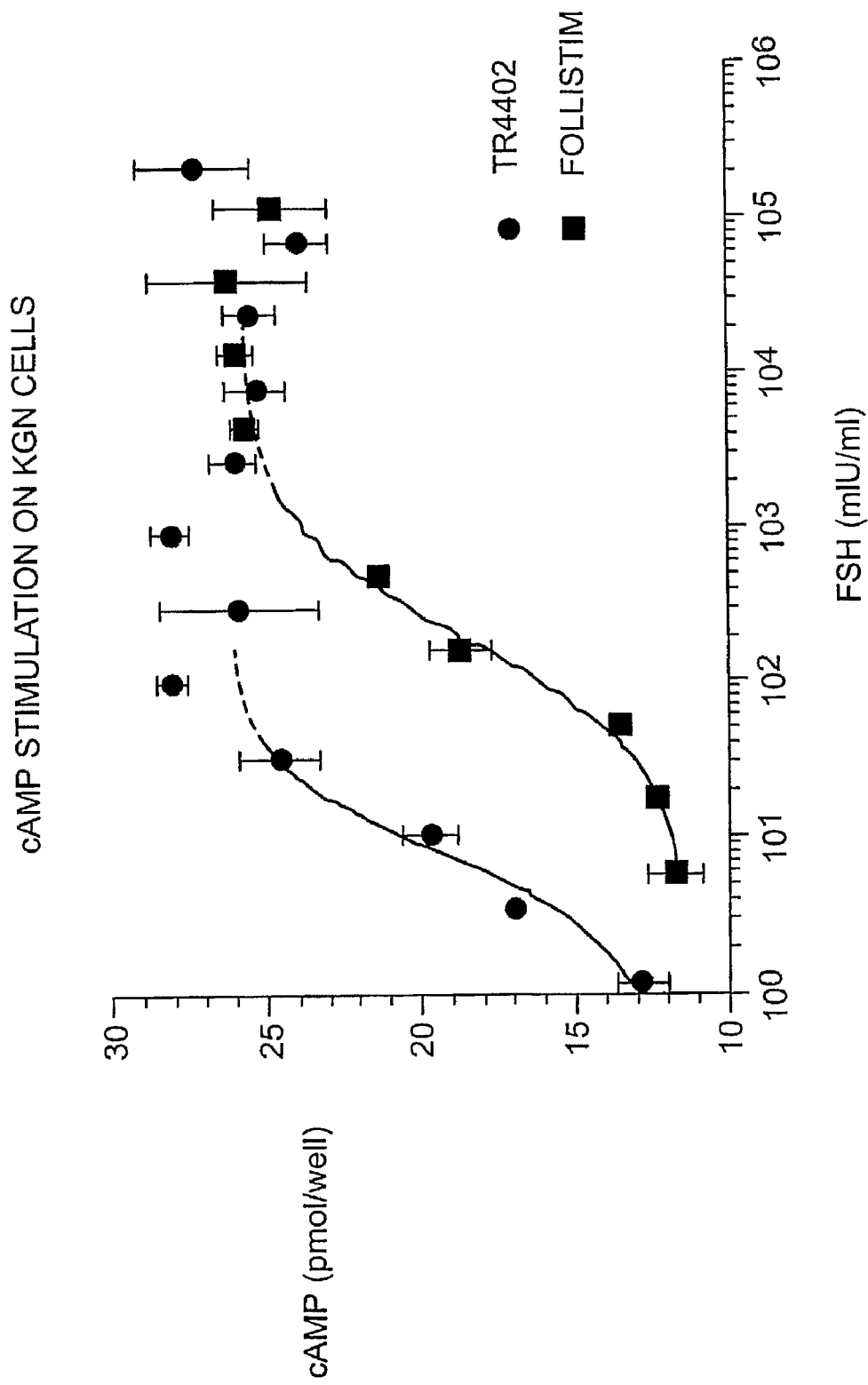
FIG. 7 is a graph showing cAMP production in KGN cells in response to purified analog TR-4402 versus wild type FSH.
Figure 8:
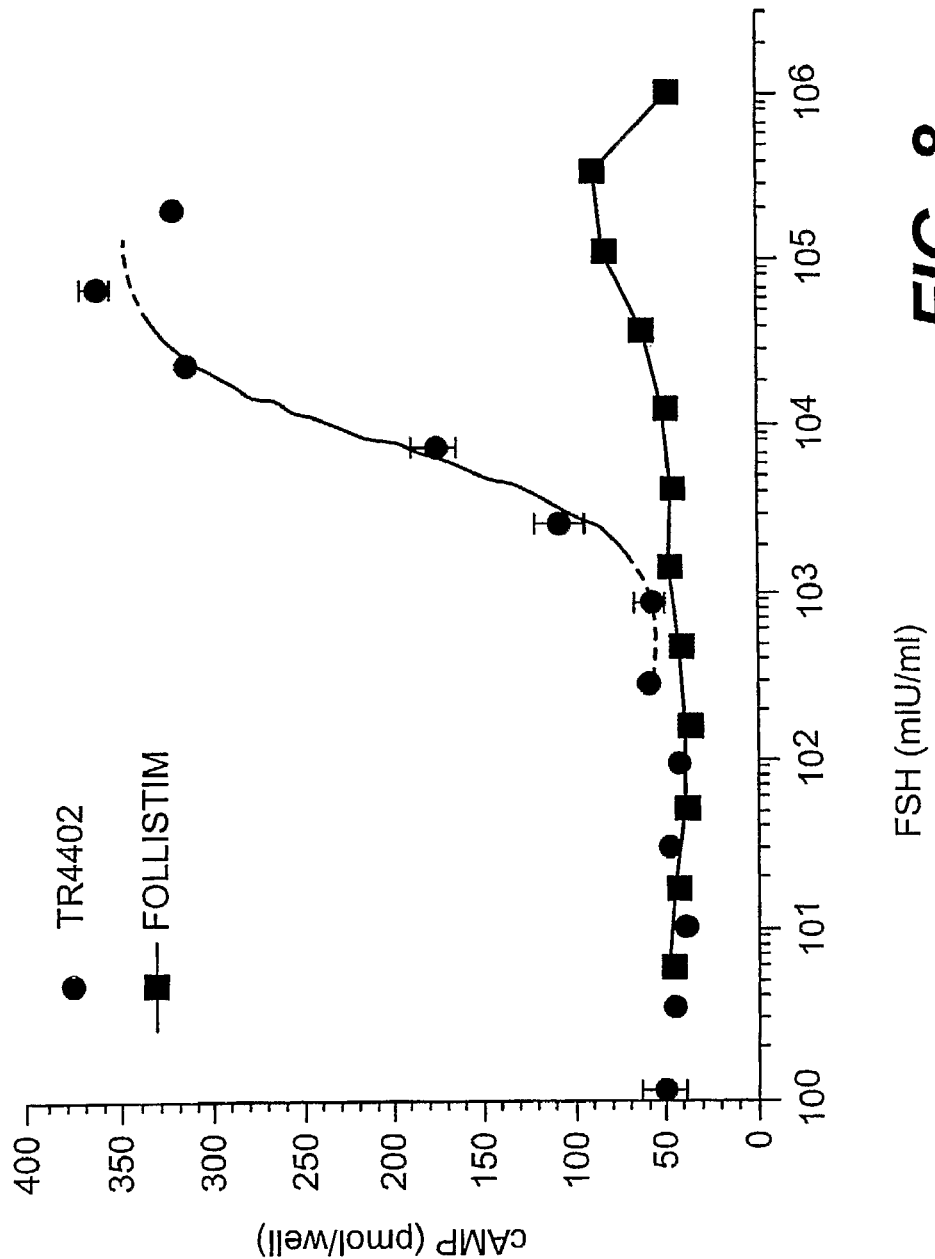
FIG. 8 is a graph showing cAMP production in GLHR-15 cells in response to purified analog TR-4402 versus wild type FSH.

FSH mutations showing the highest bioactivity in vitro and no adverse effects on FSH production were chosen for combination strains. FIG. 1 includes graphs showing a comparison of the effect of various single mutations on FSH bioactivity in vitro, as measured using transient transfection of CHO-FSHR cells. Single mutations showing the highest potency included basic substitutions at alpha positions Q13, E14, V68, P21 and G73, and at beta position E4. An arginine substitution at F18 resulted in a loss of bioactivity. Beta E4R in particular resulted in enhanced FSH production (see FIG. 2). The synergistic effect on bioactivity of several combined substitutions is shown in FIG. 3.

In total, 26 single mutations in the alpha subunit and 23 single mutations in the beta subunit were tested, and the top mutations in each subunit were selected to construct lead analogs with combined substitutions. Table 1 below shows combined mutations with a proven increase in bioactivity in vitro.

TABLE 1

Combined Substitutions Resulting in Enhanced Potency

| Analog | Substitutions |
|---|---|
| 4201 | alphaE14R + betaE4R |
| 4202 | alpha(E14R + N66R) + WT beta |
| 4203 | alpha(E14R + G73R) + WT beta |
| 4204 | alpha(P16R + Q20R) + WT beta |
| 4205 | alpha(Q20R + P21R) + WT beta |
| 4301 | alpha(E14R + Q20R + G73R) + WT beta |
| 4302 | alpha(E14R + P21R + G73R) + WT beta |
| 4303 | alpha(E14R + N66R + G73R) + WT beta |
| 4304 | alpha(E14R + N66R) + betaE4R |
| 4305 | alpha(E14R + G73R) + betaE4R |
| 4306 | alpha(P16R + Q20D + P21R) + WT beta |
| 4307 | alpha(P16R + Q20R + P21R) + WT beta |
| 4308 | alpha(N66K + G73K + A81K) + WT beta |
| 4401 | alpha(Q13R + E14R + P16R + Q20R) + WT beta |
| 4402 | alpha(E14R + Q20R + G73R) + betaE4R |
| 4403 | alpha(E14R + P21R + G73R) + betaE4R |
| 4404 | alpha(E14R + N66R + G73R) + betaE4R |

TABLE 1-continued

| Combined Substitutions Resulting in Enhanced Potency | |
|---|---|
| Analog | Substitutions |
| 4405 | alpha(Q13K + E14K + P16K + Q20K) + WT beta |
| 4501 | alpha(E14R + Q20R + P21R + N66R + G73R) + WT beta |
| 4601 | alpha(Q13K + E14K + P16K + Q20K + N66K + G73K) + WT beta |
| 4602 | alpha(E14R + P16R + Q20R + P21R + N66R + G73R) + WT beta |
| 4603 | alpha(E14R + Q20R + P21R + N66R + G73R) + betaE4R |
| 4701 | alpha(E14R + P16R + Q20R + P21R + N66R + G73R) + betaE4R |
| 4901 | [alpha(E14R + Q20R + G73R) + betaE4R] with N-terminal ANITV (SEQ ID No. 3) extension in the alpha subunit |
| 4910 | [alpha(Q13R + E14R + P16R + Q20R) + WT beta] with N-terminal ANITV (SEQ ID No. 3) extension in the alpha subunit |

As known in the art, a particular drug may exhibit different efficiencies depending on the system used. See Kenakin, "Predicting Therapeutic Value in the Lead Optimization Phase of Drug Discovery," Nature Rev. 2: 429-38 (2003). Therefore, the bioactivity of the analogs of the invention was also tested using rat granulosa cells expressing low quantities of FSH receptor (GLHR-15 cells). As shown in the graphs in FIG. 4, the analogs of the invention still resulted in significant cAMP responses, as compared to wild type FSH and free alpha chain, which did not show a significant dose dependent response.

Example 2

Purification and Characterization of Analog TR-4402

Analog TR-4402 was chosen for purification and further characterization. TR-4402 is a FSH analog containing two mutations in the alpha L1 loop (αE14R and αQ20R), one mutation in the alpha L3 loop (αG73R), and one mutation in the beta L1 loop (βE4R). See FIG. 5. The cell line producing TR-4402 was established by co-transfection of a modified pED vector containing the cDNA of the human alpha subunit and dihydrofolate reductase (DHFR) gene, and a modified pIRES vector containing the cDNA of FSH beta subunit, separated by an IRES sequence and the amplifiable gene marker, adenosine deaminase (ADA), into CHO-DHFR(−) by lipofectamine method. Transfected cells were cultured in selection medium (ribonucleosides and deoxyribonucleosides deficient aMEM with 10% dialyzed FBS). For stable production of hFSH analogs in a CHO double deletion mutant (dhfr-/dhfr-), the CHO-DG44 cell line was kindly provided by Dr. L. Chasin (Columbia University, New York, N.Y.).

Clonal cell lines secreting FSH#4402 were cultured in increasing concentrations of methotrexate (MTX) up to 2 μM. DHFR amplification is based on systematic increases of MTX in medium without added nucleosides. Cells were qualified for next amplification step after regaining their polygonal morphology (2-3 weeks). Since the concentration of MTX increased about 800× (from 0.005 uM to about 4 μM) the amplification process took about 4 months. Clones with highest secretion level were also subjected to a second treatment, involving the utilization of deoxycoformycin, directed to amplify the ADA marker gene.

Single clones were tested for expression using FSH immunoassay established for detection of FSH#4402. A stable cell line (clone ID: H-2-3), transfected with pED-analog a +pIRES-ADA-analog b (molar ratio of a:b=1:5, 5 mg total DNA), was selected and propagated in alpha-minimum essential medium (a-MEM: Cat #: 12561-056, Lot #1141509, with L-glutamine, without ribonucleosides and deoxyribonucleosides); GIBCO, Grand Island, N.Y.), supplemented with 10% dialyzed fetal bovine serum (Gibco, Cat No: 26400-044) and 2 mM methotrexate (MTX; ICN, Cat. No: 102299, Aurora, Ohio).

Preparation of bioreactor inoculums. When >90% CHO-DG44 cells were confluent in the 500-cm2 T-flasks, the cells were trypsinized, centrifuged at 400 g for 5 min at 4° C. Total cells (1.6'109/500 ml of a-MEM culture medium) were inoculated into the Celligen plus Bioreactor by feeding cell suspension in a 2 L-plastic bottle.

After amplification, the cell line producing the highest amount of FSH#4402 was grown in multiple flasks. Cells were further propagated using perfusion mode in Packed-Bed Bioreactor 3.5 L Bioreactor with internal retention device (basket) and vertical mixing system (Celligen Plus, New Brunswick Scientific, Edison, N.J.). Cells were trapped onto Fibracel disks located inside the retention assembly. Dissolved oxygen was kept at 50% saturation. Temperature was 37 C. Agitation was 100 rpm. The pH 7.2 was maintained using a four-gas mixing system and automatic injection of sodium bicarbonate. Perfusion was adjusted to keep glucose level above 1.5 g/L and lactate below 1.5 g/L.

FBS weaning process and FSH-TR 4402 analog production in Celligen plus bioreactor. CHO III A (Gibco, Formula No.: 97-0147DK, Lot No.: 1147268) supplemented with hypoxanthine-thymidine supplement (Gibco, 100'), penicillin-streptomycin (Gibco, 100'; Cat #: 15140-122, Lot #: 1161387), glutamax-1 (Gibco, 100'; Cat #: 35050-061, Lot #: 1163550), 10% pluronic F-68 (Gibco, 100', Cat #: 24040-032, Lot #: 1153058), and 1% dialyzed fetal bovine serum (Gibco) was used for serum weaning in the bioreactor. At day 17 of the bioreactor operation, we changed CHO-III A culture medium to CHO protein free, animal component-free medium (Sigma, Cat #: C-8730 Lot No.: 122K8401) until day 23 (see SLIDE summarizing bioreactor run). Medium from bioreactor was harvested, centrifuged, filtered (0.45 μm membrane) and concentrated using Millipore concentrators.

Purification. TR-4402 was purified using immunoaffinity (monoclonal Ab ME.112 from Maine Biotechnology Services, Inc.) and hydrophobic interaction chromatography. Purity was assessed based on SDS-PAGE (~85%).

Modified analog TR-4402 was characterized using in vitro bioassays employing CHO, human granulosa-like tumor (KGN) and rat granulosa (GLHR-15) cell lines expressing human FSH receptor and total cAMP production as an end point (see FIGS. 6-8). Using CHO-FSHR cells, TR-4402 showed a 30 fold increase in potency and 17% increase in Vmax as compared to Follistim (wild type FSH). Using KGN-FSHR, TR-4402 also showed a 30 fold increase in potency as compared to wild type FSH.

TR-4402 was also tested for binding to LH and TSH receptors to confirm FSH analog specificity, and isoelectric focusing was employed to confirm carbohydrate chain heterogeneity, i.e., the presence of alpha and beta subunits (data not shown).

The effect of TR-4402 as compared to wild type FSH was also tested on mouse follicles in vitro using EggCentris in vitro follicle bioassay. This assay studies the growth and development of early preantral follicles up to the ovulatory stage. The whole in vitro, process closely mimics the physiology of in vivo folliculogenesis. The culture system begins with isolation of a homogenous class of mouse preantral follicles between 100 and 130 μM in diameter. The follicules were individually plated and cultured for 12 days with 1, 3 and 9 mIU/mL of wild type ("compound 3") and TR-4402 ("compound 4").

Figure 9:
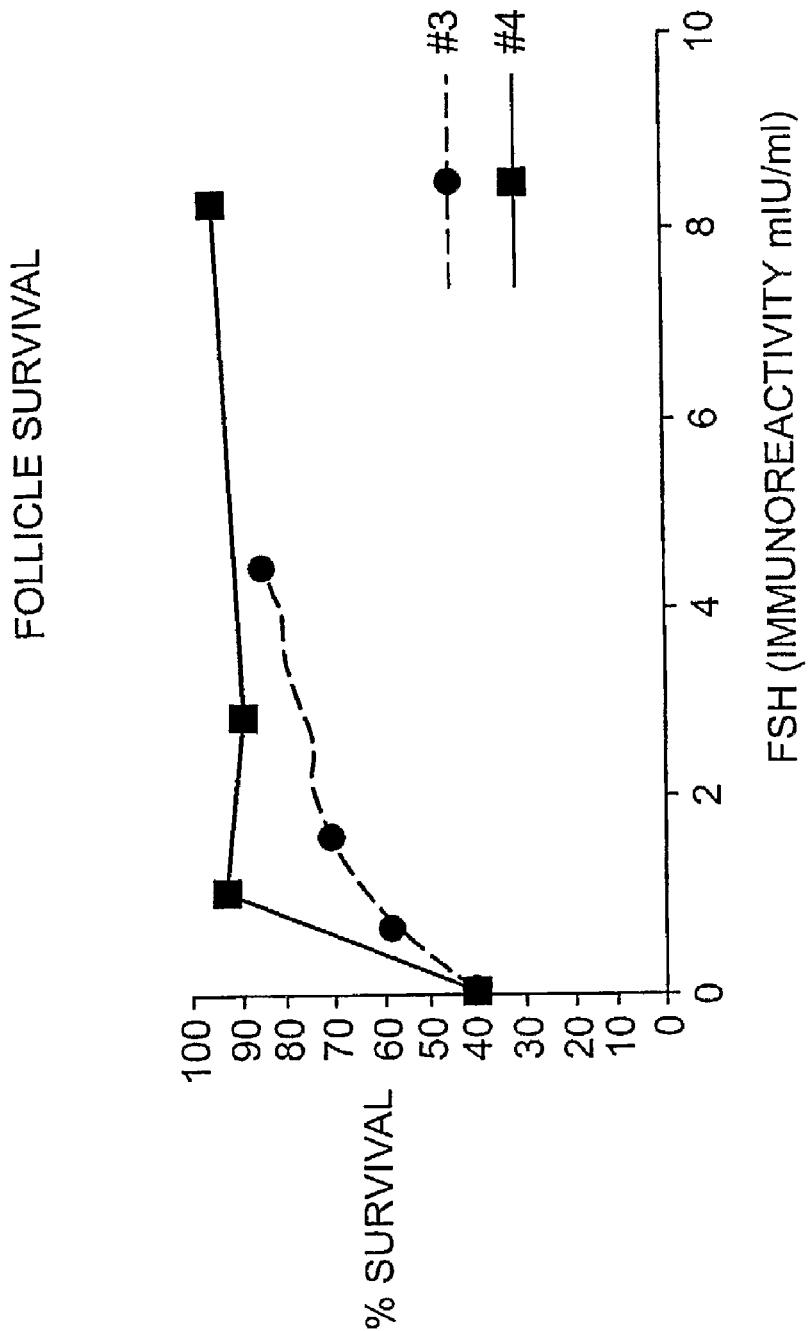
FIG. 9 is a graph showing follicle survival in the presence of wild type hFSH (compound #3) and analog TR-4402 (compound #4), observed during an in vitro follicle bioassay.
Figure 10:
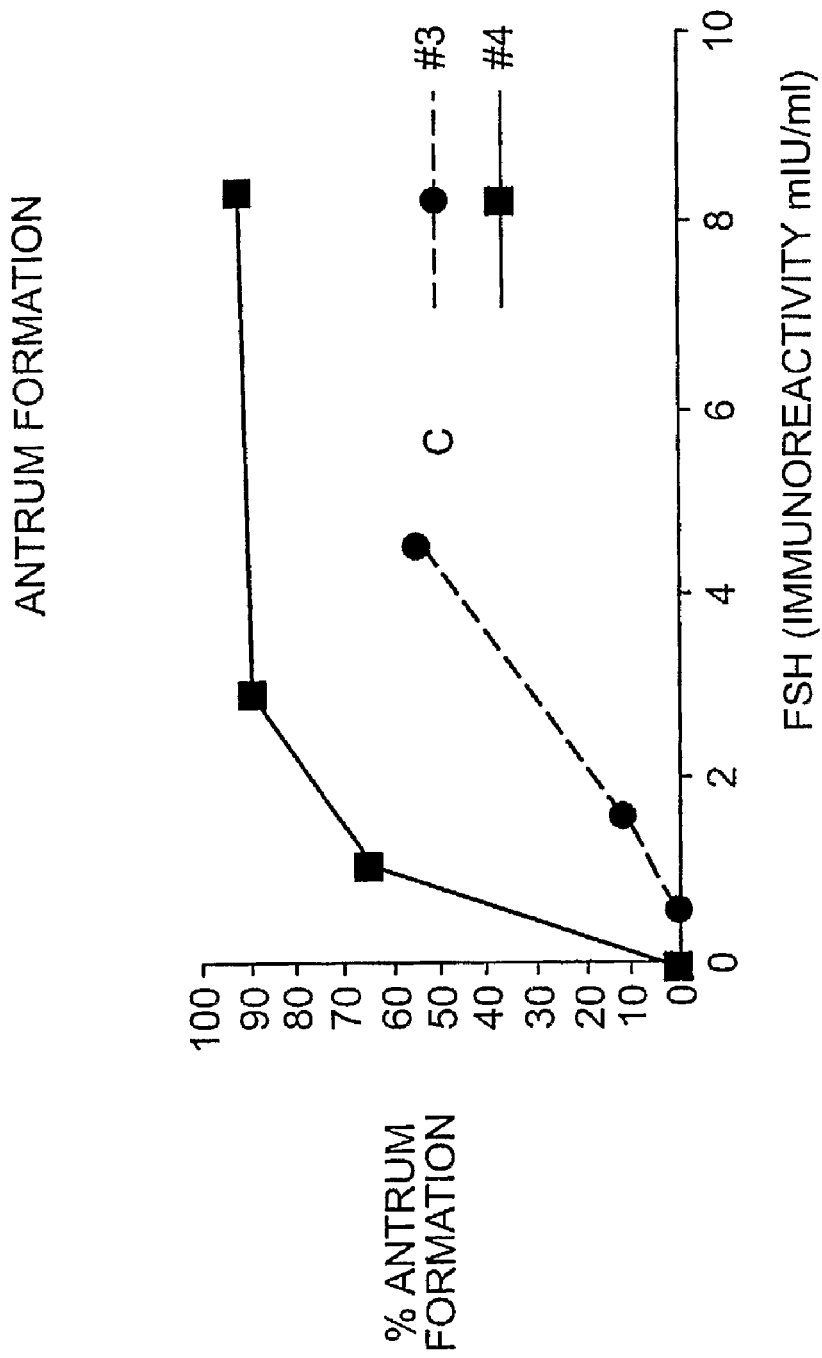
FIG. 10 is a graph showing antrum formation in the presence of wild type hFSH (compound #3) and analog TR-4402 (compound #4), observed during an in vitro follicle bioassay.
Figure 11A:
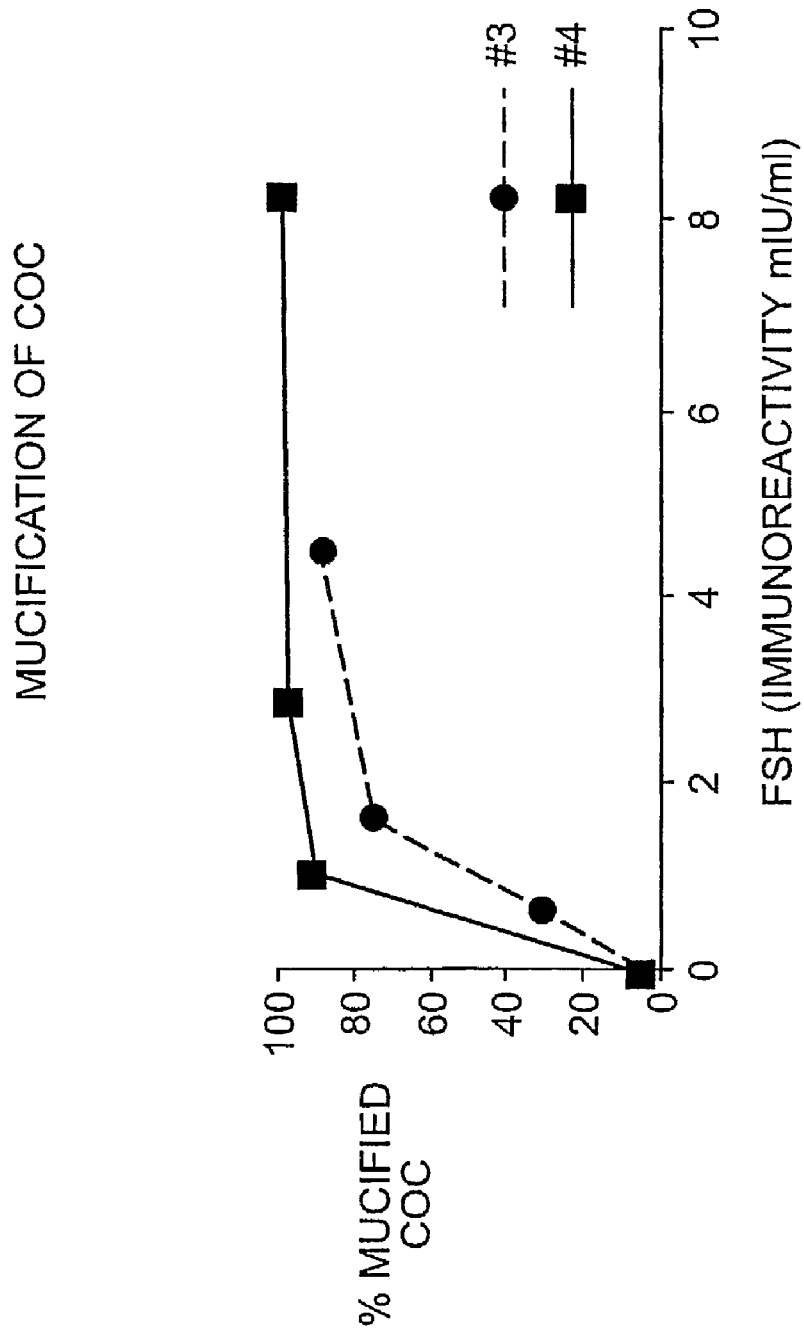
FIG. 11A is a graph showing mucification of COC in the presence of wild type hFSH (compound #3) and analog TR-4402 (compound #4), observed during an in vitro follicle bioassay.
Figure 11B:
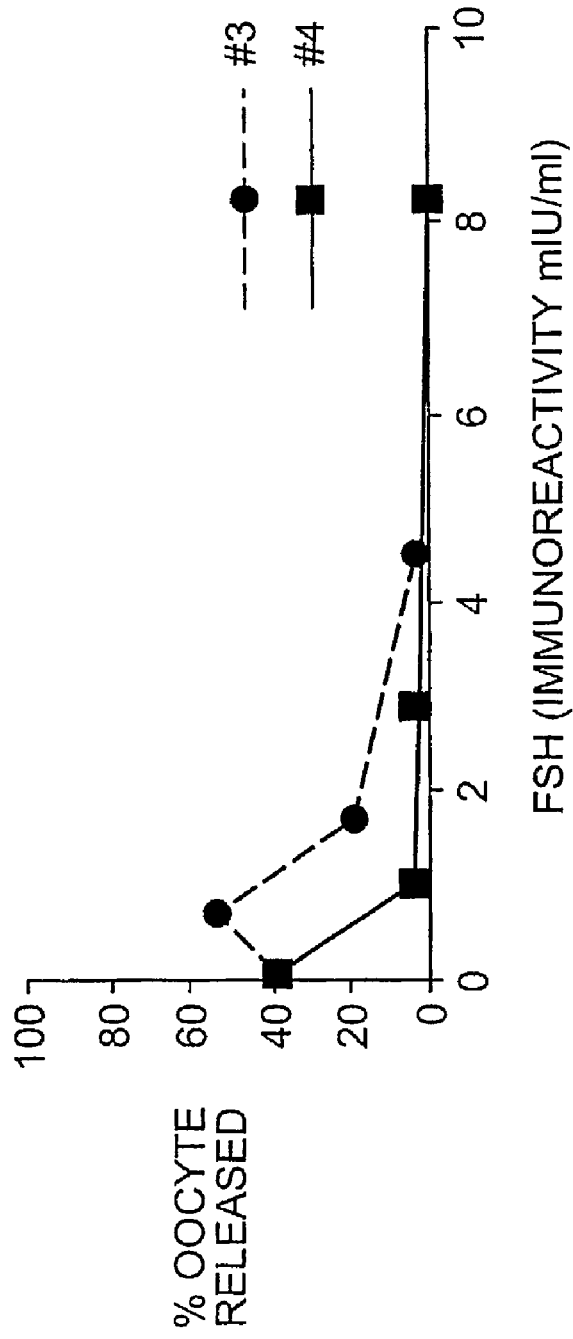
FIG. 11B is a graph showing % oocyte release upon hCG stimulation in the presence of wild type hFSH (compound #3) and analog TR-4402 (compound #4), observed during an in vitro follicle bioassay.
Figure 12:
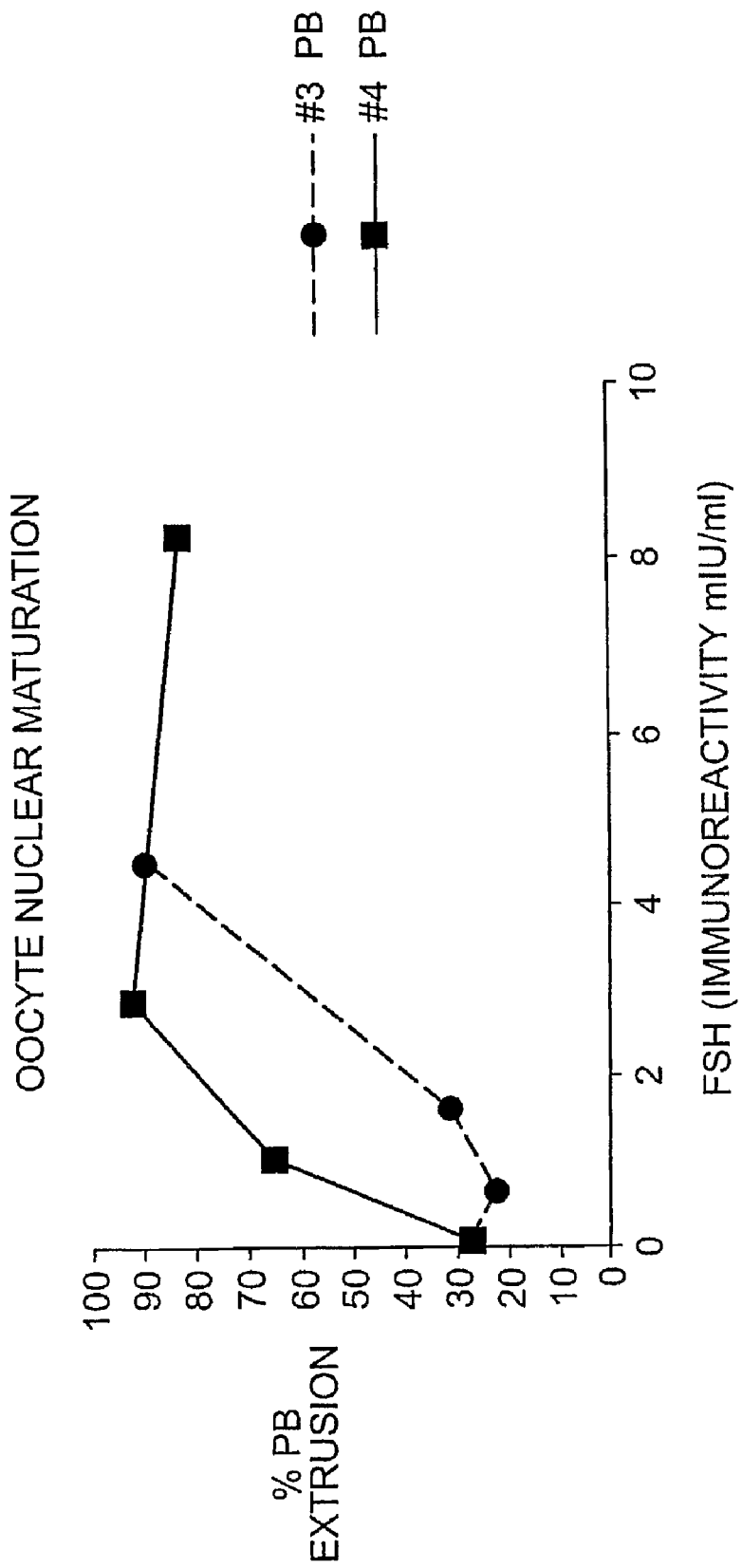
FIG. 12 is a graph showing oocyte nuclear maturation as measured by PB extrusion in the presence of wild type hFSH (compound #3) and analog TR-4402 (compound #4), observed during an in vitro follicle bioassay.
Figure 13A:
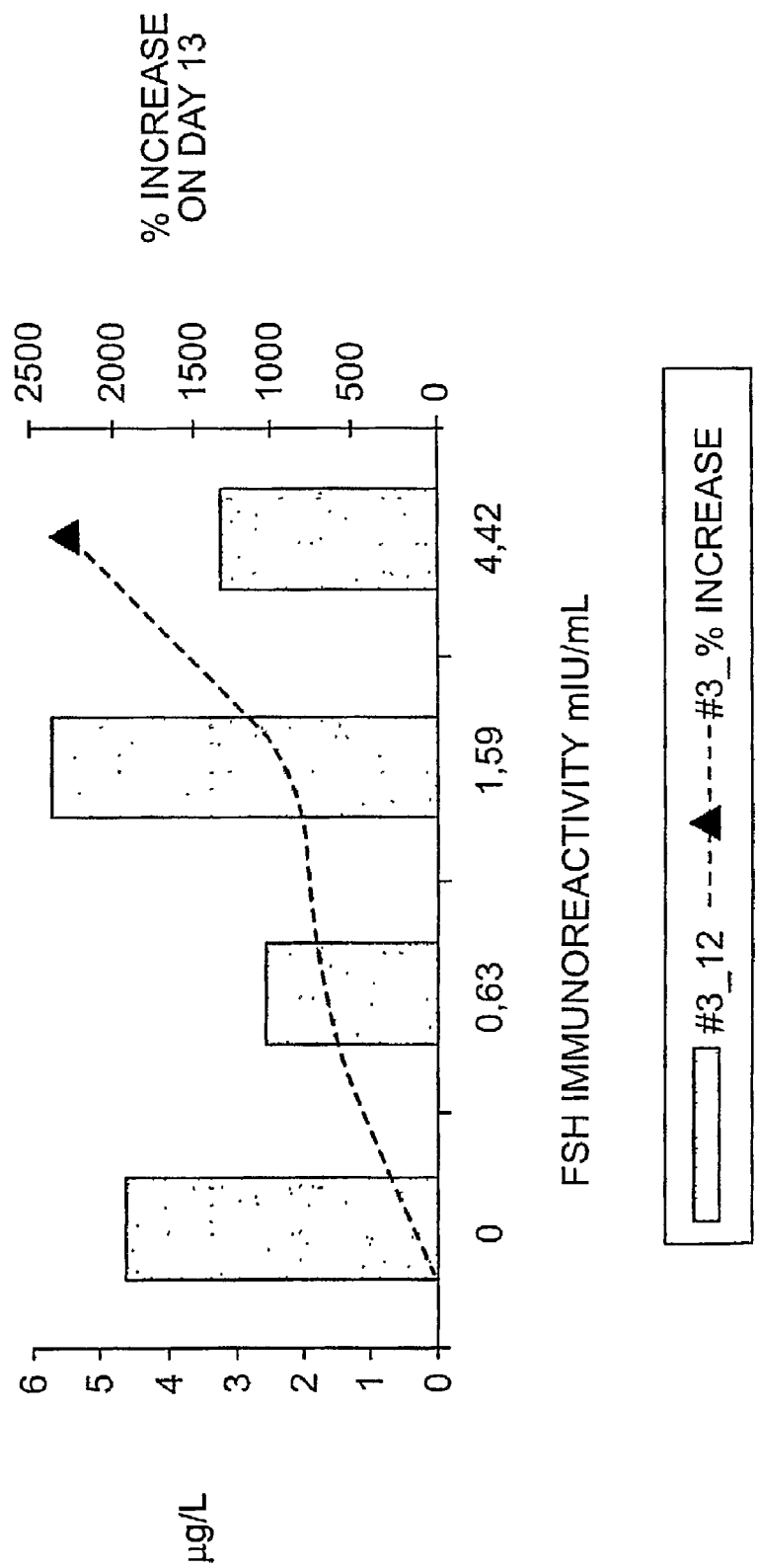
FIGS. 13A and B are graphs showing progesterone production in the presence of wild type hFSH (compound #3) (13A) and analog TR-4402 (compound #4) (13B), observed during an in vitro follicle bioassay.
Figure 13B:
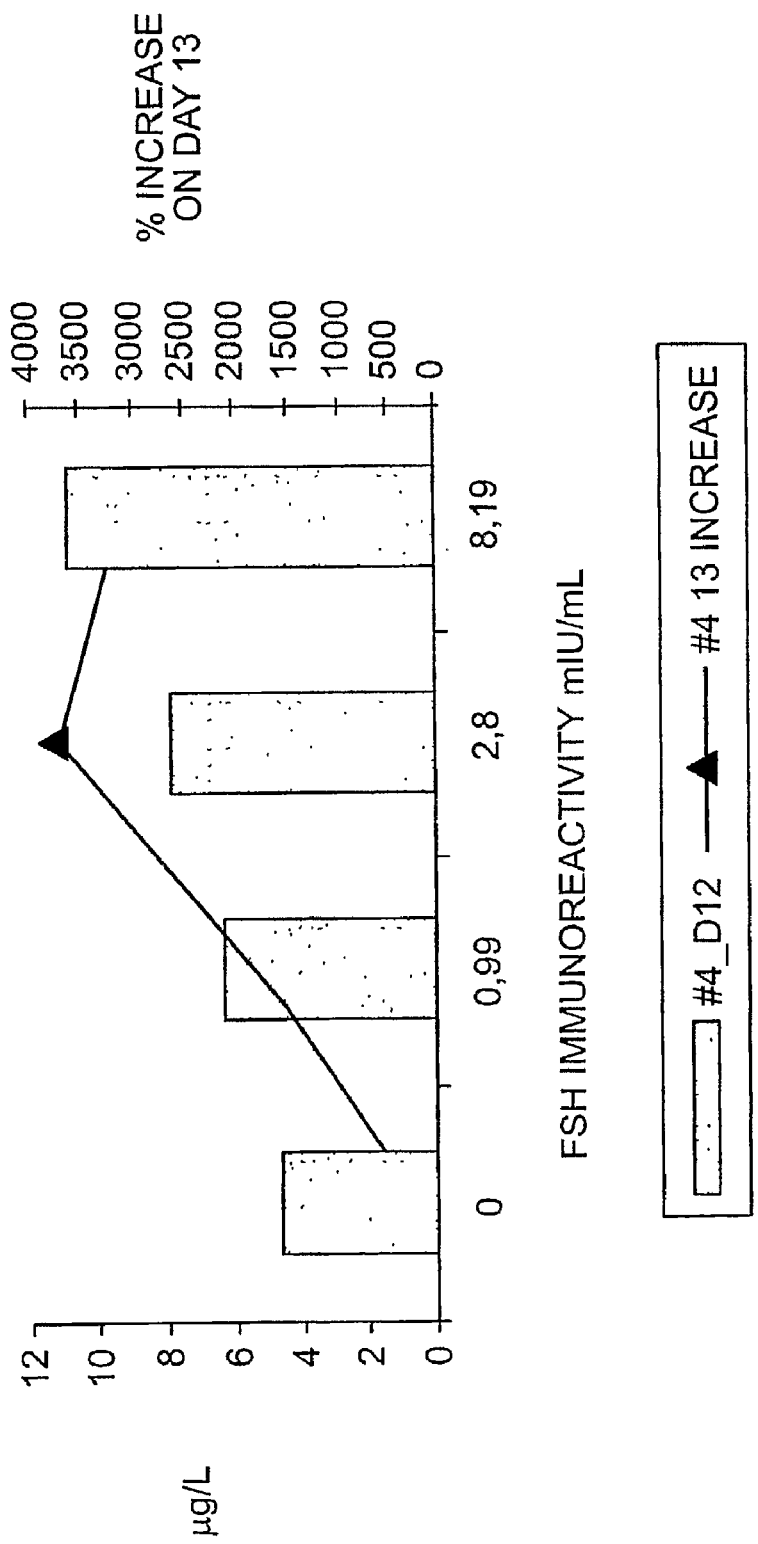

The follicle bioassay indicated that quality of the oocytes is improved after exposure to TR-4402 in comparison to Follistim (wild type) as shown by enhanced follicle survival (FIG. 9), enhanced antrum formation (FIG. 10), enhanced mucification of COC (FIG. 11), enhanced nuclear maturation (FIG. 12) and enhanced progesterone production (FIG. 13). Such differences could be related to the presence and anti-apoptotic action of FSH receptor in the oocyte cell membrane (see, e.g., Meduri et al., J. Clin. Endocrinol. Metab. 87(5): 2266-76), and indicate that the modified superagonists of the invention may be used to improve the performance of oocytes in patients seeking assisted reproduction therapy.

Example 3

In vivo Studies Using TR-4402

In vivo studies of TR4402 were performed using immature 21-day old Sprague-Dawley female rats. The FSH injection was performed subcutaneously once a day for 3 days (0, 24 and 48 h). At 72 h blood samples were collected and autopsy was performed. The weight of both ovaries was measured. FSH and inhibin B levels in sera were determined using ICN-IRMA FSH immunoassay. Intra-ovarian estradiol content was determined after homogenization of ovaries—using CT 17beta-estradiol kit (ICN Pharmaceuticals, Inc.).

Figure 14A:
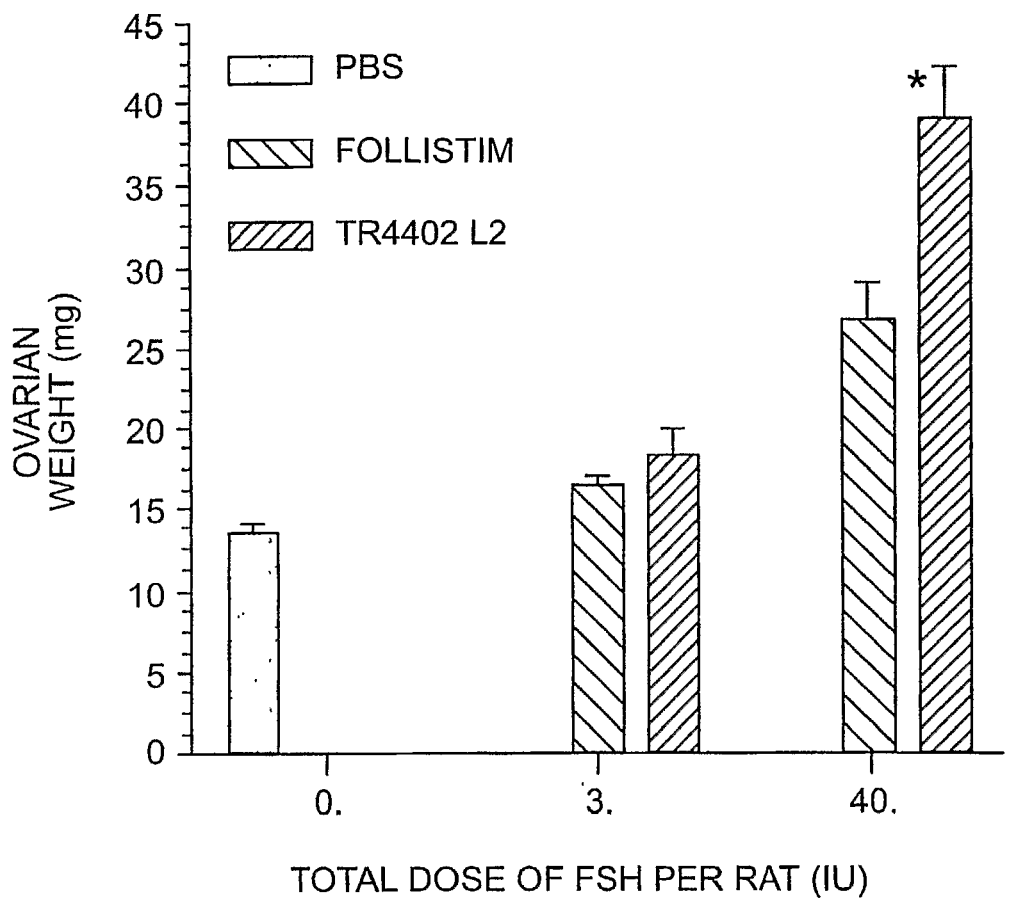
FIGS. 14A-D show the results of a Steelman-Pohley Bioassay performed using immature Sprague-Dawley Female Rats (Steelman and Pohley, 1953). The graphs in FIG. 14A, C and D show differences in ovarian weight measured in response to TR-4402 as compared to wild type (Follistim). The graph in FIG. 14B compares the serum levels of TR-4402 and wild type FSH during the bioassay.
Figure 14B:
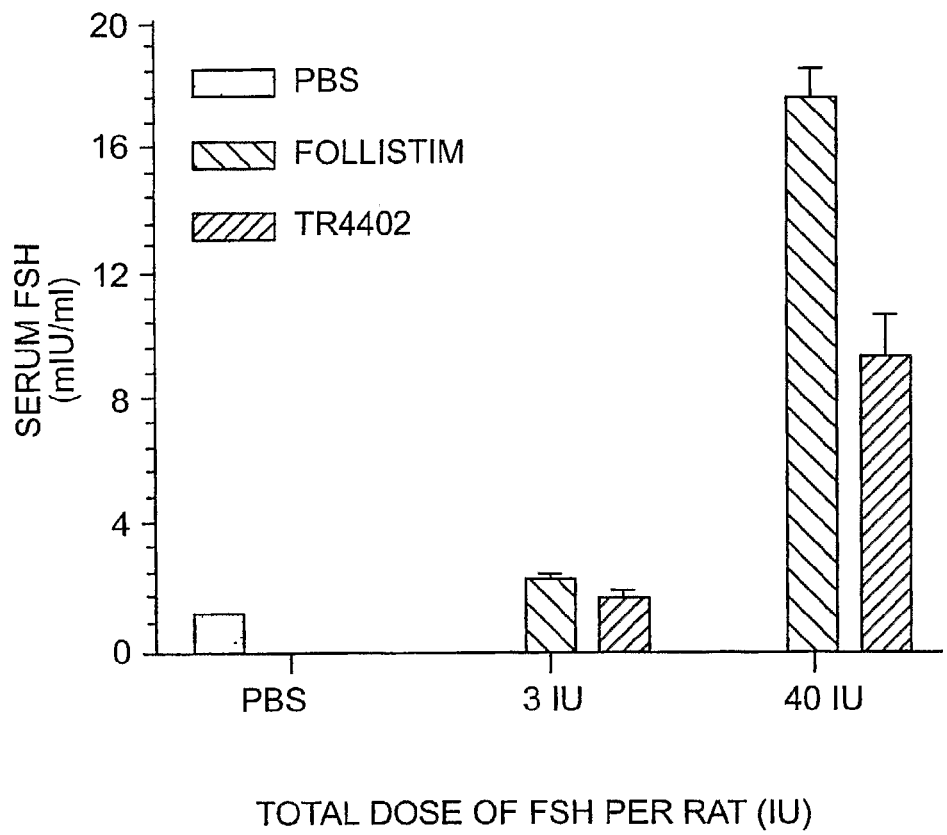
Figure 14C:
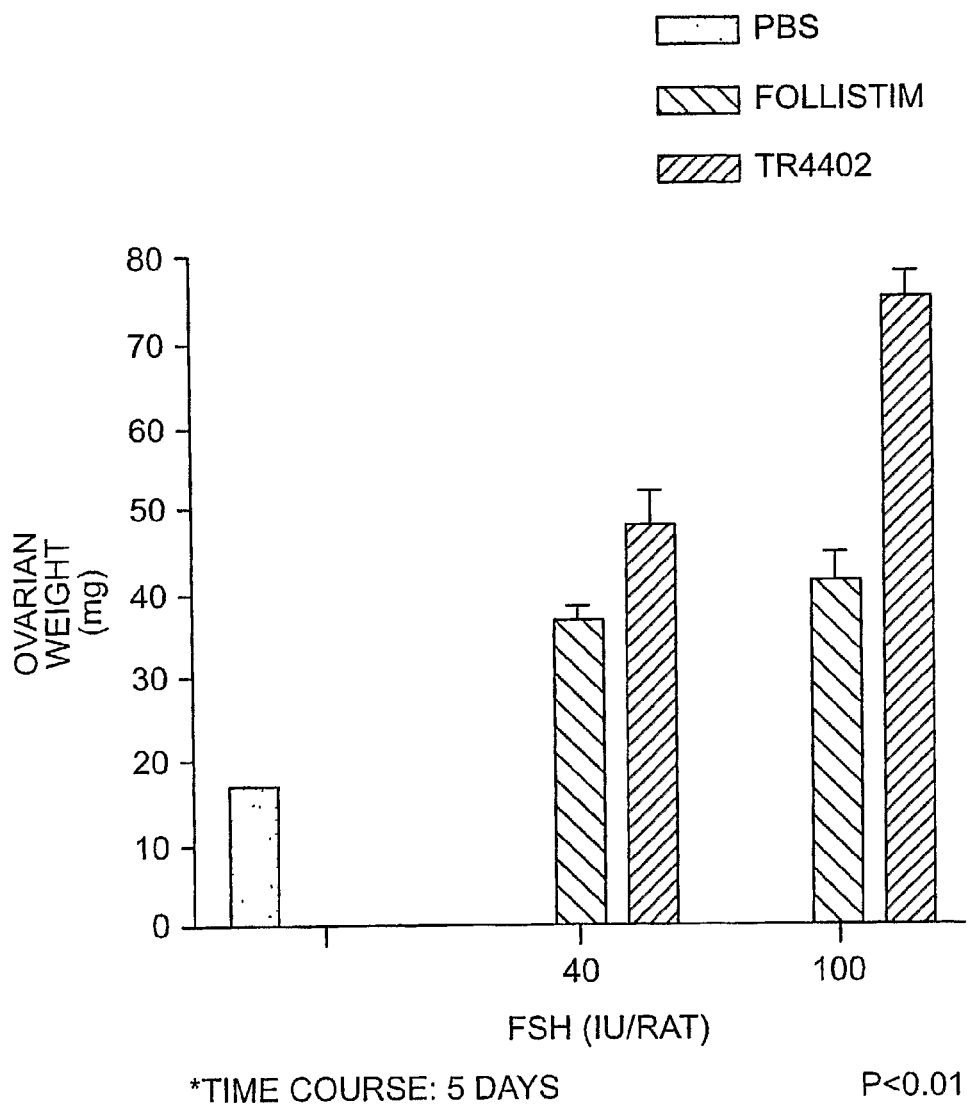
Figure 14D:
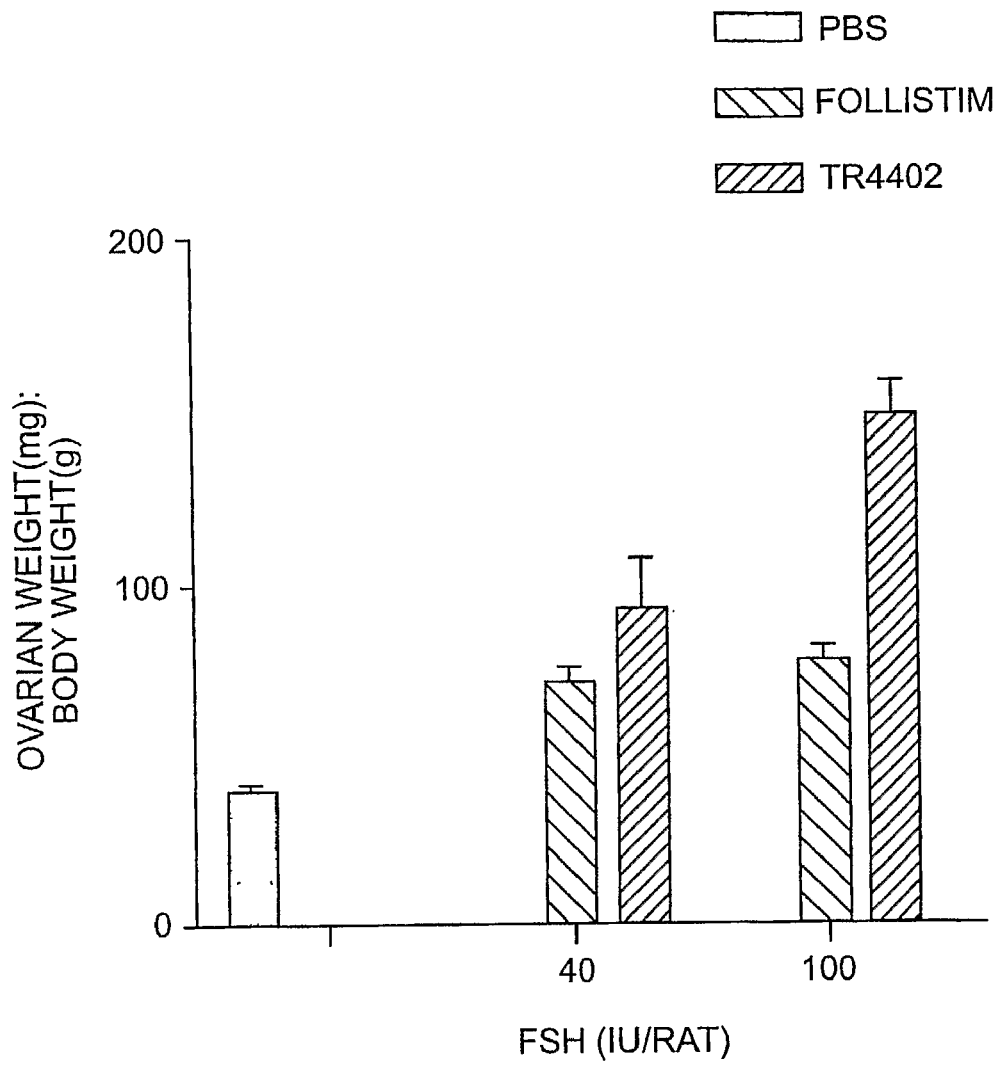

An increase of ovarian weight has been previously correlated with injected dose of FSH (Steelman and Pohley, 1953). FSH stimulates follicle growth (granulosa cells proliferation, hyperaemia, estradiol and inhibin B production). Statistically significant differences in ovarian weight (FIG. 14A, C and D), intra-ovarian estradiol content (FIG. 15) and serum inhibin B levels (FIG. 16) after stimulation with corresponding doses of TR-4402 and Follistim were observed. Such advantage of TR-4402 over wild type FSH in terms of ovarian weight, inhibin and estradiol production was observed despite a 40-50% lower level of TR-4402 than Follistim remaining in sera at the end of each experiment (see FIG. 14B).

Since studies in rodents are generally considered as good indicators of clinical efficacy of FSH preparations in humans, it is expected that TR-4402 should show considerable advantage over Follistim for the treatment of human patients. Moreover, a superactive FSH with faster clearance rate (such as TR-4402) should have immediate applications at the second phase of IVF protocol and result in decreased occurrence of ovarian hyperstimulation syndrome (OHSS).

Example 4

In vitro Fertilization, Embryo Development, and Live Births Studies Comparing FSH Analogs to Wild Type FSH Twenty-three day old B6D2F1 female mice (groups of 5) received one subcutaneous injection of 10 IU of TR-4401, 10 IU TR-4901, 10 IU wild type FSH (Follistim), or 20 IU wild type FSH (Follistim) on day one of the experiment. An ovulatory dose of hCG was administered by an intraperitoneal injection in at least one animal as a control.

After seventy-two hours from the FSH injection, sperm and oocytes were collected and fertilization occurred. Sperm was collected from male B6D2 and CB6F1 mice greater than 2 months of age. The male mice were sacrificed by cervical dislocation. An incision was made in the lower area of the abdomen, and the epididymis and vas deferens were dissected out and placed in a sperm dish. The epididymis and vas deferens were cut 3 to 5 times, and the sperm was gently squeezed out of the organs on to the sperm dish. The sperm dish with sperm was placed in an incubator at 37° C. and 5% $CO_2$ and allowed to capacitate 30 to 90 minutes.

Oocytes were collected from the superovulated female mice which had received TR-4401, TR-4901, or wild-type FSH (Follistim) by sacrificing the female mice and dissecting out the oviducts. The oviducts were placed in a drops of HTF medium and the ampulae were torn to release egg clutches. The intact egg clutches were transferred to fertilization dishes and counted. Table 2 provides the count of oocytes per group of five mice. FSH analogs TR-4401 and TR-4901 produced more oocytes at the 10 IU dosage than recombinant wild type FSH (Follistem) at the 10 IU and 20 IU dosages.

After the oocytes were placed in the fertilization dishes, aliquots of sperm ($1 \times 10^6$ to $2 \times 10^6$ sperm/ml) were added to each fertilization dish. The fertilization dishes were placed in the incubator at 37° C. and 5% $CO_2$ for a minimum of four hours to allow fertilization to occur. After the four hours of incubation, the fertilized eggs were transferred from the fertilization dishes to wash dishes where they were washed at least two times in drops of 250 µl of HTF medium to remove debris. The oocytes were stored in HTF drops in the dishes in the 37° C. and 5% $CO_2$ incubator overnight.

Twenty-four hours after fertilization, the cells were removed from the incubator. Two cell embryos were counted (Table 2, column titled "number of 2 cell embryos"), and the fertilization rate was determined by the percentage of oocytes which developed into two cell embryos (Table 2, column "% of 2-cell embryos"). The number of resulting two cell embryos was greater for the groups of mice treated with FSH analogs TR-4401 and TR-4901. The fertilization rate for all groups (FSH analogs and recombinant wild type FSH) was high.

The two-cell embryos were subsequently transferred to cultured dishes for further development (Table 2, column titled "number of 2-cell embryos remaining in culture") or implanted in pseudopregnant females (Table 2, column titled "number of 2-cell embryos transferred").

The embryos which remained in the culture dishes were observed for blastocyst formation on the fourth day after fertilization. The number of developing blastocysts is provided in Table 2 in the column titled "number of developing blastocysts". Table 2 provides both the total number of blastocysts and the number of blastocysts which hatched.

The two cell embryos which were implanted for fertilization were implanted in CD1 females between six and eight weeks old. Sixty 2-cell embryos were implanted in each test group of three mice with the exception of the TR-4401 group which had forty 2-cell embryos implanted. The mice were anesthetized with a solution of ketamine/zylazine by intraperitoneal injection. Once anesthetized, each mouse was shaved, and a small (0.5 cm) incision was made caudal of the rib cage and at the first one third of the flank of the dorsal to ventral. Another incision was made in the body wall to provide access to the abdominal cavity. Forceps were used to grasp the ovarian fat pad and gently withdraw the ovary, oviduct, and proximal end of the uterus through the body wall. The ovary and oviduct were positioned on a cotton swab to create an angle on the ovarian-oviductal junction. The infundibulum was identified under a stereomicroscope, and two pairs of superfine forceps were used to make a hole in the bursa. Embryos were transferred by pipetting a minimal volume of M2 medium with the embryos into the infundibulum. The organs were then relocated into the body wall and sutured with one or two stitches. The skin incision was closed with one or two wound clips. The mice were observed for daily. After ten days, the recipient mice were checked for pregnancy. Table 2, column "pregnancy from 2-cell embryo transfer" provides the number of resulting pregnancies per test group. FSH analog TR-4901 produced the most pregnancies.

A similar experiment comparing TR-4401 to recombinant wild type FSH was performed using birth as an end-point. Female mice (3 mice/group) were injected with 1 IU hCG and 3 IU of pregnant mare serum gonadotropin (PMSG) as a control, 1 IU wild type FSH (Gonal F), 3 IU wild type FSH (Gonal F), 1 IU TR-4401, or 3 IU TR-4401. The mice were injected 48 hours later with an ovulatory dose of 5 IU hCG. Twenty hours after the ovulatory dose, oocytes were counted and in vitro fertilization was allowed to take place as previously described. Subsequently, twenty 2-cell embryos were implanted in pseudo-pregnant mothers. Table 3 provides the results of this experiment. The test groups which received 1 IU or 3 IU of TR-4401 achieved greater oocyte counts, higher rates of blastocyst development, and higher birth rates compared to the control group and test groups treated with recombinant wild type FSH.

TABLE 4

| Treatment groups (3 mice/group) | |
|---|---|
| Treatment (Day-2) | hCG (Day 0) |
| Control: 2.5 IU PMSG (Folligon) | 5 IU hCG (Chorulon) |
| Control: hCG only | 5 IU hCG |
| 0.5 IU Recombinant FSH (Gonal F) + 1 IU hCG (Ovitrelle) | 5 IU hCG (Ovitrelle) |
| 0.5 IU TR-4401 + 1 IU hCG (Ovitrelle) | 5 IU hCG (Ovitrelle) |
| 1 IU Recombinant FSH (Gonal F) + 1 IU hCG (Ovitrelle) | 5 IU hCG (Ovitrelle) |
| 1 IU TR-4401 + 1 IU hCG (Ovitrelle) | 5 IU hCG (Ovitrelle) |
| 3 IU Recombinant FSH (Gonal F) + 1 IU hCG (Ovitrelle) | 5 IU hCG (Ovitrelle) |
| 3 IU TR-4401 + 1 IU hCG (Ovitrelle) | 5 IU hCG (Ovitrelle) |

Figure 21:
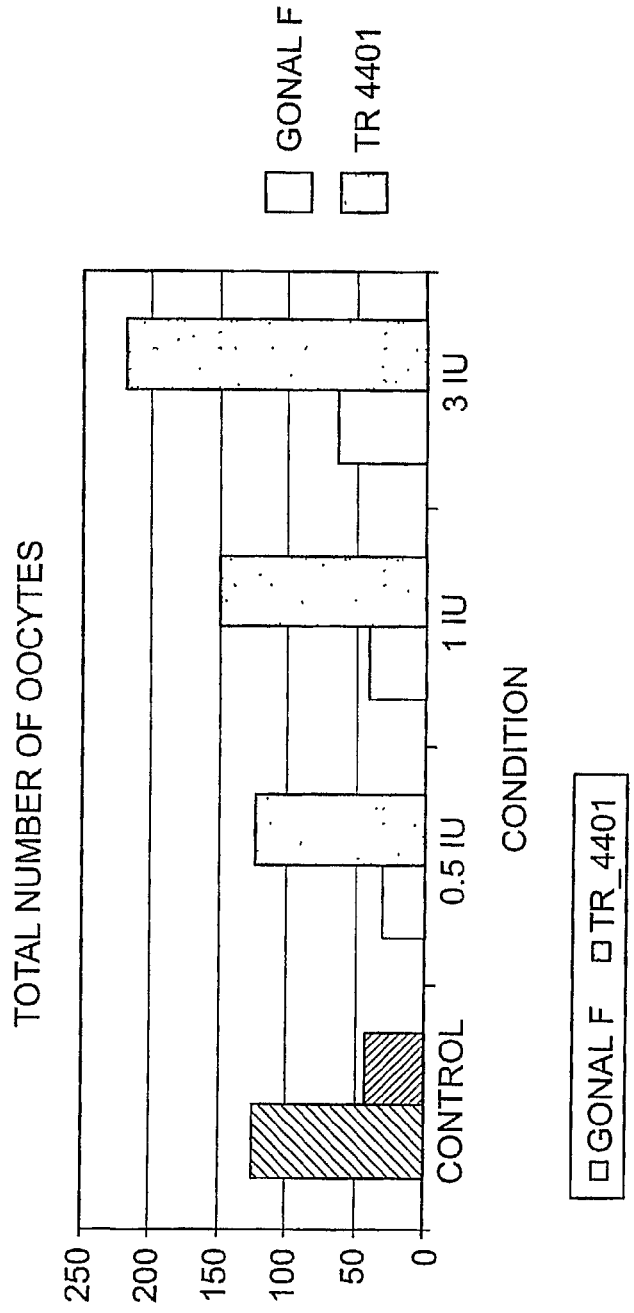
FIG. 21 is a graph showing the increase in total number of oocytes produced in vivo after administration of TR 4401 versus wild type FSH (Gonal F).

Treatment with TR-4401 was found to significantly increase the number of oocytes produced. FIG. 21 provides the total number of oocytes per group at the time of sperm washing (immediately prior to in vitro fertilization). The figure shows that TR-4401 produced more oocytes at all doses (0.5 IU, 1 IU, and 3 IU) than the test groups treated with recombinant wild type follicle stimulating hormone.

Figure 24:
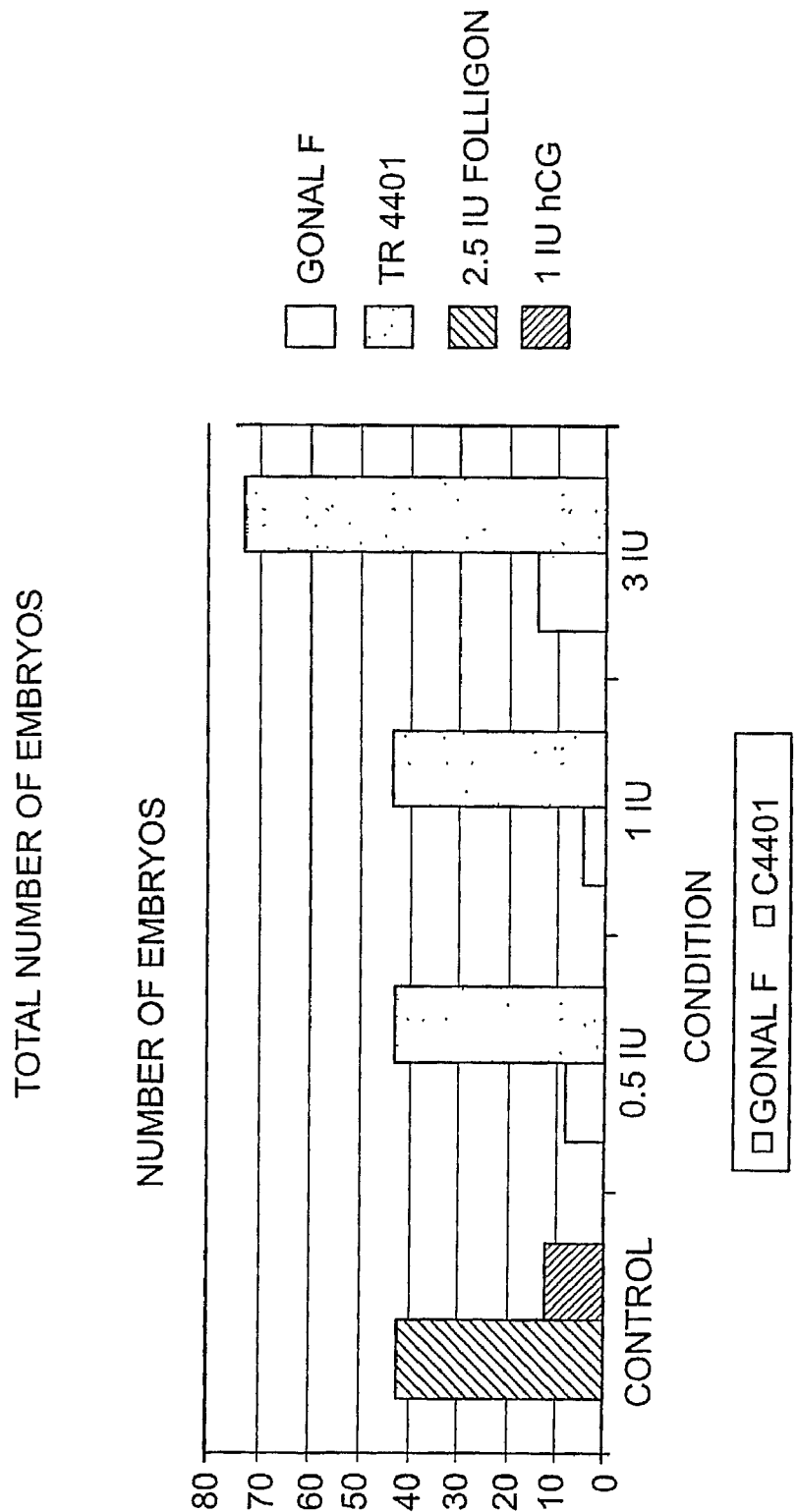
FIG. 24 is a graph showing the increase in total number of embryos after in vivo administration of TR 4401 versus wild type FSH (Gonal F).

Treatment with TR-4401 increased the total number of embryos resulting from in vitro fertilization. FIG. 24 provides the total number of 2-cell embryos per group. The figure

TABLE 2

In vitro Fertilization and Embryo Transfer Experiment Comparing TR-4401 and TR-4901 to Recombinant Wild-Type FSH (Follistim)

| Test Article Dose Level (IU/mouse) | Oocytes Count (per group) | Number of 2-cell embryos | % of 2-cell embryos | Number of 2-cell embryos transferred | Number of 2-cell embryos remaining in culture | Number of developing blastocysts | Pregnancy from 2-cell embryo transfer |
|---|---|---|---|---|---|---|---|
| 10 IU Follistim | 77 | 77 | 100% | 60 (3 females) | 12 | 6 total (3 hatched) | 0 |
| 20 IU Follistim | 165 | 161 | 98% | 60 (3 females) | 101 | 52 (37 hatched) | 2 |
| 10 IU TR-4401 | 207 | 204 | 99% | 40 (2 females) | 164 | 75 (38 hatched) | 1 |
| 10 IU TR-4901 | 376 | 369 | 98% | 60 (3 females) | 171 | 197 (126 hatched) | 3 |

TABLE 3

In Vitro Fertilization, Embryo Development, and Live Births Experiment Comparing TR-4401 to Recombinant Wild Type FSH (Gonal-F) and PMSG (control)

| Test Article Dose Level (IU/mouse) | Oocytes Count (per group) | Number of 2-cell embryos | % of 2-cell embryos | Number of 2-cell embryos remaining in culture | Number of developing blastocysts | % of developing blastocysts | Birth Rate |
|---|---|---|---|---|---|---|---|
| 3 IU PMSG | 58 | 51 | 88% | 31 | 18 | 58% | 0/20 |
| 1 IU Gonal F | 26 | 26 | 100% | 6 | 4 | 67% | 0/20 |
| 3 IU Gonal F | 21 | 21 | 100% | 1 | 0 | 0% | 0/20 |
| 1 IU TR-4401 | 78 | 59 | 76% | 19 | 12 | 63% | 5/40 |
| 3 IU TR4401 | 116 | 113 | 97% | 53 | 38 | 72% | 11/60 |

Example 5

Comparison of the Quantity and Quality of Oocytes from Mice Treated with TR-4401 FSH Analog and Recombinant Wild Type FSH (Gonal F)

Oocytes from B6CBAF1 mice were quantitatively and qualitatively assessed after in vivo treatment with a control or various doses of recombinant wild type FSH or FSH analog TR-4401 as described in Table 4. In vitro fertilization took place on day 1 (72 hours post treatment) according to the protocol previously described.

shows that TR-4401 produced more 2-cell embryos at all doses (0.5 IU, 1 IU, and 3 IU) than the test groups treated with recombinant wild type FSH.

Figure 22:
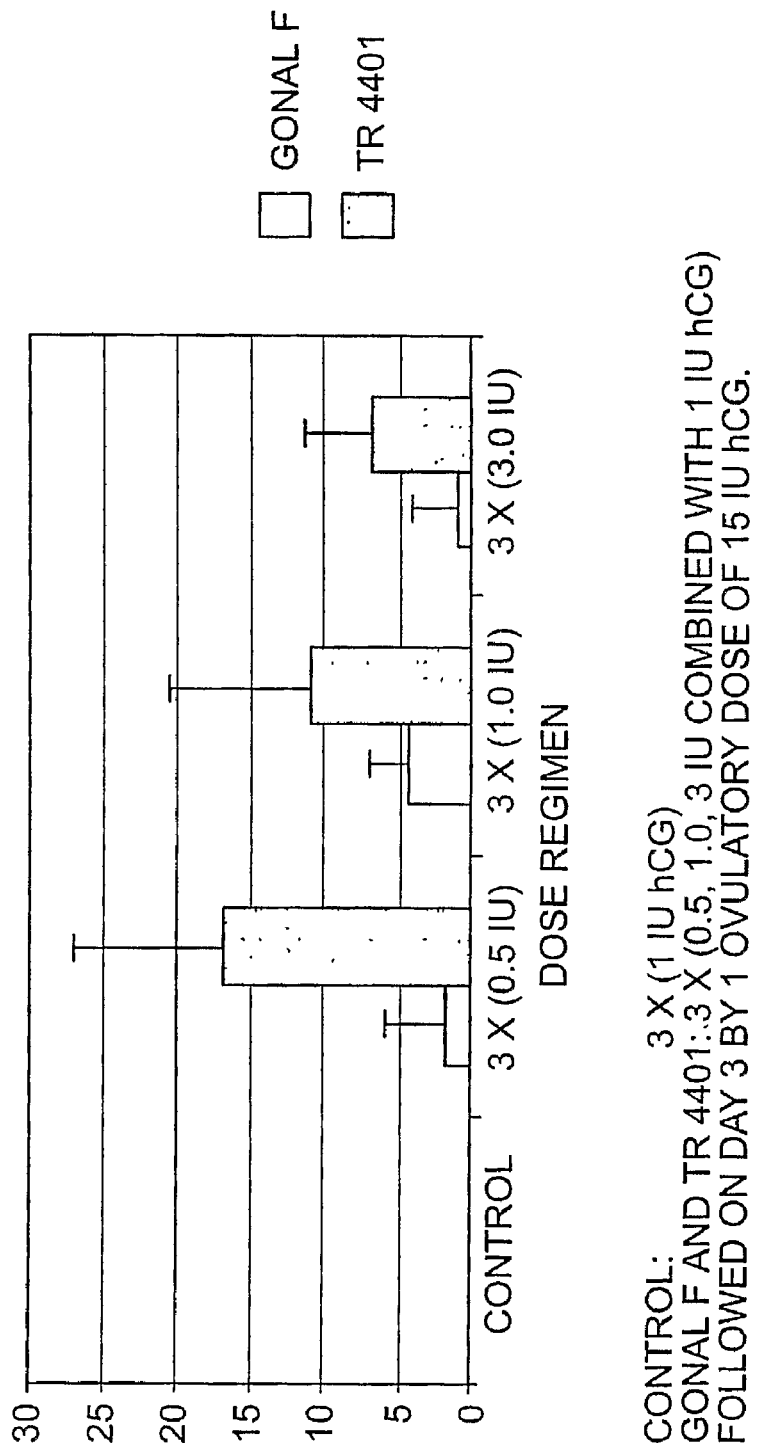
FIG. 22 is a graph showing the increase in fertilization rate of oocytes after in vivo administration of TR 4401 versus wild type FSH (Gonal F).
Figure 23:
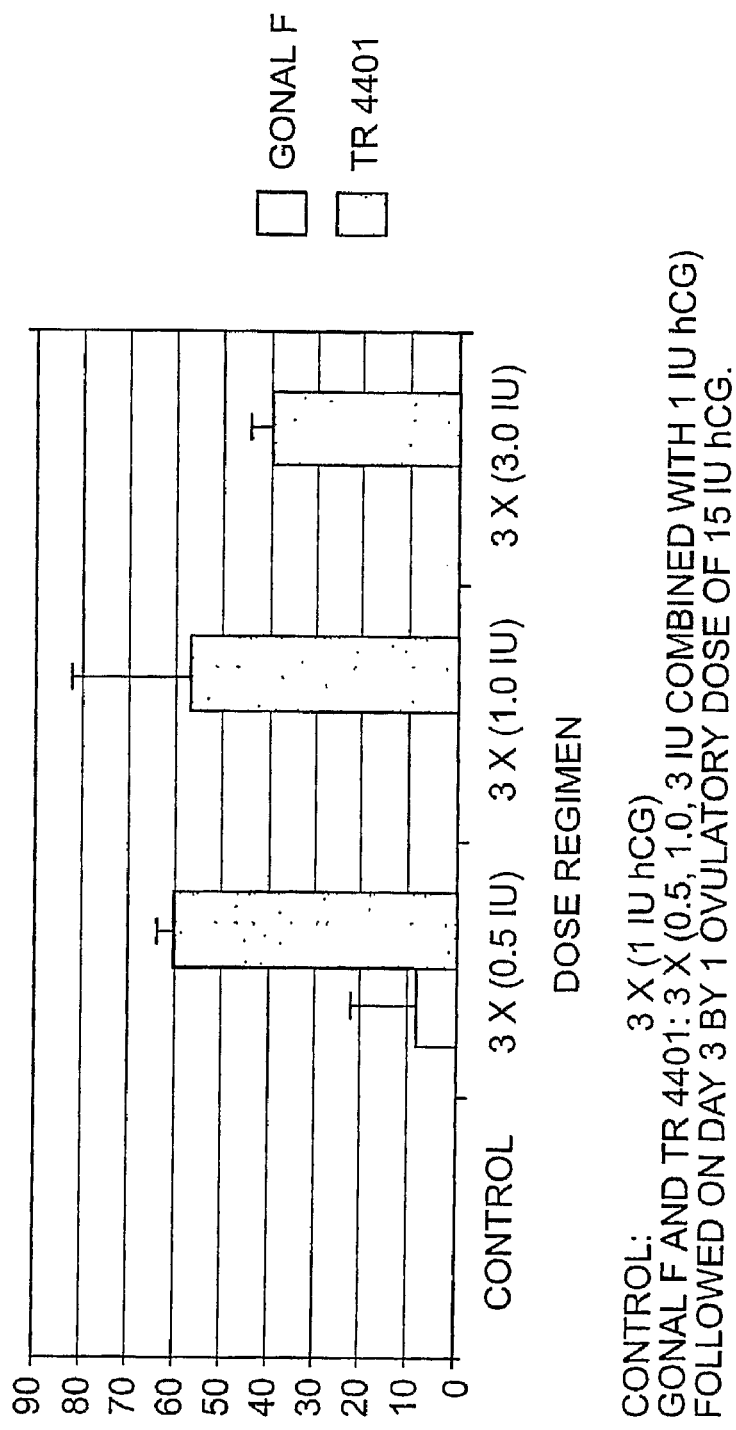
FIG. 23 is a graph showing the increase in blastocyst formation rate after in vivo administration of TR 4401 versus wild type FSH (Gonal F).

In a similar experiment, test groups received 3 doses of 0.5, 1, or 3 IU of TR-4401 or recombinant wild type FSH (Gonal F) combined with 1 IU of hCG. A control group received 3 doses of 1 IU hCG. On day 3, all groups were given one ovulatory dose of 15 IU hCG. In vitro fertilization was performed on mice as previously described. FIG. 22 shows that mice treated with the TR-4401 FSH analog displayed higher fertilization rates at all doses (3× (0.5, 1, 3 IU)+1 IU hCG) than mice treated with recombinant wild type FSH (Gonal F) or the control. Furthermore, oocytes from mice treated with the lowest dose of TR-4401 (3×0.5 TR-4401+1 IU hCG) displayed a higher fertilization rate than those from mice treated with higher doses of TR-4401. FIG. 23 shows that embryos from mice treated with the TR-4401 FSH analog (all dosages) displayed higher blastocyst formation rates than the embryos from the test group treated with recombinant wild type FSH. Embryos from mice treated with the lowest dose of TR-4401 (3×0.5 TR-4401+1 hCG) displayed a greater blastocyst formation rate than embryos from mice treated with higher doses of TR-4401.

Example 6

Pharmokinetics Comparison of FSH Analogs

Figure 17B:
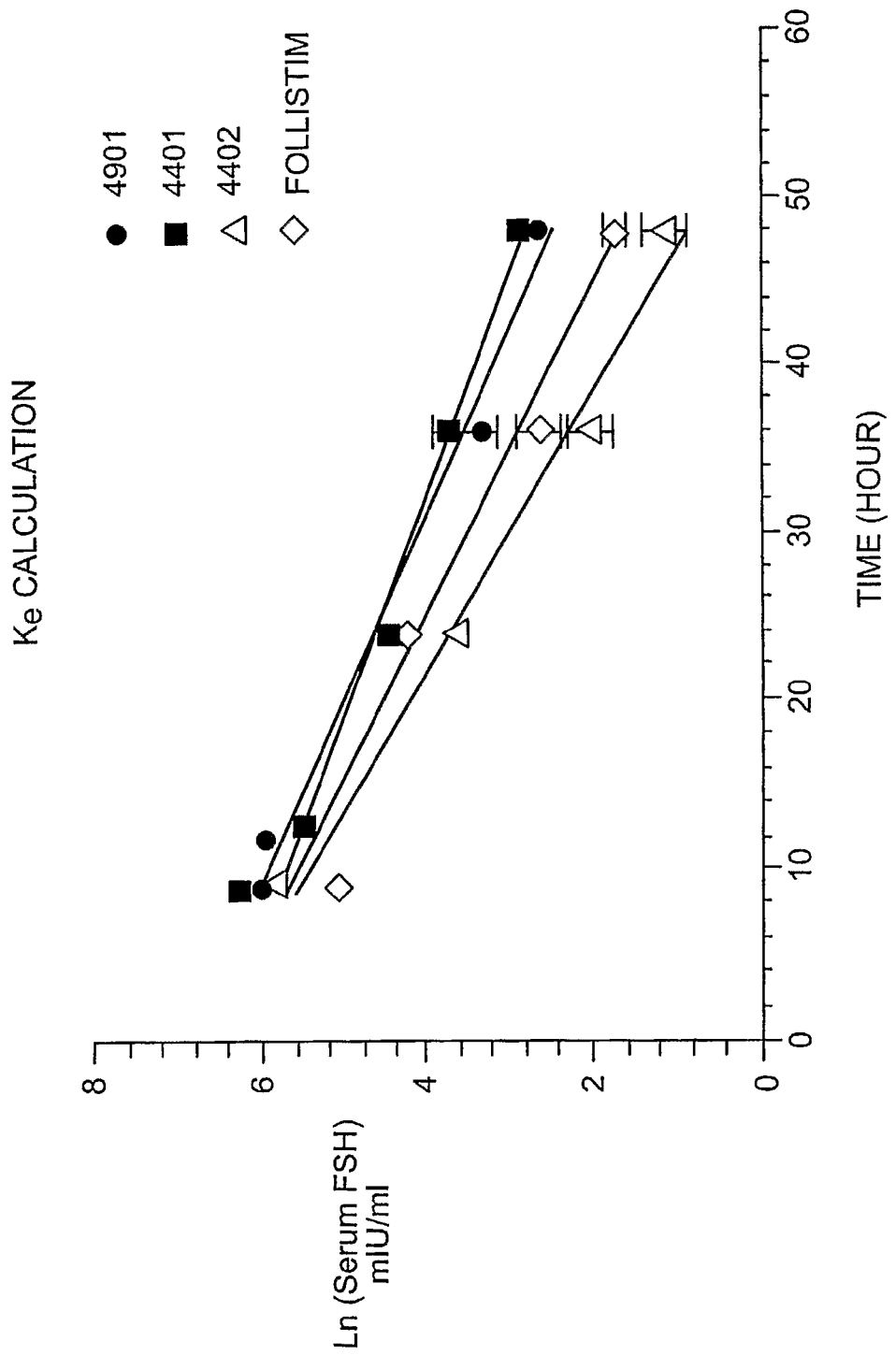
FIGS. 17 A and B are graphs showing the elimination and absorption of FSH analogs TR-4901, TR-4401, and TR-4402 versus wild type FSH.

Pharmokinetics experiments were performed to determine the rates of absorption and elimination of FSH analogs TR-4401, TR-4402, and TR-9901 compared to recombinant wild type FSH. A FSH Clearance Assay was performed to determine the amount of serum FSH in mIU/ml over time for TR-4401, TR-4402, and TR-9901 compared to recombinant wild type FSH. FIG. 17A provides the results of the assay. The figure shows delayed clearance of FSH analog TR-4401 compared to TR-4402 and TR-9901. FSH analog TR-4402 exhibited a reduced duration of action compared to the other analogs. Similarly, FIG. 17B shows the rate of elimination (ln [serum FSH mIU/ml] over time) for FSH analogs TR-4401, TR-4402, and TR-9901 compared to recombinant wild type FSH. TR-4402 was eliminated at a faster rate than the other analogs and recombinant wild type FSH (Follistim). Table 5 provides the data from the pharmokinetics experiment. The data confirms that the rate of elimination (Ke) and the rate of absorption (Ka) were greatest for FSH analog TR-4402. As expected, the serum half life (T½) was lowest for TR-4402 compared to the other analogs and the recombinant wild type FSH.

TABLE 5

Pharmokinetics Data for FSH Analogs TR-9901, TR-4401, and TR-4402 and Recombinant Wild Type FSH (Follistem)

|  | TR-9901 | TR-4401 | TR-4402 | Wild Type FSH |
|---|---|---|---|---|
| Ke | 0.09 | 0.076 | 0.124 | 0.099 |
| Ka | 0.5794 | 0.5654 | 1.55 | 0.3503 |
| V | 17.47 | 31.55 | 20.46 | 12.51 |
| AUC (0-t) (mIU * hour/ml) | 9328 | 6328 | 6868 | 8768 |
| Tmax (hour) | 3.8 | 4.1 | 1.8 | 5.0 |
| Cmax (mIU/ml) | 609.6 | 348.1 | 588.6 | 728.8 |
| T½ (hour) | 7.7 | 9.1 | 5.6 | 7.0 |
| AUC (mIU * Hour/ml) | 9508.8 | 6570.9 | 6897.1 | 8804.5 |

Pharmokinetics may have a dramatic effect on how a patient reacts to a FSH analog. Hypersensitive patients at risk for hyperstimulation syndrome may benefit from a FSH analog such as TR-4402 which acts faster and for a shorter duration than the other analogs. Other patients would likely benefit from a FSH analog such as TR-4401 which demonstrates a prolonged pharmokinetics action.

Additional pharmokinetics experiments were performed comparing TR-4401 to recombinant wild type FSH (Gonal F). In one experiment mice were injected with a single dose of recombinant wild type FSH or TR-4401. Terminal blood levels were determined 68 hours following the injection at necropsy. Terminal blood FSH values were at least 5-6 times higher with TR-4401 compared to recombinant wild type FSH. Table 6 provides dosing and terminal blood FSH data.

TABLE 6

Terminal Blood FSH Data for FSH

| FSH | Dosage (µg) | Terminal Blood FSH Values (mIU/ml) |
|---|---|---|
| Recombinant Wild Type FSH (Gonal F) | 2.22 µg | all animals less than 2.5 mIU/ml |
| TR-4401 | 0.22 µg | all animals less than 2.5 mIU/ml |
| TR-4401 | 2.2 µg | all animals between 12-15 mIU/ml |

Example 7

Modifications to Increase Serum Half Life of FSH Analogs

Figure 19:
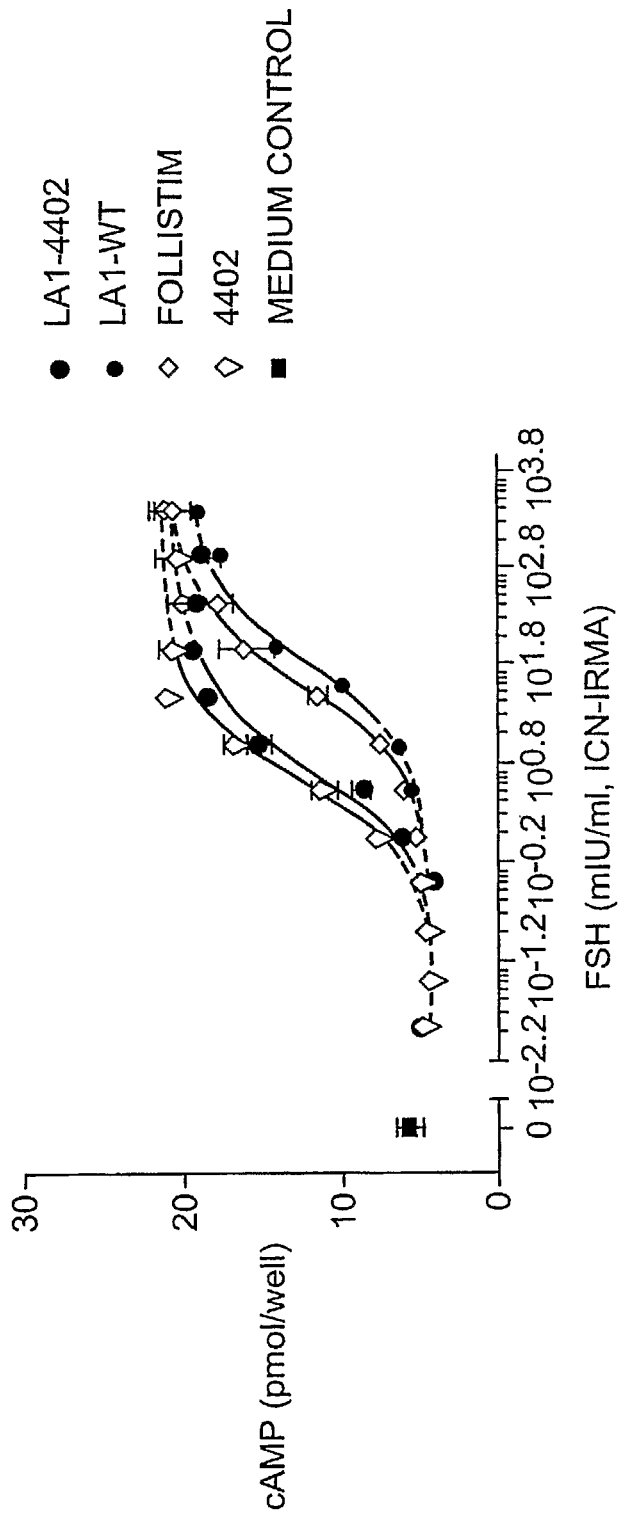
FIG. 19 is a graph showing cAMP production in CHO cells in response to LA1-4402 (TR-4402 further modified to increase FSH serum half-life) versus LA1 FSH (FSH modified to increase FSH serum half-life), TR-4402, and wild type FSH.

FHS analog TR-4402 was further modified by an N-terminal extension as previously described to enhance serum half life. Examples of further modifications which may enhance serum half life for FHS analogs are provided in FIG. 18. In vitro cAMP stimulation studies using CHO cells were conducted to compare N-terminal modified TR-4402 (LA1-4402), "wild type" N-terminal modified FSH (LA1-Wt), TR-4402, and recombinant wild type FSH (Follistem). FIG. 19 shows that the modifications extended the FSH serum half-life for the FSH analog TR-4402 and recombinant wild type FHS.

Figure 20:
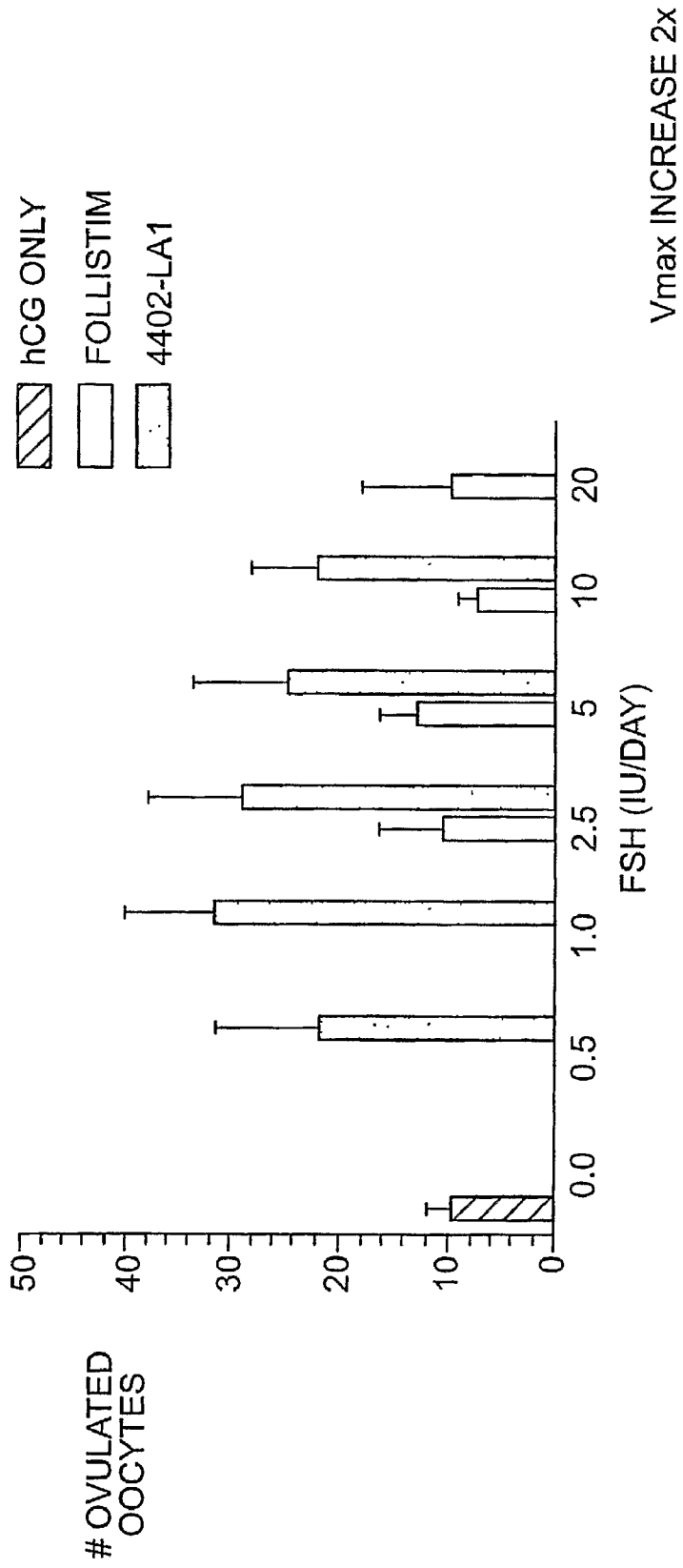
FIG. 20 is a graph showing an increase in number of ovulated oocytes produced in vivo in response to LA1-4402 (TR-4402 modified to increase serum half-life) versus wild type FSH (Follistem) and hCG only.

An in vivo ovulation assay was conducted in hybrid B6D2F1 mice to compare N-terminal modified TR-4402 to recombinant wild type FSH. The mice treated with N-terminal modified TR-4402 produced more oocytes than those treated with recombinant wild type FSH or hCG (control) for doses 0.5 IU, 1.0 IU, 2.5 IU, 5.0 IU, and 10 IU. The results of the experiment are shown in FIG. 20.

All publications, patents and patent applications discussed in this application are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of inducing superovulation in a cow comprising:
   administering an effective amount of a superactive follicle stimulating hormone (FSH) to said cow,
   wherein said superactive FSH is bovine FSH with an alpha chain comprising basic amino acid substitutions at positions 17, 18, 20 and 24; and
   wherein the alpha chain further comprises an ANTIV (SEQ ID NO: 3) N-terminal extension.

2. The method of claim 1, wherein superovulation is characterized by an increase in oocyte number as compared to a like animal receiving the same amount of recombinant wild type bovine FSH.

3. The method of claim 2, wherein the average oocyte number increases at least about 10% as a result of administration of said superactive bovine FSH at the maximally effective dose for oocyte number.

4. The method of claim 1, wherein the basic amino acid is an arginine, a lysine, or a histidine.

5. The method of claim 1, wherein the amino acid substitutions at positions 17, 18, 20 and 24 are arginine substitutions.

6. The method of claim 1, wherein said ANTIV (SEQ ID NO: 3) extension prolongs the half life of the superactive FSH.

7. The method of claim 1, wherein said superactive FSH is administered by injection or ingestion.

* * * * *

UNITED STATES PATENT AND TRADEMARK OFFICE
CERTIFICATE OF CORRECTION

PATENT NO. : 8,377,879 B2
APPLICATION NO. : 13/187956
DATED : February 19, 2013
INVENTOR(S) : Mariusz W. Szkudlinski et al.

It is certified that error appears in the above-identified patent and that said Letters Patent is hereby corrected as shown below:

In the Claims

Column 55, line 60 (Claim 1, line 8), please change ANTIV to ANITV

Column 56, line 60 (Claim 6, line 1), please change ANTIV to ANITV

Signed and Sealed this
Twenty-ninth Day of October, 2013

Teresa Stanek Rea
*Deputy Director of the United States Patent and Trademark Office*

SEQUENCE LISTING

<160> NUMBER OF SEQ ID NOS: 24

<210> SEQ ID NO 1
<211> LENGTH: 92
<212> TYPE: PRT

-continued

```
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Amino terminal extension; potential
      glycosylation recognition site

<400> SEQUENCE: 3

Ala Asn Ile Thr Val
1               5

<210> SEQ ID NO 4
<211> LENGTH: 9
<212> TYPE: PRT
<213> ORGANISM: Artificial Sequence
<220> FEATURE:
<223> OTHER INFORMATION: Amino terminal extension; potential
      glycosylation recognition site

<400> SEQUENCE: 4

Ala Asn Ile Thr Val Asn Ile Thr Val
1               5
```

```
<210> SEQ ID NO 5
<211> LENGTH: 4
<212> TYPE: PRT
<213> ORGANISM: Artificial Sequence
<220> FEATURE:
<223> OTHER INFORMATION: Negatively charged amino acid insert to modify
      protein half-life

<400> SEQUENCE: 5

Gly Glu Phe Thr
1

<210> SEQ ID NO 6
<211> LENGTH: 5
<212> TYPE: PRT
<213> ORGANISM: Artificial Sequence
<220> FEATURE:
<223> OTHER INFORMATION: Negatively charged amino acid insert to modify
      protein half-life

<400> SEQUENCE: 6

Gly Glu Phe Thr Thr
1               5

<210> SEQ ID NO 7
<211> LENGTH: 11
<212> TYPE: PRT
<213> ORGANISM: Artificial Sequence
<220> FEATURE:
<223> OTHER INFORMATION: FSH segment with negatively charged amino acid
      insert to modify protein half-life

<400> SEQUENCE: 7

Ala Asp Pro Gly Glu Phe Thr Val Gln Asp Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: FSH segment with negatively charged amino acid
      insert to modify protein half-life

<400> SEQUENCE: 8

Ala Asp Pro Gly Glu Phe Thr Thr Gln Asp Cys
1               5                   10

<210> SEQ ID NO 9
<211> LENGTH: 97
<212> TYPE: PRT
<213> ORGANISM: Artificial Sequence
<220> FEATURE:
<223> OTHER INFORMATION: Mutated FSH alpha mature peptide sequence with
      N-terminal extension

<400> SEQUENCE: 9

Ala Asn Ile Thr Val Ala Pro Asp Val Gln Asp Cys Pro Glu Cys Thr
1               5                   10                  15

Leu Gln Glu Asn Pro Phe Phe Ser Gln Pro Gly Ala Pro Ile Leu Gln
            20                  25                  30

Cys Met Gly Cys Cys Phe Ser Arg Ala Tyr Pro Thr Pro Leu Arg Ser
        35                  40                  45

Lys Lys Thr Met Leu Val Gln Lys Asn Val Thr Ser Glu Ser Thr Cys
    50                  55                  60

Cys Val Ala Lys Ser Tyr Asn Arg Val Thr Val Met Gly Gly Phe Lys
65                  70                  75                  80
```

Val Glu Asn His Thr Ala Cys His Cys Ser Thr Cys Tyr Tyr His Lys
            85                  90                  95

Ser

<210> SEQ ID NO 10
<211> LENGTH: 97
<212> TYPE: PRT
<213> ORGANISM: Artificial Sequence
<220> FEATURE:
<223> OTHER INFORMATION: Mutated FSH alpha mature peptide sequence with
      N-terminal extension

<400> SEQUENCE: 10

Ala Asn Ile Thr Val Ala Pro Asp Val Gln Asp Cys Pro Glu Cys Thr
1               5                   10                  15

Leu Gln Arg Asn Pro Phe Phe Ser Arg Pro Gly Ala Pro Ile Leu Gln
            20                  25                  30

Cys Met Gly Cys Cys Phe Ser Arg Ala Tyr Pro Thr Pro Leu Arg Ser
        35                  40                  45

Lys Lys Thr Met Leu Val Gln Lys Asn Val Thr Ser Glu Ser Thr Cys
50                  55                  60

Cys Val Ala Lys Ser Tyr Asn Arg Val Thr Val Met Gly Arg Phe Lys
65                  70                  75                  80

Val Glu Asn His Thr Ala Cys His Cys Ser Thr Cys Tyr Tyr His Lys
            85                  90                  95

Ser

<210> SEQ ID NO 11
<211> LENGTH: 101
<212> TYPE: PRT
<213> ORGANISM: Artificial Sequence
<220> FEATURE:
<223> OTHER INFORMATION: Mutated FSH alpha mature peptide sequence with
      N-terminal extension

<400> SEQUENCE: 11

Ala Asn Ile Thr Val Asn Ile Thr Val Ala Pro Asp Val Gln Asp Cys
1               5                   10                  15

Pro Glu Cys Thr Leu Gln Glu Asn Pro Phe Phe Ser Gln Pro Gly Ala
            20                  25                  30

Pro Ile Leu Gln Cys Met Gly Cys Cys Phe Ser Arg Ala Tyr Pro Thr
        35                  40                  45

Pro Leu Arg Ser Lys Lys Thr Met Leu Val Gln Lys Asn Val Thr Ser
50                  55                  60

Glu Ser Thr Cys Cys Val Ala Lys Ser Tyr Asn Arg Val Thr Val Met
65                  70                  75                  80

Gly Gly Phe Lys Val Glu Asn His Thr Ala Cys His Cys Ser Thr Cys
            85                  90                  95

Tyr Tyr His Lys Ser
            100

<210> SEQ ID NO 12
<211> LENGTH: 101
<212> TYPE: PRT
<213> ORGANISM: Artificial Sequence
<220> FEATURE:
<223> OTHER INFORMATION: Mutated FSH alpha mature peptide sequence with
      N-terminal extension

<400> SEQUENCE: 12

```
Ala Asn Ile Thr Val Asn Ile Thr Val Ala Pro Asp Val Gln Asp Cys
1               5                   10                  15

Pro Glu Cys Thr Leu Gln Arg Asn Pro Phe Phe Ser Arg Pro Gly Ala
            20                  25                  30

Pro Ile Leu Gln Cys Met Gly Cys Cys Phe Ser Arg Ala Tyr Pro Thr
                35                  40                  45

Pro Leu Arg Ser Lys Lys Thr Met Leu Val Gln Lys Asn Val Thr Ser
        50                  55                  60

Glu Ser Thr Cys Cys Val Ala Lys Ser Tyr Asn Arg Val Thr Val Met
65                  70                  75                  80

Gly Arg Phe Lys Val Glu Asn His Thr Ala Cys His Cys Ser Thr Cys
                85                  90                  95

Tyr Tyr His Lys Ser
            100
```

<210> SEQ ID NO 13
<211> LENGTH: 111
<212> TYPE: PRT
<213> ORGANISM: Artificial Sequence
<220> FEATURE:
<223> OTHER INFORMATION: Mutated FSH beta mature peptide sequence

<400> SEQUENCE: 13

```
Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Asn Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110
```

<210> SEQ ID NO 14
<211> LENGTH: 111
<212> TYPE: PRT
<213> ORGANISM: Artificial Sequence
<220> FEATURE:
<223> OTHER INFORMATION: Mutated FSH beta mature peptide sequence

<400> SEQUENCE: 14

```
Asn Ser Cys Arg Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
                35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Asn Ala Thr
65                  70                  75                  80

Gln Cys His Cys Gly Lys Cys Asp Ser Asp Ser Thr Asp Cys Thr Val
                85                  90                  95
```

```
Arg Gly Leu Gly Pro Ser Tyr Cys Ser Phe Gly Glu Met Lys Glu
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Mutated FSH beta mature peptide sequence

<400> SEQUENCE: 15

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Asn Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
            85                  90                  95

Arg Gly Leu Gly Pro Ser Tyr Cys Ser Phe Gly Glu Met Lys Glu
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Mutated FSH beta mature peptide sequence

<400> SEQUENCE: 16

Asn Ser Cys Arg Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Asn Glu Thr Val Arg Val Pro
50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
            85                  90                  95

Arg Gly Leu Gly Pro Ser Tyr Cys Ser Phe Gly Glu Met Lys Glu
            100                 105                 110

<210> SEQ ID NO 17
<211> LENGTH: 121
<212> TYPE: PRT
<213> ORGANISM: Homo sapiens

<400> SEQUENCE: 17

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
```

-continued

```
                35                  40                  45
Leu Pro Pro Leu Pro Gln Val Val Cys Thr Tyr Arg Asp Val Arg Phe
 50                  55                  60

Glu Ser Ile Arg Leu Pro Gly Cys Pro Arg Gly Val Asp Pro Val Val
 65                  70                  75                  80

Ser Phe Pro Val Ala Leu Ser Cys Arg Cys Gly Pro Cys Arg Arg Ser
                 85                  90                  95

Thr Ser Asp Cys Gly Gly Pro Lys Asp His Pro Leu Thr Cys Asp His
                100                 105                 110

Pro Gln Leu Ser Gly Leu Leu Phe Leu
                115                 120

<210> SEQ ID NO 18
<211> LENGTH: 24
<212> TYPE: PRT
<213> ORGANISM: Homo sapiens

<400> SEQUENCE: 18

Met Asp Tyr Tyr Arg Lys Tyr Ala Ala Ile Phe Leu Val Thr Leu Ser
 1               5                  10                  15

Val Phe Leu His Val Leu His Ser
                 20

<210> SEQ ID NO 19
<211> LENGTH: 18
<212> TYPE: PRT
<213> ORGANISM: Homo sapiens

<400> SEQUENCE: 19

Met Lys Thr Leu Gln Phe Phe Phe Leu Phe Cys Cys Trp Lys Ala Ile
 1               5                  10                  15

Cys Cys

<210> SEQ ID NO 20
<211> LENGTH: 20
<212> TYPE: PRT
<213> ORGANISM: Homo sapiens

<400> SEQUENCE: 20

Met Glu Met Leu Gln Gly Leu Leu Leu Leu Leu Leu Ser Met Gly
 1               5                  10                  15

Gly Ala Trp Ala
         20

<210> SEQ ID NO 21
<211> LENGTH: 692
<212> TYPE: PRT
<213> ORGANISM: Rattus norvegicus

<400> SEQUENCE: 21

Met Ala Leu Leu Leu Val Ser Leu Leu Ala Phe Leu Gly Thr Gly Ser
 1               5                  10                  15

Gly Cys His His Trp Leu Cys His Cys Ser Asn Arg Val Phe Leu Cys
                 20                  25                  30

Gln Asp Ser Lys Val Thr Glu Ile Pro Thr Asp Leu Pro Arg Asn Ala
                 35                  40                  45

Ile Glu Leu Arg Phe Val Leu Thr Lys Leu Arg Val Ile Pro Lys Gly
 50                  55                  60

Ser Phe Ala Gly Phe Gly Asp Leu Glu Lys Ile Glu Ile Ser Gln Asn
 65                  70                  75                  80
```

```
Asp Val Leu Glu Val Ile Glu Ala Asp Val Phe Ser Asn Leu Pro Lys
                85              90              95

Leu His Glu Ile Arg Ile Glu Lys Ala Asn Asn Leu Leu Tyr Ile Asn
            100             105             110

Pro Glu Ala Phe Gln Asn Leu Pro Ser Leu Arg Tyr Leu Leu Ile Ser
            115             120             125

Asn Thr Gly Ile Lys His Leu Pro Ala Val His Lys Ile Gln Ser Leu
        130             135             140

Gln Lys Val Leu Leu Asp Ile Gln Asp Asn Ile Asn Ile His Ile Val
145             150             155             160

Ala Arg Asn Ser Phe Met Gly Leu Ser Phe Glu Ser Val Ile Leu Trp
                165             170             175

Leu Ser Lys Asn Gly Ile Glu Glu Ile His Asn Cys Ala Phe Asn Gly
            180             185             190

Thr Gln Leu Asp Glu Leu Asn Leu Ser Asp Asn Asn Leu Glu Glu
        195             200             205

Leu Pro Asn Asp Val Phe Gln Gly Ala Ser Gly Pro Val Ile Leu Asp
    210             215             220

Ile Ser Arg Thr Lys Val His Ser Leu Pro Asn His Gly Leu Glu Asn
225             230             235             240

Leu Lys Lys Leu Arg Ala Arg Ser Thr Tyr Arg Leu Lys Lys Leu Pro
                245             250             255

Asn Leu Asp Lys Phe Val Thr Leu Met Glu Ala Ser Leu Thr Tyr Pro
            260             265             270

Ser His Cys Cys Ala Phe Ala Asn Leu Lys Arg Gln Ile Ser Glu Leu
        275             280             285

His Pro Ile Cys Asn Lys Ser Ile Leu Arg Gln Asp Ile Asp Asp Met
    290             295             300

Thr Gln Ile Gly Asp Gln Arg Val Ser Leu Ile Asp Asp Glu Pro Ser
305             310             315             320

Tyr Gly Lys Gly Ser Asp Met Met Tyr Asn Glu Phe Asp Tyr Asp Leu
                325             330             335

Cys Asn Glu Val Val Asp Val Thr Cys Ser Pro Lys Pro Asp Ala Phe
            340             345             350

Asn Pro Cys Glu Asp Ile Met Gly Tyr Asn Ile Leu Arg Val Leu Ile
        355             360             365

Trp Phe Ile Ser Ile Leu Ala Ile Thr Gly Asn Thr Thr Val Leu Val
    370             375             380

Val Leu Thr Thr Ser Gln Tyr Lys Leu Thr Val Pro Arg Phe Leu Met
385             390             395             400

Cys Asn Leu Ala Phe Ala Asp Leu Cys Ile Gly Ile Tyr Leu Leu Leu
                405             410             415

Ile Ala Ser Val Asp Ile His Thr Lys Ser Gln Tyr His Asn Tyr Ala
            420             425             430

Ile Asp Trp Gln Thr Gly Ala Gly Cys Asp Ala Ala Gly Phe Phe Thr
        435             440             445

Val Phe Ala Ser Glu Leu Ser Val Tyr Thr Leu Thr Ala Ile Thr Leu
    450             455             460

Glu Arg Trp His Thr Ile Thr His Ala Met Gln Leu Glu Cys Lys Val
465             470             475             480

Gln Leu Arg His Ala Ala Ser Val Met Val Leu Gly Trp Thr Phe Ala
                485             490             495

Phe Ala Ala Ala Leu Phe Pro Ile Phe Gly Ile Ser Ser Tyr Met Lys
```

```
            500                 505                 510
Val Ser Ile Cys Leu Pro Met Asp Ile Asp Ser Pro Leu Ser Gln Leu
        515                 520                 525

Tyr Val Met Ala Leu Leu Val Leu Asn Val Leu Ala Phe Val Val Ile
        530                 535                 540

Cys Gly Cys Tyr Thr His Ile Tyr Leu Thr Val Arg Asn Pro Thr Ile
545                 550                 555                 560

Val Ser Ser Ser Ser Asp Thr Lys Ile Ala Lys Arg Met Ala Thr Leu
                565                 570                 575

Ile Phe Thr Asp Phe Leu Cys Met Ala Pro Ile Ser Phe Phe Ala Ile
                580                 585                 590

Ser Ala Ser Leu Lys Val Pro Leu Ile Thr Val Ser Lys Ala Lys Ile
                595                 600                 605

Leu Leu Val Leu Phe Tyr Pro Ile Asn Ser Cys Ala Asn Pro Phe Leu
        610                 615                 620

Tyr Ala Ile Phe Thr Lys Asn Phe Arg Arg Asp Phe Phe Ile Leu Leu
625                 630                 635                 640

Ser Lys Phe Gly Cys Tyr Glu Met Gln Ala Gln Ile Tyr Arg Thr Glu
                645                 650                 655

Thr Ser Ser Ala Thr His Asn Phe His Ala Arg Lys Ser His Cys Ser
                660                 665                 670

Ser Ala Pro Arg Val Thr Asn Ser Tyr Val Leu Val Pro Leu Asn His
        675                 680                 685

Ser Ser Gln Asn
        690

<210> SEQ ID NO 22
<211> LENGTH: 695
<212> TYPE: PRT
<213> ORGANISM: Homo sapiens

<400> SEQUENCE: 22

Met Ala Leu Leu Leu Val Ser Leu Leu Ala Phe Leu Ser Leu Gly Ser
1               5                   10                  15

Gly Cys His His Arg Ile Cys His Cys Ser Asn Arg Val Phe Leu Cys
            20                  25                  30

Gln Glu Ser Lys Val Thr Glu Ile Pro Ser Asp Leu Pro Arg Asn Ala
        35                  40                  45

Ile Glu Leu Arg Phe Val Leu Thr Lys Leu Arg Val Ile Gln Lys Gly
    50                  55                  60

Ala Phe Ser Gly Phe Gly Asp Leu Glu Lys Ile Glu Ile Ser Gln Asn
65                  70                  75                  80

Asp Val Leu Glu Val Ile Glu Ala Asp Val Phe Ser Asn Leu Pro Lys
                85                  90                  95

Leu His Glu Ile Arg Ile Glu Lys Ala Asn Asn Leu Leu Tyr Ile Thr
            100                 105                 110

Pro Glu Ala Phe Gln Asn Leu Pro Asn Leu Gln Tyr Leu Leu Ile Ser
        115                 120                 125

Asn Thr Gly Ile Lys His Leu Pro Asp Val His Lys Ile His Ser Leu
    130                 135                 140

Gln Lys Val Leu Leu Asp Ile Gln Asp Asn Ile Asn Ile His Thr Ile
145                 150                 155                 160

Glu Arg Asn Ser Phe Val Gly Leu Ser Phe Glu Ser Val Ile Leu Trp
                165                 170                 175

Leu Asn Lys Asn Gly Ile Gln Glu Ile His Asn Cys Ala Phe Asn Gly
```

```
                180             185             190
Thr Gln Leu Asp Ala Val Asn Leu Ser Asp Asn Asn Leu Glu Glu
            195                 200             205

Leu Pro Asn Asp Val Phe His Gly Ala Ser Gly Pro Val Ile Leu Asp
        210                 215             220

Ile Ser Arg Thr Arg Ile His Ser Leu Pro Ser Tyr Gly Leu Glu Asn
225                 230              235             240

Leu Lys Lys Leu Arg Ala Arg Ser Thr Tyr Asn Leu Lys Lys Leu Pro
                245                 250             255

Thr Leu Glu Lys Leu Val Ala Leu Met Glu Ala Ser Leu Thr Tyr Pro
            260                 265             270

Ser His Cys Cys Ala Phe Ala Asn Trp Arg Arg Gln Ile Ser Glu Leu
        275                 280             285

His Pro Ile Cys Asn Lys Ser Ile Leu Arg Gln Glu Val Asp Tyr Met
    290                 295             300

Thr Gln Ala Arg Gly Gln Arg Ser Ser Leu Ala Glu Asp Asn Glu Ser
305                 310             315                 320

Ser Tyr Ser Arg Gly Phe Asp Met Thr Tyr Thr Glu Phe Asp Tyr Asp
                325             330                 335

Leu Cys Asn Glu Val Val Asp Val Thr Cys Ser Pro Lys Pro Asp Ala
            340                 345             350

Phe Asn Pro Cys Glu Asp Ile Met Gly Tyr Asn Ile Leu Arg Val Leu
        355                 360             365

Ile Trp Phe Ile Ser Ile Leu Ala Ile Thr Gly Asn Ile Ile Val Leu
    370                 375             380

Val Ile Leu Thr Thr Ser Gln Tyr Lys Leu Thr Val Pro Arg Phe Leu
385                 390             395                 400

Met Cys Asn Leu Ala Phe Ala Asp Leu Cys Ile Gly Ile Tyr Leu Leu
                405             410                 415

Leu Ile Ala Ser Val Asp Ile His Thr Lys Ser Gln Tyr His Asn Tyr
            420                 425             430

Ala Ile Asp Trp Gln Thr Gly Ala Gly Cys Asp Ala Ala Gly Phe Phe
        435                 440             445

Thr Val Phe Ala Ser Glu Leu Ser Val Tyr Thr Leu Thr Ala Ile Thr
    450                 455             460

Leu Glu Arg Trp His Thr Ile Thr His Ala Met Gln Leu Asp Cys Lys
465                 470             475                 480

Val Gln Leu Arg His Ala Ala Ser Val Met Val Met Gly Trp Ile Phe
                485             490                 495

Ala Phe Ala Ala Ala Leu Phe Pro Ile Phe Gly Ile Ser Ser Tyr Met
            500                 505             510

Lys Val Ser Ile Cys Leu Pro Met Asp Ile Asp Ser Pro Leu Ser Gln
        515                 520             525

Leu Tyr Val Met Ser Leu Leu Val Leu Asn Val Leu Ala Phe Val Val
    530                 535             540

Ile Cys Gly Cys Tyr Ile His Ile Tyr Leu Thr Val Arg Asn Pro Asn
545                 550             555                 560

Ile Val Ser Ser Ser Ser Asp Thr Arg Ile Ala Lys Arg Met Ala Met
                565             570                 575

Leu Ile Phe Thr Asp Phe Leu Cys Met Ala Pro Ile Ser Phe Phe Ala
            580                 585             590

Ile Ser Ala Ser Leu Lys Val Pro Leu Ile Thr Val Ser Lys Ala Lys
        595                 600             605
```

```
Ile Leu Leu Val Leu Phe His Pro Ile Asn Ser Cys Ala Asn Pro Phe
            610                 615                 620

Leu Tyr Ala Ile Phe Thr Lys Asn Phe Arg Arg Asp Phe Phe Ile Leu
625                 630                 635                 640

Leu Ser Lys Cys Gly Cys Tyr Glu Met Gln Ala Gln Ile Tyr Arg Thr
                645                 650                 655

Glu Thr Ser Ser Thr Val His Asn Thr His Pro Arg Asn Gly His Cys
                660                 665                 670

Ser Ser Ala Pro Arg Val Thr Ser Gly Ser Thr Tyr Ile Leu Val Pro
            675                 680                 685

Leu Ser His Leu Ala Gln Asn
            690                 695

<210> SEQ ID NO 23
<211> LENGTH: 700
<212> TYPE: PRT
<213> ORGANISM: Rattus sp.

<400> SEQUENCE: 23

Met Gly Arg Arg Val Pro Ala Leu Arg Gln Leu Leu Val Leu Ala Val
1               5                   10                  15

Leu Leu Leu Lys Pro Ser Gln Leu Gln Ser Arg Glu Leu Ser Gly Ser
                20                  25                  30

Arg Cys Pro Glu Pro Cys Asp Cys Ala Pro Asp Gly Ala Leu Arg Cys
            35                  40                  45

Pro Gly Pro Arg Ala Gly Leu Ala Arg Leu Ser Leu Thr Tyr Leu Pro
50                  55                  60

Val Lys Val Ile Pro Ser Gln Ala Phe Arg Gly Leu Asn Glu Val Val
65                  70                  75                  80

Lys Ile Glu Ile Ser Gln Ser Asp Ser Leu Glu Arg Ile Glu Ala Asn
                85                  90                  95

Ala Phe Asp Asn Leu Leu Asn Leu Ser Glu Leu Leu Ile Gln Asn Thr
            100                 105                 110

Lys Asn Leu Leu Tyr Ile Glu Pro Gly Ala Phe Thr Asn Leu Pro Arg
        115                 120                 125

Leu Lys Tyr Leu Ser Ile Cys Asn Thr Gly Ile Arg Thr Leu Pro Asp
130                 135                 140

Val Thr Lys Ile Ser Ser Ser Glu Phe Asn Phe Ile Leu Glu Ile Cys
145                 150                 155                 160

Asp Asn Leu His Ile Thr Thr Ile Pro Gly Asn Ala Phe Gln Gly Met
                165                 170                 175

Asn Asn Glu Ser Val Thr Leu Lys Leu Tyr Gly Asn Gly Phe Glu Glu
            180                 185                 190

Val Gln Ser His Ala Phe Asn Gly Thr Thr Leu Ile Ser Leu Glu Leu
        195                 200                 205

Lys Glu Asn Ile Tyr Leu Glu Lys Met His Ser Gly Ala Phe Gln Gly
    210                 215                 220

Ala Thr Gly Pro Ser Ile Leu Asp Ile Ser Ser Thr Lys Leu Gln Ala
225                 230                 235                 240

Leu Pro Ser His Gly Leu Glu Ser Ile Gln Thr Leu Ile Ala Leu Ser
                245                 250                 255

Ser Tyr Ser Leu Lys Thr Leu Pro Ser Lys Glu Lys Phe Thr Ser Leu
            260                 265                 270

Leu Val Ala Thr Leu Thr Tyr Pro Ser His Cys Cys Ala Phe Arg Asn
        275                 280                 285
```

-continued

```
Leu Pro Lys Lys Glu Gln Asn Phe Ser Phe Ser Ile Phe Glu Asn Phe
        290                 295                 300

Ser Lys Gln Cys Glu Ser Thr Val Arg Lys Ala Asp Asn Glu Thr Leu
305                 310                 315                 320

Tyr Ser Ala Ile Phe Glu Glu Asn Glu Leu Ser Gly Trp Asp Tyr Asp
                325                 330                 335

Tyr Gly Phe Cys Ser Pro Lys Thr Leu Gln Cys Ala Pro Glu Pro Asp
                340                 345                 350

Ala Phe Asn Pro Cys Glu Asp Ile Met Gly Tyr Ala Phe Leu Arg Val
            355                 360                 365

Leu Ile Trp Leu Ile Asn Ile Leu Ala Ile Phe Gly Asn Leu Thr Val
370                 375                 380

Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
                420                 425                 430

His Ala Ile Asp Trp Gln Thr Gly Ser Gly Cys Gly Ala Ala Gly Phe
            435                 440                 445

Phe Thr Val Phe Ala Ser Glu Leu Ser Val Tyr Thr Leu Thr Val Ile
            450                 455                 460

Thr Leu Glu Arg Trp His Thr Ile Thr Tyr Ala Val Gln Leu Asp Gln
465                 470                 475                 480

Lys Leu Arg Leu Arg His Ala Ile Pro Ile Met Leu Gly Gly Trp Leu
                485                 490                 495

Phe Ser Thr Leu Ile Ala Thr Met Pro Leu Val Gly Ile Ser Asn Tyr
                500                 505                 510

Met Lys Val Ser Ile Cys Leu Pro Met Asp Val Glu Ser Thr Leu Ser
            515                 520                 525

Gln Val Tyr Ile Leu Ser Ile Leu Ile Leu Asn Val Val Ala Phe Val
            530                 535                 540

Val Ile Cys Ala Cys Tyr Ile Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
                580                 585                 590

Ala Ile Ser Ala Ala Phe Lys Val Pro Leu Ile Thr Val Thr Asn Ser
            595                 600                 605

Lys Ile Leu Leu Val Leu Phe Tyr Pro Val Asn Ser Cys Ala Asn Pro
610                 615                 620

Phe Leu Tyr Ala Ile Phe Thr Lys Ala Phe Gln Arg Asp Phe Leu Leu
625                 630                 635                 640

Leu Leu Ser Arg Phe Gly Cys Cys Lys Arg Arg Ala Glu Leu Tyr Arg
                645                 650                 655

Arg Lys Glu Phe Ser Ala Tyr Thr Ser Asn Cys Lys Asn Gly Phe Pro
                660                 665                 670

Gly Ala Ser Lys Pro Ser Gln Ala Thr Leu Lys Leu Ser Thr Val His
            675                 680                 685

Cys Gln Gln Pro Ile Pro Pro Arg Ala Leu Thr His
690                 695                 700

<210> SEQ ID NO 24
```

<211> LENGTH: 699
<212> TYPE: PRT
<213> ORGANISM: Homo sapiens

<400> SEQUENCE: 24

```
Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
            20                  25                  30

Pro Cys Asn Cys Val Pro Asp Gly Ala Leu Arg Cys Pro Gly Pro Thr
        35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Gly Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400
```

-continued

```
Leu Ser Phe Ala Asp Phe Cys Met Gly Leu Tyr Leu Leu Ile Ala
            405                 410                 415
Ser Val Asp Ser Gln Thr Lys Gly Gln Tyr Tyr Asn His Ala Ile Asp
            420                 425                 430
Trp Gln Thr Gly Ser Gly Cys Ser Thr Ala Gly Phe Phe Thr Val Phe
            435                 440                 445
Ala Ser Glu Leu Ser Val Tyr Thr Leu Thr Val Ile Thr Leu Glu Arg
    450                 455                 460
Trp His Thr Ile Thr Tyr Ala Ile His Leu Asp Gln Lys Leu Arg Leu
465                 470                 475                 480
Arg His Ala Ile Leu Ile Met Leu Gly Gly Trp Leu Phe Ser Ser Leu
                485                 490                 495
Ile Ala Met Leu Pro Leu Val Gly Val Ser Asn Tyr Met Lys Val Ser
            500                 505                 510
Ile Cys Phe Pro Met Asp Val Glu Thr Thr Leu Ser Gln Val Tyr Ile
            515                 520                 525
Leu Thr Ile Leu Ile Leu Asn Val Val Ala Phe Phe Ile Ile Cys Ala
    530                 535                 540
Cys Tyr Ile Lys Ile Tyr Phe Ala Val Arg Asn Pro Glu Leu Met Ala
545                 550                 555                 560
Thr Asn Lys Asp Thr Lys Ile Ala Lys Lys Met Ala Ile Leu Ile Phe
            565                 570                 575
Thr Asp Phe Thr Cys Met Ala Pro Ile Ser Phe Phe Ala Ile Ser Ala
            580                 585                 590
Ala Phe Lys Val Pro Leu Ile Thr Val Thr Asn Ser Lys Val Leu Leu
    595                 600                 605
Val Leu Phe Tyr Pro Ile Asn Ser Cys Ala Asn Pro Phe Leu Tyr Ala
    610                 615                 620
Ile Phe Thr Lys Thr Phe Gln Arg Asp Phe Phe Leu Leu Leu Ser Lys
625                 630                 635                 640
Phe Gly Cys Cys Lys Arg Arg Ala Glu Leu Tyr Arg Arg Lys Asp Phe
                645                 650                 655
Ser Ala Tyr Thr Ser Asn Cys Lys Asn Gly Phe Thr Gly Ser Asn Lys
            660                 665                 670
Pro Ser Gln Ser Thr Leu Lys Leu Ser Thr Leu His Cys Gln Gly Thr
            675                 680                 685
Ala Leu Leu Asp Lys Thr Arg Tyr Thr Glu Cys
            690                 695
```